US012029873B2

(12) United States Patent
Unger et al.

(10) Patent No.: US 12,029,873 B2
(45) Date of Patent: Jul. 9, 2024

(54) NON-INVASIVE AGENT APPLICATOR

(71) Applicant: MuPharma Pty Ltd, Victoria (AU)

(72) Inventors: Harry Unger, Victoria (AU); Sean Michael Langelier, Victoria (AU); Mark Unger, Victoria (AU)

(73) Assignee: MuPharma Pty Ltd, Toorak (AU)

( * ) Notice: Subject to any disclaimer, the term of this patent is extended or adjusted under 35 U.S.C. 154(b) by 228 days.

(21) Appl. No.: 16/939,796

(22) Filed: Jul. 27, 2020

(65) Prior Publication Data
US 2021/0100995 A1 Apr. 8, 2021

Related U.S. Application Data

(63) Continuation of application No. 15/308,220, filed as application No. PCT/AU2015/050218 on May 6, 2015, now abandoned.

(30) Foreign Application Priority Data

May 6, 2014 (WO) ................ PCT/AU2014/050027
Nov. 12, 2014 (AU) ................................ 2014904549

(51) Int. Cl.
*A61M 37/00* (2006.01)
*A61N 1/04* (2006.01)
*A61N 1/30* (2006.01)

(52) U.S. Cl.
CPC ........ *A61M 37/0092* (2013.01); *A61M 37/00* (2013.01); *A61N 1/0448* (2013.01);
(Continued)

(58) Field of Classification Search
CPC ...... A61M 2037/0023; A61M 37/0015; A61M 2037/0007; A61M 2037/003; A61M 2037/0038
See application file for complete search history.

(56) References Cited

U.S. PATENT DOCUMENTS 6,050,988 A 4/2000 Zuck
6,096,000 A * 8/2000 Tachibana ........ A61B 5/150229
604/20
(Continued)

FOREIGN PATENT DOCUMENTS

AU 2013-901606 5/2013
JP H11-9701 A 1/1999
(Continued)

OTHER PUBLICATIONS

Ranasinghe et al., "Evaluation of Fowlpox-Vaccinia Virus Prime-Boost Vaccine Strategies for High-Level Mucosal and Systematic Immunity Against HIV-1", Vaccine, Jul. 26, 2006, 24(31-32), 5881-5895.

(Continued)

*Primary Examiner* — Emily L Schmidt
(74) *Attorney, Agent, or Firm* — Knobbe, Martens, Olson & Bear, LLP

(57) ABSTRACT

There is disclosed systems and methods for non-invasive delivery of an agent to biological tissues. Delivery of the agent to the tissues can be by one or more modalities. In some embodiments the systems and methods use agent carrier body including a tissue contacting surface for non-invasively engaging tissues under treatment. The tissue contacting surface can be at least partly defined by a plurality of protrusions that are in fluid communication with one or more reservoirs forming part of the agent carrier body. The protrusions may extend outward from an inside of a void and terminate at said tissue contacting surface.

12 Claims, 42 Drawing Sheets

(52) U.S. Cl.
CPC ..... *A61N 1/303* (2013.01); *A61M 2037/0007* (2013.01); *A61M 2037/0023* (2013.01); *A61M 2037/003* (2013.01)

(56) References Cited

U.S. PATENT DOCUMENTS

| | | | |
|---|---|---|---|
| 6,322,532 | B1* | 11/2001 | D'Sa et al. ........ A61K 41/0047 604/22 |
| 6,440,096 | B1 | 8/2002 | Lastovich et al. |
| 6,689,380 | B1 | 2/2004 | Marchitto et al. |
| 8,870,810 | B2 | 10/2014 | Mitragotri et al. |
| 2002/0045850 | A1 | 4/2002 | Rowe et al. |
| 2002/0099356 | A1 | 7/2002 | Unger et al. |
| 2002/0115957 | A1 | 8/2002 | Sun et al. |
| 2002/0138037 | A1 | 9/2002 | Weimann |
| 2003/0080085 | A1 | 5/2003 | Greenberg et al. |
| 2004/0106904 | A1* | 6/2004 | Gonnelli ........... A61M 37/0015 604/173 |
| 2004/0267234 | A1 | 12/2004 | Heart et al. |
| 2005/0112135 | A1 | 5/2005 | Cormier et al. |
| 2005/0153873 | A1 | 7/2005 | Chan et al. |
| 2006/0015058 | A1 | 1/2006 | Kellogg et al. |
| 2007/0031495 | A1 | 2/2007 | Eppstein et al. |
| 2007/0055179 | A1 | 3/2007 | Deem et al. |
| 2007/0078376 | A1 | 4/2007 | Smith |
| 2007/0156124 | A1 | 7/2007 | Ignon et al. |
| 2007/0232983 | A1 | 10/2007 | Smith |
| 2007/0276318 | A1 | 11/2007 | Henley |
| 2008/0161742 | A1 | 7/2008 | Domb et al. |
| 2008/0177220 | A1* | 7/2008 | Lindgren .......... A61M 37/0092 604/22 |
| 2008/0220092 | A1* | 9/2008 | Dipierro ................... A61P 3/00 514/249 |
| 2009/0030365 | A1 | 1/2009 | Tokumoto et al. |
| 2009/0209899 | A1 | 8/2009 | Unger et al. |
| 2009/0318853 | A1 | 12/2009 | Reed et al. |
| 2009/0326441 | A1 | 12/2009 | Iliescu et al. |
| 2010/0028388 | A1 | 2/2010 | Gibson et al. |
| 2010/0047327 | A1 | 2/2010 | Kuwahara et al. |
| 2011/0150924 | A1 | 6/2011 | Della Rocca et al. |
| 2021/0260353 | A1 | 8/2021 | Unger et al. |

FOREIGN PATENT DOCUMENTS

| | | |
|---|---|---|
| WO | WO 98/00194 A2 | 1/1998 |
| WO | WO 1999/064580 | 12/1999 |
| WO | WO 02/05890 A2 | 1/2002 |
| WO | WO 2004/093725 A2 | 11/2004 |
| WO | WO 2006/138658 A2 | 12/2006 |
| WO | WO 2007/143796 A1 | 12/2007 |
| WO | WO 2008/016331 A1 | 2/2008 |
| WO | WO 2008/093772 A1 | 8/2008 |
| WO | WO 2014/179840 A1 | 11/2014 |

OTHER PUBLICATIONS

Ranasinghe et al., "Mucosal HIV-1 Pox Virus Prime-Boost Immunization Induces High-Avidity CD8+ T Cells with Regime-Dependent Cytokine/Granzyme B Profiles", The Journal of Immunology, Feb. 15, 2007, 178(4), 2370-2379.

Ranasinghe et al., "A Comparative Analysis of HIV-Specific Mucosal/Systemic T Cell Immunity and Avidity Following rDNA/rFPV and Poxvirus-Poxvirus Primate Boost Immunisations", Vaccine, Apr. 5, 2011, 29(16), 3008-3020.

Ranasinghe et al., "Unique IL-13Rα2-Based HIV-1 Vaccine Strategy to Enhance Mucosal Immunity, CD8+ T-Cell Avidity and Protective Immunity", Mucosal Immunology, Nov. 2013, 6(6), 1068-1080.

International Patent Application No. PCT/AU2015/050218; Int'l Written Opinion and Search Report; dated Jul. 3, 2015; 13 pages.

International Patent Application No. PCT/AU2014/050027; Int'l Written Opinion and Search Report; dated Jun. 30, 2014; 21 pages.

Bhattacharjee et al., "Novel drug delivery systems for ocular therapy: With special reference to liposomal ocular delivery," European Journal of Ophthalmology, 2019, vol. 29, No. 1, pp. 113-126.

Gaudana et al., "Ocular Drug Delivery," The AAPS Journal, vol. 12, No. 3, Sep. 2010.

Zderic et al., "Ultrasound-Enhanced Transcorneal Drug Delivery," Cornea • vol. 23, No. 8, Nov. 2004, pp. 804-811.

International Search Report and Written Opinion dated Dec. 1, 2015 in Application No. PCT/AU2015/050707, 15 pages.

Office Action dated Oct. 12, 2023 in European Application No. 15 858 968.9, 6 pages.

Office Action dated Sep. 8, 2023 in Chinese Application No. 202010863682.4, 11 pages.

Office Action dated Apr. 12, 2023 in European Application No. 15 858 968.9, 6 pages.

Office Action dated Oct. 28, 2022 in Australian Application No. 2021205134, 5 pages.

Office Action dated Aug. 17, 2022 in Australian Application No. 2021203025, 5 pages.

Office Action dated Jul. 29, 2022 in Australian Application No. 2021205134, 4 pages.

Office Action dated Jul. 7, 2022 in Australian Application No. 2021203025, 3 pages.

Office Action dated Mar. 25, 2022 in Australian Application No. 2021203025, 4 pages.

Office Action dated May 24, 2022 in European Application No. 15 790 008.5, 8 pages.

Office Action dated Jun. 15, 2021 in Japanese Application No. 2020-153454, 7 pages.

Office Action dated Jan. 12, 2020 in Israel Application No. 242427, 6 pages.

Office Action dated Feb. 25, 2019 in Australian Application No. 2015255634, 5 pages.

Office Action dated Apr. 17, 2018 in Israel Application No. 242427, 4 pages.

Extended European Search Report dated Jun. 12, 2018 in Application No. 15 858 968.9, 8 pages.

Extended European Search Report dated Dec. 20, 2017 in Application No. 15 790 008.5, 8 pages.

U.S. File History printed Mar. 21, 2024 for U.S. Appl. No. 17/244,324, filed Apr. 29, 2021, entitled "Non-Invasive Agent Applicator,".

Bandi et al., "Advanced materials for drug delivery across mucosal barriers" Acta Biomaterialia 119 (2021) 13-29.

Homayun et al., "Challenges and Recent Progress in Oral Drug Delivery Systems for Biopharmaceuticals" Pharmaceutics, Published: Mar. 19, 2019, in 29 pages.

Leal et al., "Physicochemical properties of mucus and their impact on transmucosal drug delivery" International Journal of Pharmaceutics 532 (2017) 555-572.

McCright et al., "Engineering drug delivery systems to overcome mucosal barriers for immunotherapy and vaccination" Tissue Barriers, 2020, vol. 8, No. 1, e1695476, in 17 pages.

U.S. File History printed Mar. 21, 2024 for U.S. Appl. No. 18/608,706, filed Mar. 18, 2024, entitled "Non-Invasive Agent Applicator,".

U.S. File History printed Mar. 21, 2024 for U.S. Appl. No. 17/927,617, filed Nov. 23, 2022, entitled "Ultrasound Mediated Non-Invasive Drug Delivery Porous Carriers,".

* cited by examiner (a)

(b)

(c)

(d)

(a)

(b)

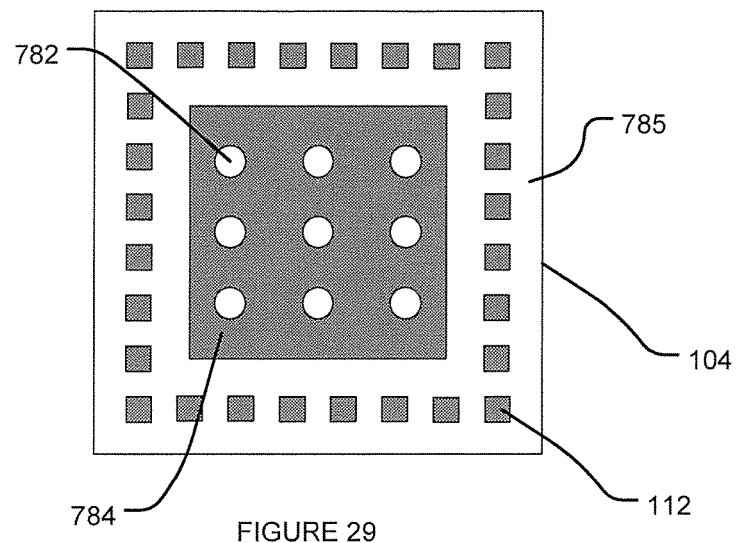
FIGURE 29
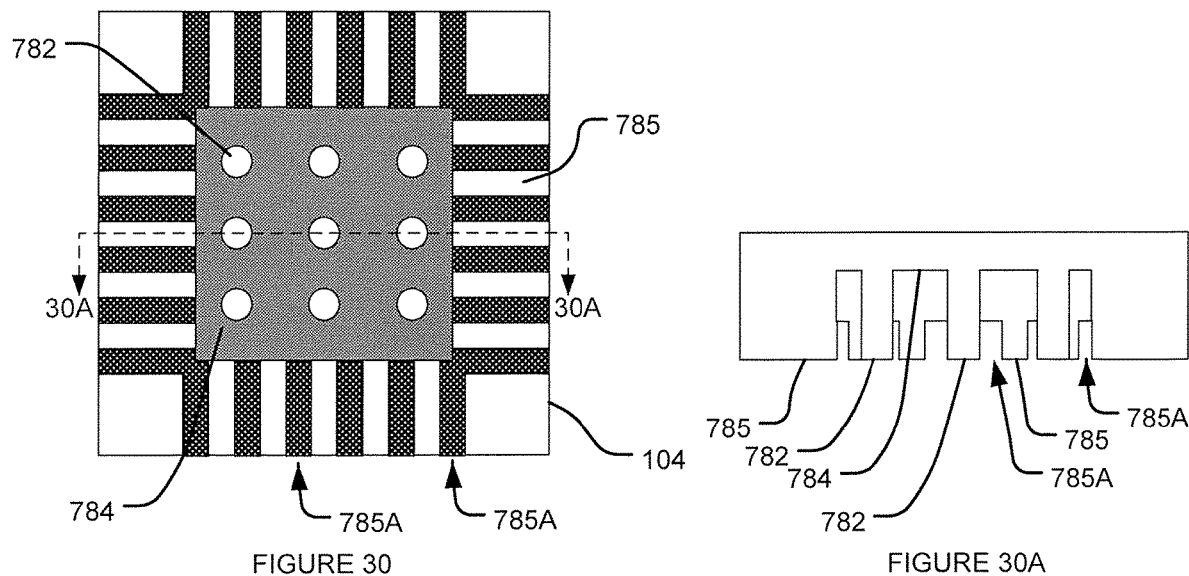
FIGURE 30
FIGURE 30A

NON-INVASIVE AGENT APPLICATOR

CROSS-REFERENCE TO RELATED APPLICATION

This application is a continuation of U.S. application Ser. No. 15/308,220, filed Nov. 1, 2016 which is a National Stage Application of International Application No. PCT/AU2015/050218, filed May 6, 2015, which claims the benefit of International Patent Application No. PCT/AU2014/050027, filed May 6, 2014 and Australian Patent Application No. 2014904549, filed Nov. 12, 2014, the disclosures of which are incorporated herein by reference in their entireties.

FIELD OF THE INVENTION

The present invention relates to the application of an agent to a target site. In a preferred form, the invention uses ultrasonic energy to transport an agent contained within an agent carrier body having a plurality of micro-scale structures within it to the target site non-invasively. In this preferred form, at the target site, penetration of the agent into the target site is enabled or enhanced through sonophoretic mechanisms.

BACKGROUND OF THE INVENTION

WO 2007/143796 discloses a method of delivering a molecule and/or particle to a target site using a device that includes generating ultrasound for enhancing the penetration of a molecule and/or particle into the target tissue.

The device of WO 2007/143796 includes an electro-conductive polymeric gel material that is loaded with a molecule and/or particle such as a pharmaceutical or ink etc. Application of an electric field to the electro conductive polymer gel releases substantially bound molecules or particles within the polymer gel matrix and, ultimately, such molecules or particles are transported through such polymer gel by ultrasound to the target tissue surface. At the target tissue surface, penetration of the molecule and/or particle into the tissue is enabled or enhanced through sonophoretic mechanisms.

One difficulty relating to this delivery mechanism is that the structure of the polymer gel can degrade over time, for example due to loss of moisture, which results in reduced propagation of the molecule and/or particle by ultrasound. Additionally, gels are poor transmitters of ultrasound reducing the efficacy of the sonophoretic process.

Furthermore, it can be time consuming and non-trivial to properly load an applicator with small volumes of the molecule and/or particle loaded polymeric gel.

In light of these problems, an improved device and mechanism for delivering an agent to a target tissue is sought.

Reference to any prior art in the specification is not, and should not be taken as, an acknowledgment or any form of suggestion that this prior art forms part of the common general knowledge in Australia or any other jurisdiction, or that this prior art could reasonably be expected to be ascertained, understood and regarded as relevant, or combined with other prior art by a person skilled in the art.

SUMMARY OF THE INVENTION

In one aspect of the invention there is provided an agent carrier for non-invasive delivery of an agent to biological tissues. Delivery of the agent to the tissues can be by one or more modalities. The modality of delivery can be characterised by a transportation stimulus or stimuli that causes transportation of the agent through the agent carrier. In a preferred form, the transportation stimulus also enhances or permits penetration of the agent into the tissue. Preferred forms of the invention use only ultrasound as the transportation stimulus.

In preferred forms the agent carrier includes an agent carrier body configured to retain agent within the agent carrier body. The agent carrier body has a tissue contacting surface for engaging tissues under treatment, wherein application of the transportation stimulus causes transportation of the agent through the agent carrier body to the tissue contacting surface.

The agent to be delivered can include one or more molecules or particles or one or more molecules and particles in any combination. The agent can be a fluid or can be carried in a fluid medium, e.g. by being dissolved, suspended or dispersed in a fluid medium, such as water, oil, an emulsion, a gel or the like. To give but a few examples, the agent can include, proteins, vaccines, nucleic acids, monoclonal antibodies, nanoparticles or molecular machines. In preferred embodiments the agent is a pharmaceutical or pharmaceutical composition. The pharmaceutical or one or more active pharmaceutical components of a pharmaceutical composition may be, without limit, any one of: a synthesised compound; a naturally occurring compound; or a biopharmaceutical. The purpose of the delivery of the pharmaceutical or pharmaceutical composition to the biological tissues can be for any desired clinical reason including: treating, curing or mitigating a disease, condition, or disorder; attenuating, ameliorating, or eliminating one or more symptoms of a particular disease, condition, or disorder; preventing or delaying the onset of one or more a disease, condition, or disorder or a symptom thereof; diagnosing a disease, condition, or disorder, or any agent intended to affect the structure or any function of the body. In other embodiments the agent can be an agent used for cosmetic purposes such as for cleansing, beautifying, promoting attractiveness, or altering the appearance of the body. The agent could also be a marker agent used for creating human or machine perceptible makings, e.g. ink or other. Other types of agents may also be used.

The transportation stimulus is the driving force for moving the agent through the agent carrier to the tissue-contacting surface, and may enhance and/or permit the penetration of the agent from the tissue-contacting surface into the tissue.

In some embodiments the tissue can be any human or animal biological tissue, including mucous membranes, skin and teeth. Preferably the tissue is ocular tissue or oral mucosa. In some embodiments the tissue is any plant tissue.

In an aspect there is provided an agent carrier body including a tissue contacting surface for non-invasively engaging tissues under treatment, the tissue contacting surface being at least partly defined by a plurality of protrusions. The protrusions may be in fluid communication with one or more reservoirs forming part of the agent carrier body. Each agent reservoir may comprise a void formed within the agent carrier body. The protrusions may extend outward from an inside of a void and terminate at said tissue contacting surface. The void may be formed by a peripheral structure, where at least part of said peripheral structure may terminate at the tissue contacting surface.

In some embodiments the peripheral structure terminates in a common plane with the protrusions. In others at least some of said protrusions defining the tissue contacting surface extend outward from the void beyond the peripheral structure. In some embodiments, the protrusions may terminate in a plane and the peripheral structure may terminate short of the plane such that the protrusions extend beyond the peripheral structure.

The agent carrier body may further include one or a multiplicity of micro channels extending at least partially through the agent carrier body to the tissue contacting surface enabling transportation of the agent to a tissue surface. The micro channels may extend through the agent carrier body to fluidly connect to an agent reservoir.

The agent carrier body of these aspects can include a stack of layers including a tissue-contacting layer, which includes the tissue-contacting surface, and at least one other layer. The tissue-contacting layer preferably has holes extending through it to define at least a portion of the micro channels in the body. In some embodiments a plurality of layers have holes formed therein to enable agent to be transported from one layer to the next. Preferably holes formed in one layer of the plurality of layers are aligned with holes in an adjacent layer so that a plurality of holes in a plurality of layers cooperate to form the micro channels. In some embodiments the holes decrease in diameter and increase in number from the first layer to the tissue-containing layer. The micro channels may have a varying cross-section along their length.

In some embodiments a reservoir for storing agent is at least partly (and optionally fully) formed in the agent carrier body.

The micro channels and/or agent reservoir(s) and/or protrusions are defined by internal exposed surfaces within the agent carrier body. Preferably these internal exposed surfaces are configured to possess predetermined hydrophilic, hydrophobic, and/or electro-conductive properties. In this case, at least part of the internal exposed surfaces could be modified or treated to configure their hydrophilic, hydrophobic, and/or electro-conductive properties.

The agent carrier body may include a port to enable loading of the agent carrier body and/or reservoir(s) with agent.

The agent carrier body can further include a stimulus generator, operable to generate transportation stimulus. The stimulus generator preferably includes an ultrasonic transducer.

In some embodiments, the agent carrier preferably includes a housing configured to mechanically support an agent carrier body, of any type described herein. The housing can include a mounting arrangement configured to be mounted to an applicator device. The mounting arrangement preferably enables selective attachment and removal of the agent carrier to and from the applicator device, such that the agent carrier can be replaced.

The agent carrier housing also may include a recess or other mounting formation formed therein for receiving the agent carrier body. In some embodiments the agent carrier body can be selectively attached to, or removed from, the recess or mounting formation such that the agent carrier body can be replaced.

The agent carrier can include a port to enable loading of the agent carrier body and/or reservoir(s) with agent.

The agent carrier can further include a stimulus generator, operable to generate a transportation stimulus. The stimulus generator preferably includes an ultrasonic transducer. At least part of the stimulus generator can be formed as part of the agent carrier body.

In a preferred embodiment the agent carrier or agent carrier body is a consumable applicator tip adapted for one-time use as part of an applicator device.

In another aspect of the invention there is provided a non-invasive applicator device comprising an agent carrier and/or an agent carrier body as described herein.

The agent carrier or agent carrier body can be coupled directly or indirectly to a handle unit to facilitate hand held operation of the applicator device. The handle unit preferably includes a mounting arrangement configured to cooperate with a complementary mounting arrangement of the agent carrier and/or agent carrier body.

The handle unit may include an ultrasonic generator to generate ultrasonic waves that are transmitted to the attached agent carrier and/or agent carrier body.

Preferably the agent carrier is a consumable applicator tip adapted for one-time use.

The agent carrier preferably includes an agent carrier body including a tissue contacting surface for non-invasively engaging tissues under treatment, the tissue contacting surface being at least partly defined by a plurality of protrusions.

The agent carrier may include one or more agent reservoirs for carrying said agent, wherein said protrusions are in fluid communication with one or more reservoirs forming part of the agent carrier. Each agent reservoir may at partly (or wholly) comprise a void formed within the agent carrier body.

Also disclosed herein is a method of dispensing an agent from an agent carrier described herein. The method comprises holding the agent within an agent carrier, said agent carrier including a solid agent carrier body. The method can further comprise engaging a tissue contacting surface of the agent carrier body with a tissue surface of the biological tissue. The method can further comprise dispensing agent from the agent carrier to the tissue surface by applying at least one transportation stimulus to cause transportation of the agent through the agent carrier body to the tissue surface.

In some forms the method further includes applying the transportation stimulus to the tissue via the agent carrier to enhance or permit penetration of the agent into the biological tissue.

Holding the agent within an agent carrier can include holding at least some agent within the carrier body.

In preferred embodiments the agent carrier body terminates at its tissue contacting surface in a plurality of protrusions. In this case, engaging a tissue contacting surface of the agent carrier body with a tissue surface of the biological tissue, includes engaging the tissue surface of the biological tissue with the protrusions of the agent carrier body. Such engagement preferably does not involve mechanically penetrating any layer of biological tissue with the protrusions.

In another aspect of the invention there is provided a method of dispensing an agent from an agent carrier, an agent carrier body, or an applicator device as described previously, the method including: contacting the tissue-contact surface of the agent carrier with a tissue surface; and dispensing agent from the agent carrier body to the tissue surface and into the target tissue.

In some embodiments of any of the above methods the step of dispensing the agent includes generating ultrasonic waves for agent transport to the tissue contact surface. Even more preferably the method includes propagating ultrasonic waves through the agent carrier to the tissue. This aids the delivery of the agent through the tissues via sonophoresis.

In some embodiments of any of the above methods the step of dispensing the agent can include applying an electrical voltage across the agent carrier body to cause agent transport to the tissue contact surface. The electric voltage can also provide for the transport of agent into and through the tissue via iontophoresis. Even more preferably the method includes propagating an electric current through the agent carrier to the tissue.

In yet another aspect of the present invention there is provided a method of dispensing an agent from an agent carrier, an agent carrier body or an agent applicator device as described herein. The method including, contacting the tissue contacting surface of the agent carrier body with a tissue surface; and dispensing agent from the agent carrier to the tissue surface. The step of dispensing the agent preferably includes generating ultrasonic waves to cause or facilitate agent transportation to the tissue-contacting surface. The method can include the application of ultrasonic waves to the tissue surface to non-invasively cause or facilitate agent penetration of the agent into and through the tissue via sonophoresis.

The method further includes propagating ultrasonic waves through the agent carrier or agent carrier body to the tissue.

In another aspect the present invention provides a method of loading agent into any one of an agent carrier, agent carrier body, an agent applicator device as described herein. The method includes, exposing the agent carrier body to the agent to enable filling either of both of, a reservoir or micro channels in fluid communication with said reservoir, with said agent.

The method can include applying a negative pressure to the agent carrier or agent carrier body to draw agent into the micro channels or agent reservoirs in fluid communication with the micro channels. The method can include applying a positive pressure to the agent carrier or agent carrier body to inject the agent into the micro channels or agent reservoirs in fluid communication with the micro channels.

The step of filling the micro channels or agent reservoirs with the agent can include the application of ultrasonic energy to the agent carrier or agent carrier body to draw agent into the agent carrier or agent carrier body.

In some embodiments, the voids and/or micro channels in the agent carrier body are loaded by virtue of capillary forces when the agent carrier is in contact with the agent.

In another aspect the present invention provides a method of delivering an agent to a biological tissue, including: applying said agent using an agent carrier, agent carrier body or applicator of any one of the aspects or embodiments described herein, wherein ultrasound is the transportation stimulus; and configuring the operational parameters of the application to enhance or cause delivery of said agent to a selected depth within such tissue. The operational parameters configured may include (but are not limited to) any one or more of:
  Application pressure;
  Ultrasonic frequency;
  Ultrasonic power level;
  Ultrasonic waveform;
  Ultrasonic application duration;
  Ultrasonic application duty cycle; and
  Ultrasound direction.

Preferably the operational parameters are selected to deliver a chosen amount of agent to a chosen depth within tissue.

The method may involve delivering the agent to or beyond any one or more of the following tissues or tissue layers:
  Mucous Membrane;
  Epithelium
  Sub-epithelium
  Mucosa;
  Sub-mucosa
  Mucous membrane vasculature
  Cornea;
  Corneal epithelium
  Bowman's membrane
  Corneal stroma
  Corneal Endothelium
  Conjunctiva;
  Tenon's Fascia;
  Episclera:
  Sclera;
  Choroid;
  Choriocapillaris;
  Bruch's membrane;
  Retinal Pigment Epithelium;
  Neural retina;
  Retinal blood vessels;
  Internal Limiting Membrane: and
  Vitreous.

As used herein, except where the context requires otherwise, the term "comprise" and variations of such term, such as "comprising", "comprises" and "comprised", are not intended to exclude further things, additives, components, integers or steps. Also, as used herein, except where there is express wording to the contrary, specifying anything after the words 'include' or 'for example' or similar expressions does not limit what else is included.

BRIEF DESCRIPTION OF THE DRAWINGS

Further aspects of the present invention and further embodiments of the aspects described in the preceding paragraphs will become apparent from the following description, given by way of example and with reference to the accompanying drawings. In the drawings:

FIGS. 29 to 30A illustrate diagrammatically two hybrid agent carrier bodies according to an embodiment of the present invention.

DETAILED DESCRIPTION OF THE EMBODIMENTS

Figure 1A:
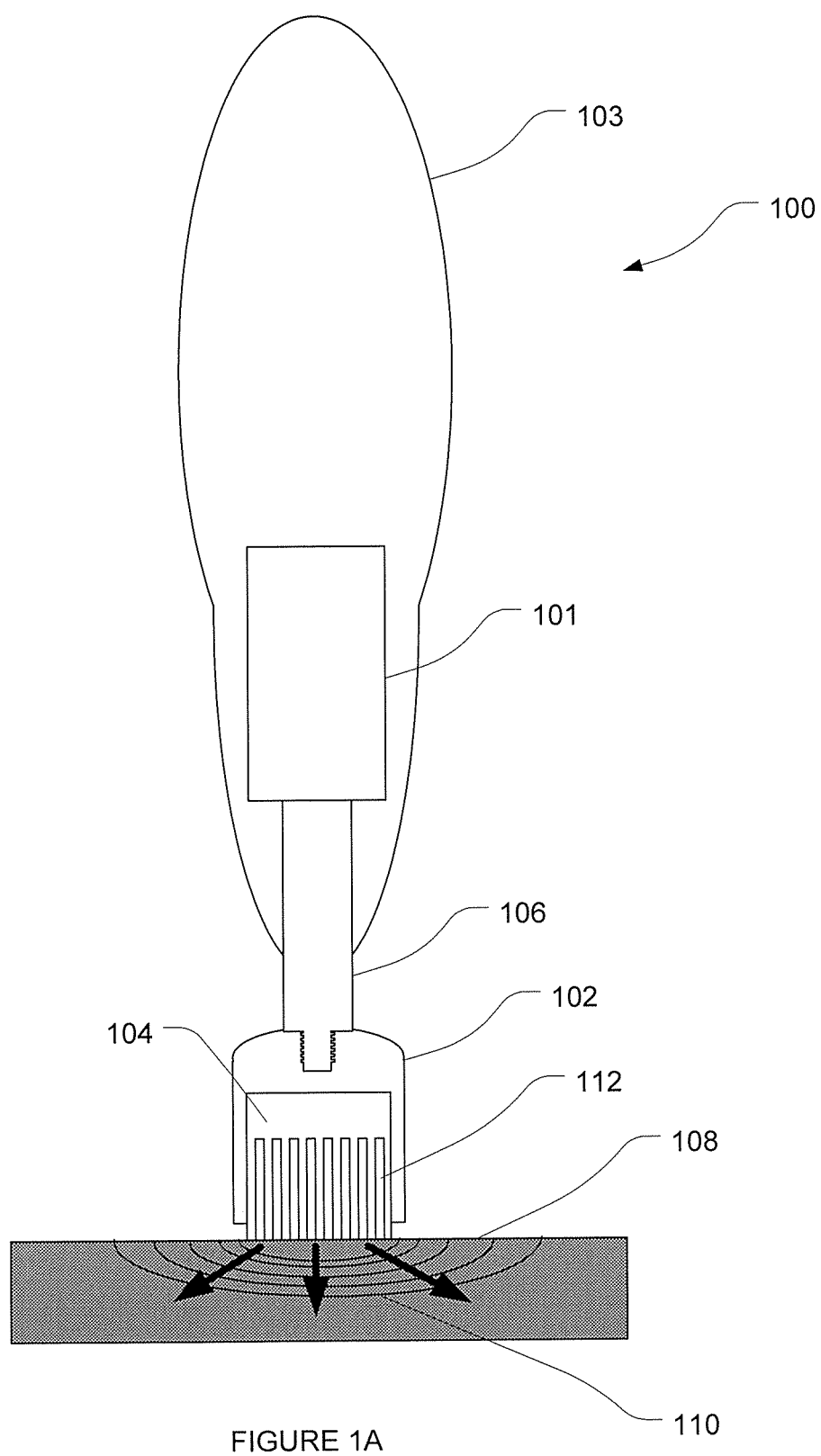
FIG. 1A shows a schematic cross-sectional block diagram of an applicator device according to one embodiment, being applied to a tissue surface and provides an illustration of the overall components of one exemplary applicator device.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessary obscuring.

This description follows the following outline:
1. Overview
2 General principles and Micro-Channel Embodiments
3 Protrusion-based embodiments
4 Hybrid and alternative embodiments
5. Loading and use examples
6. Trial results
7. References

1. OVERVIEW

Background to the Present Embodiments

The delivery of drugs, including macromolecules larger than approximately 500 Daltons and hydrophilic drugs, to the body without using hypodermic injections, ingestion or surgery has long been a desired goal in medicine.

A myriad of drug delivery devices using a variety of technologies have been developed to achieve this ("Drug delivery devices"), however, these have been unable to non-invasively deliver to the body a large range of drugs in a safe, practical, predicable and effective way. Historically, the transdermal route, has been the primary focus of non-invasive drug delivery applications.

The advantages of delivering drugs to the body without ingestion, includes bypassing the degradation of drugs by the acid and or alkaline regions of the gastrointestinal tract and enzymes in the gastro-intestinal tract and avoiding their metabolism by the liver enzymes as well as removal of the dyspeptic side effects of drugs. Advantages of delivering macromolecules or hydrophilic drugs to the body without hypodermic injections include decreased or elimination of pain, local trauma and side effects, increased patient compliance, and lowering the incidence of needle contamination, disease transmission and needle misuse. Delivering drugs to the body without surgery that is required to introduce implanted devices has advantages including decreased or elimination of pain, local trauma and side effects and elimination of any anaesthetic risk.

Drug delivery devices may be applied to skin for both targeted applications and as a portal for systemic drug delivery. The primary barrier for transdermal transport of hydrophilic molecules and/or molecules larger than approximately 500 Daltons is the outermost layer of the epidermis, the stratum corneum, which is typically 10-20 μm in thickness. The stratum corneum is a nonviable cell layer that is comprised of highly-crosslinked keratinocytes embedded in a continuous matrix of skin lipids. Drug delivery devices are needed to overcome these natural semipermeable barriers to deliver the drugs. Drug delivery devices for the skin commonly use microneedles and/or iontophoresis as the primary means of delivering drugs to such tissues.

Another application site for Drug Delivery devices, less commonly used as a portal for systemic drug delivery, is mucosal membranes. The primary barrier for trans-mucosal transport of hydrophilic molecules and macromolecules is the epithelial layer. Drug delivery devices for trans-mucosal delivery commonly use nasal sprays, inhalants and/or iontophoresis as the primary means of delivering drugs.

The following technology (either solely or in any combination) is presently used in Drug delivery devices:

Iontophoresis

Drug delivery devices that deliver an agent to the body using a process known as iontophoresis operate by generating an electric current that results from the application of electrodes which create and maintain a potential difference between the device and the target tissue. Ionic forms of the drug to be delivered are transported in the electric current and thereby gain access to the target tissue. Devices that deliver an agent to the body using iontophoresis commonly have a continuous layer of drug containing fluid in which the electrode within the device is bathed. The application time tends to be long, in many cases, hours.

Agents that can be delivered to the body using iontophoresis must be both hydrophilic and have an electrical charge. Iontophoresis is not capable of delivering neutral molecules and/or particles including large proteins and vaccines.

Microneedles

Microneedles are discrete protrusions that function to pierce one or more layers of tissue. Depending on their application, microneedles can be partly or fully hollow or solid. Microneedles used in Drug delivery devices commonly function as: 1) structures that can increase permeability within tissue when combined with certain external stimuli; 2) structures incorporating an agent that dissolves into tissue; 3) hollow conduits for injection of agent into tissue; and/or 4) structures designed to scrape surface tissue or expose internal tissue. Microneedles are commonly incorporated into patches that are applied to skin either with adhesives or are mechanically engaged. They may also contain compounds to enhance the penetration of agent through tissue or applied to tissue after it has been pretreated with permeation enhancer compounds.

Sonophoresis

Drug delivery devices that deliver an agent to the body using a process known as sonophoresis operate through applying ultrasound to tissue that both increases the permeability of tissues and provides kinetic energy to the agent. The increase in permeability of tissues through ultrasound results from a number of phenomena including any one or more of the following: 1) cavitation though generation and oscillation of gas bubbles; 2) thermal effects from an increase in temperature causing induction of convective transport; or 3) mechanical effects through occurrence of stresses due to pressure variation induced by ultrasound. Low frequency ultrasound, generally in the range of 20-200 kHz, but preferably below 100 kHz, has been found to be more effective for sonophoresis than higher frequencies of ultrasound. The prime method of sonophoretic transport through skin requires power sufficient to create cavitation.

Drug delivery devices that deliver an agent to the body using sonophoresis commonly have a layer of fluid containing the agent in which the source of the ultrasound is bathed or is placed in close proximity. These devices also sometimes include various kinds of microneedles where the microneedles are bathed in such fluid. In each of the aforementioned devices, because fluids attenuate the power of ultrasound more than solid materials, and the volume of fluid on which the ultrasound acts is large with respect to solid structures within or around it, the ultrasound energy is considerably attenuated by the time the wavefront approaches the tissue surface. This ultrasonic wavefront is partially reflected from the tissue surface back into the fluid layer which further disrupts the efficiency of the ultrasound resulting in the need for more power to be applied to the fluid. These techniques have some potential drawbacks, for example, ultrasound applied to tissue can, depending upon the magnitude of power, cause localised damage from cavitation and thermal effects. The threshold for damaging tissue from ultrasonic power depends on a variety of factors including the type of tissue, the thickness of tissue, the health of the tissue and whether the tissue is intact. For example, the skin is capable of tolerating more ultrasonic power being applied to it than mucous membranes on the eye. Furthermore, ultrasound applied to an agent may, depending upon the magnitude of power, cause the agent, or molecules within it, to cleave or denature or otherwise be damaged from cavitation, thermal or mechanical effects. Agents which are known to have a low tolerance to ultrasonic cavitation, mechanical forces or temperatures above 40 degrees centigrade include vaccines, proteins and other biologics.

Overview of the Embodiments

In summary, preferred embodiments of the present invention use low frequency ultrasound at low power to transport an agent, contained within an agent carrier body having micro-scale structures within it, for delivering the agent non-invasively to tissues.

As will be appreciated, ultrasound will be applied over one or more frequency bands or over a frequency spectrum having several bands. Preferably the band(s) correspond to a resonant frequency of the applicator device including the agent carrier body, and optionally one or more harmonics of the resonant frequency. In some forms of the present invention, the ultrasound applied is of a low frequency, between 20 kHz to 100 kHz, most preferably the frequency of the ultrasonic energy is between 20 kHz and 40 kHz. This is particularly preferred for use with the mucous membranes, eyes and other delicate tissues. However, in other embodiments the applicator device may have a resonant frequency lower than this, and the devices describe herein may be operated with a primary resonant frequency at the tip of the agent carrier body of around 10 kHz. In testing, applicators suitable for use with embodiments of the present invention have been operated at frequencies in any one or more of the following frequency bands, a band centred at or about 10 kHz; 20 kHz, 22 kHz, 28 kHz, 28.19 kHz, and 38 kHz and/or frequency bands of 20-25 kHz, 25-30 kHz, 38-40 kHz, 40-45 kHz, 40 to 60 kHz, 40-80 kHz, 140-160 kHz.

For other tissues, such as skin, the ultrasonic frequency may be outside these ranges.

In preferred forms of the present invention, the ultrasonic power used is relatively low, typically in the range 0.05 to 3.5 $Wcm^{-2}$. Higher intensity ultrasonic power may be needed in some applications. In these cases it may be necessary to pulse or otherwise control the duty cycle of the ultrasonic energy to prevent tissue damage, (e.g. from thermal effects) and/or to prevent damage to the agent.

The ultrasonic energy applied to the applicator causes reciprocating motion of the tissue contacting surface. In typical embodiments the displacement of the tissue contacting surface from its mean position may be between about 100 nm and 2200 nm. Embodiments may operate with a displacement more than 200 nm. Embodiments may operate with a displacement less than 2100 nm. Embodiments may operate with a displacement more than 400 nm. The embodiments used in the experiments operated with a displacement less than 500 nm, and more specifically less than 400 nm.

FIG. 31A illustrates plots of the displacement (nm) and velocity (m/s) during operation of two types of applicator, MP1 and MP4, with two types of tip assembly, e.g. agent carrier, "Tip assembly 1" and "Tip assembly 2" at a range of frequencies between 0 and 200 kHz.

FIG. 31B illustrates plots of the displacement (nm) and velocity (m/s) during operation of three types of handle unit useable in an applicator according to an embodiment, AMO1 (Model no. Sov37706); AMO2 (Model no. Sov39302) and ALCON1 (Model no. Turbo Sonic-375), without a tip assembly, e.g. agent carrier, at a range of frequencies between 0 and 200 kHz.

FIG. 31C illustrates plots of the displacement (nm) and velocity (m/s) during operation of three handle units, AMO1; AMO2 and ALCON1, with a second type of tip assembly, e.g. agent carrier, at a range of frequencies between 0 and 200 kHz.

FIG. 31D illustrates plots of the displacement (nm) and velocity (m/s) during operation of three types of applicator, AMO1; AMO2 and ALCON1, with a third type of tip assembly, e.g. agent carrier, at a range of frequencies between 0 and 200 kHz.

FIG. 32 illustrates the tip displacement of the MP4 and AMO 1 applicators when driven at selected frequencies over a range of drive voltages. The MP4 system was driven through an RF amplifier at 22 kHz over a range of input voltages of between 50 to 400V peak to peak. The AMO1 was driven at 28.19 kHz over the same voltage range.

The studies of the devices were performed using a laser doppler vibrometer model MSA400 from Polytec instruments in Germany.

As can be seen by selecting the frequency (or frequency band) of operation desired oscillation parameters can be chosen. These parameters will vary depending on the particular agent carrier used. In preferred embodiments these devices will be operated in a frequency band that corresponds to one or more of the peaks in motion as illustrated in the plots.

In typical embodiments the velocity of motion of the tissue contacting surface may be between about 0.01 m/s and 0.4 m/s. Embodiments may operate with a velocity more than 0.03 m/s. Embodiments may operate with a velocity less than 0.36 m/s. Embodiments may operate with a velocity more than 0.06 m/s. The embodiments used in the experiments operated with a displacement less than 0.05 m/s.

Embodiments of the present invention may advantageously be used in the delivery of agent to delicate tissues, such as mucous membranes (including the conjunctiva, buccal mucosa and labial mucosa), the cornea and the external coats of the eye.

The ultrasonic power and/or frequency parameters in embodiments may be increased or decreased for a variety of reasons including to control the depth of penetration of the agent into tissue. As an example, the ultrasonic power and/or frequency parameters used for delivering agent to the epithelial surface cells of a mucus membrane, may be lower than power and/or frequency parameters used for delivering agent to the rich blood vessel capillary beds and deeper connective tissue layers that lie below the epithelial surface.

It is intended that the agent carrier body does not penetrate any layer of the tissue surface. Although some superficial cell damage may occur in using embodiments of the present invention, it is not intended and is not relied upon in order to achieve delivery of the agent to the target tissue. Maintaining an intact tissue surface as much as possible may serve to more accurately control the depth of penetration of the agent into tissue layers.

The various micro-scale structures within the agent carrier body described herein, amongst other things serves the purpose of making direct contact between the agent carrier body and the tissue surface to propagate ultrasonic energy, thereby minimizing the extent of any continuous layer fluid within the agent carrier body and between the agent carrier body and the target tissue (which tend to attenuate ultrasonic waves).

One group of embodiments first described in the Applicant's Australian patent application 2013901606, include an agent carrier body having microstructures that form a plurality of micro channels surrounded by rigid walls for delivery of various agents. The micro channels are typically in the range of approximately 25 to 100 µm across when measured transverse to the direction of delivery, may have a length of between approximately 0.5 mm to 2 mm. Any suitable cross-sectional and/or longitudinal geometry can be used.

In use, each channel contains the agent in a fluid column within the channel and the ultrasonic energy is directly applied to each fluid column and the walls surrounding the fluid column. The ultrasonic wave is generated to be longitudinal in nature, i.e. it propagates along the channel. In some embodiments, by using the micron scale architecture of the microstructures, the wave front that impacts the fluid column is concentrated within each micro channel thus reducing attenuation of ultrasound. Reflection of ultrasonic waves at tissue surface is minimized by having direct contact of the device, and most preferably the agent carrier body, with the tissue surface so as not to permit the presence of a fluidic space between them. This further assists molecules to efficiently move toward the target tissue under the influence of ultrasound along the ultrasonic wavefront path. The ultrasonic waves are also carried in the agent carrier body, and specifically in the walls defining the micro channels. Since they do not attenuate the ultrasonic energy as much as fluids do, they efficiently transmit the sonophoretic power to the target tissue directly.

In preferred embodiments, the tissue-contacting surface of the device is not separated from the tissue by a continuous layer of fluid. The tissue-contacting surface of the agent carrier body presents a surface that has areas of solid body and liquid agent (i.e. the openings of the micro channels), in some embodiments approximating a solid-liquid "checker board"-like array. This arrangement may facilitate the sonophoretic ability of the device since the faces of the solid walls directly contact the tissue. In such embodiments the device architecture might be conceptualized as a large number of individual micron-scale sonophoretic delivery devices tightly packed and joined together.

Another group of new embodiments include a plurality of micro-scale structures that is formed by micron-scale protrusions that together define the tissue contacting surface of the agent carrier body. These protrusions contact the target tissue and the agent to be delivered surrounds them. In preferred forms, the agent carrier body has a peripheral structure, typically a wall, that surrounds the protrusions and contains the agent in use. This embodiment has a lower ratio of microstructures to fluid within the agent carrier body compared to an agent carrier body comprised of microchannels. Preferably these embodiments maintain direct contact between the ultrasonic source and the target tissue via the protrusions, and possibly also the peripheral structure. The longitudinally directed ultrasonic waves are conducted by the protrusions and the fluid between. The protrusions act by facilitating the transport of drugs toward the target tissue. Waveform interference from fluid in adjacent spaces between protrusions is minimised by the presence of the protrusions, which serve to at least block propagation of waveforms.

Another group of new embodiments present a hybrid device, having at least one region having multiple micron-scale protrusions and at least one other region having micro channels surrounded by rigid walls. Typically a region or regions having micro channels surrounded by rigid walls will form part of a peripheral structure bounding a region that has micron-scale protrusions.

Molecules that are known to the inventors to possibly be delivered to the body using sonophoresis include 1) molecules having any kind of electric charge or have a neutral (including overall neutral) electrical charge and 2) small or large molecules (including monoclonal antibodies of approximately 150,000 Daltons) and 3) molecules that are hydrophilic or hydrophobic or lipophilic.

Several exemplary embodiments of the various aspects of the invention are described with reference to an exemplary applicator device for delivering an agent non-invasively to a target tissue surface site via a transportation modality, which preferably uses only ultrasonic waves. In these exemplary embodiments, at the target tissue surface site, penetration of the agent into the target tissue surface site is enabled or enhanced through sonophoretic mechanisms. Preferably, target tissue surface sites are mucous membranes including, but not limited to, conjunctival, vaginal, urethral, inner ear, tracheal and bronchial mucosa, anal, oral, and nasal tissues. A target tissue surface can also include the cornea.

2. GENERAL PRINCIPLES AND MICRO-CHANNEL EMBODIMENTS

The system comprises an applicator device that is preferably hand-held and used for delivering an agent to a target tissue. The preferred form of applicator device includes a handle coupled to an applicator tip. The applicator tip includes an agent carrier body that has micro channels formed in it through which the agent is delivered from within the applicator tip to a target tissue surface. The agent carrier body may be integrated within the applicator tip, or may be a separate component (such as a cartridge) that is attachable to the applicator tip.

The applicator tip may include a reservoir that holds an agent. The reservoir may form part of the agent carrier body, or may be a separate component that is in fluid communication with the agent carrier body.

An ultrasonic transducer forming part of the handle or applicator tip generates ultrasonic energy (waves) which causes the agent to be moved through the micro channels in the agent carrier body, egress through terminal pores of the micro channels at a tissue contacting surface of the agent carrier body and onto the target tissue surface. The ultrasonic waves also enhance and/or permit agent uptake into the target tissue through sonophoresis.

FIG. 1A is a highly schematic diagram illustrating a first embodiment of an applicator device according to the present invention that is useable with any agent carrier or agent carrier body described herein. In this example, an applicator device 100 includes an applicator tip 102 coupled to an applicator handle 103 (entire device not shown). The applicator handle 103 includes an ultrasonic generator 101. The applicator tip 102 is connected to the handle 103 so that ultrasonic energy from the transducer 101 is transmitted to it via a coupling rod 106. As will be appreciated the application of ultrasound will be generally in accordance with the parameters set out in the overview above. The tissue contact surface of the applicator tip 102 is brought into contact with a target tissue surface 108. The ultrasonic generator is then activated, which results in the propagation of ultrasonic waves 110 via the coupling rod 106, through the applicator tip 102 and the agent carrier body 104 and into the target tissue 108. In this embodiment, agent is stored in the agent carrier body 104 and is transported to the target tissue surface 108 via micro channels 112 that have been fabricated within the agent carrier body 104. Ultrasonic waves assist in the transport of agent from the agent carrier body 104 to the target tissue surface 108 via the micro channels 112. Ultrasonic waves also enhance and/or permit the penetration of the agent into the target tissue 108 via sonophoretic effects on tissue ultrastructure.

Figure 1B:
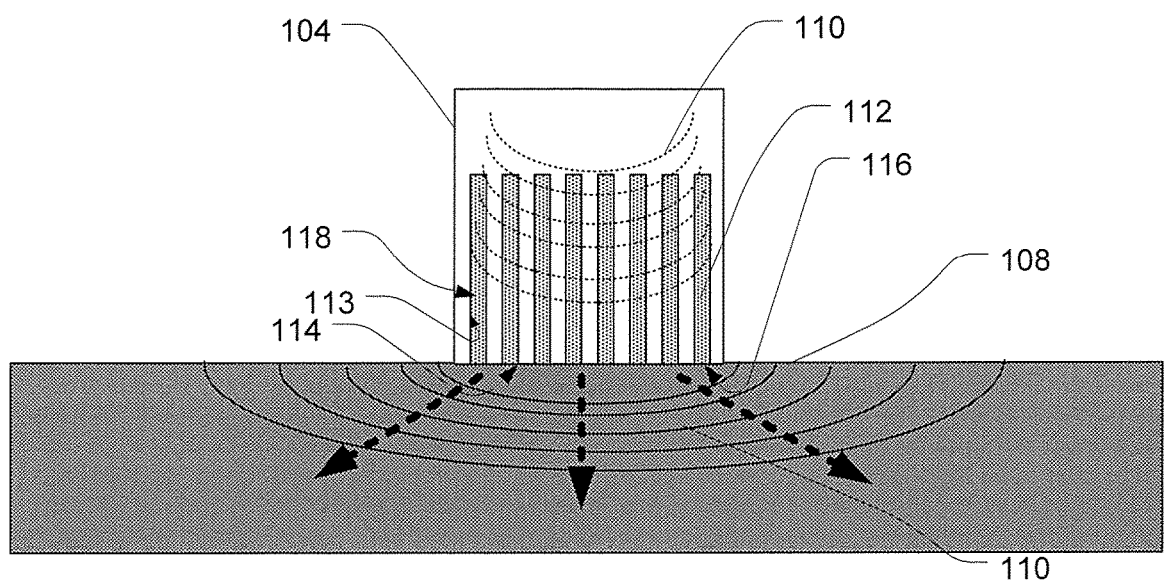
FIG. 1B shows a more detailed cross sectional view of the agent carrier body of the embodiment shown in FIG. 1A and previously described in the Applicant's Australian patent application 2013901606.

In this example, the agent carrier body 104 may be of any type described generally herein, and as exemplified in any one of FIG. 8A to 10 or 23 to 30A. However, to illustrate the principle of operation of an agent carrier body FIG. 1B provides a more detailed view of an agent carrier body 104 of the type previously described in the Applicant's Australian patent application 2013901606, 1A applied to the tissue surface 108. The agent carrier body 104 has a tissue-contacting surface 114. In this example it includes with micro channels 112 fabricated within the agent carrier body 104 that extend from within the interior of the agent carrier body 104 to the tissue-contacting surface 114. The micro channels 112 terminate as pores 116 at the tissue-contacting surface 114. Agent is provided from the agent carrier body 104, through the channels 112 where it egresses through the pores 116 in the tissue-contacting surface 114, and on to the tissue surface 108. As an alternative the agent carrier body 104 may be of any type described generally herein, and as exemplified in any one of FIG. 8A to 10 or 23 to 30A.

In this example, ultrasound 110 is generated and conducted through the agent carrier body 104. This causes agent 118 stored within the channels 112 to be released from the channels 112 and on to the tissue surface 108. The penetration of agent into the tissue 108 is enhanced and/or permitted by the use of ultrasound, which provides a sonophoretic effect on the tissue.

Figure 1C:
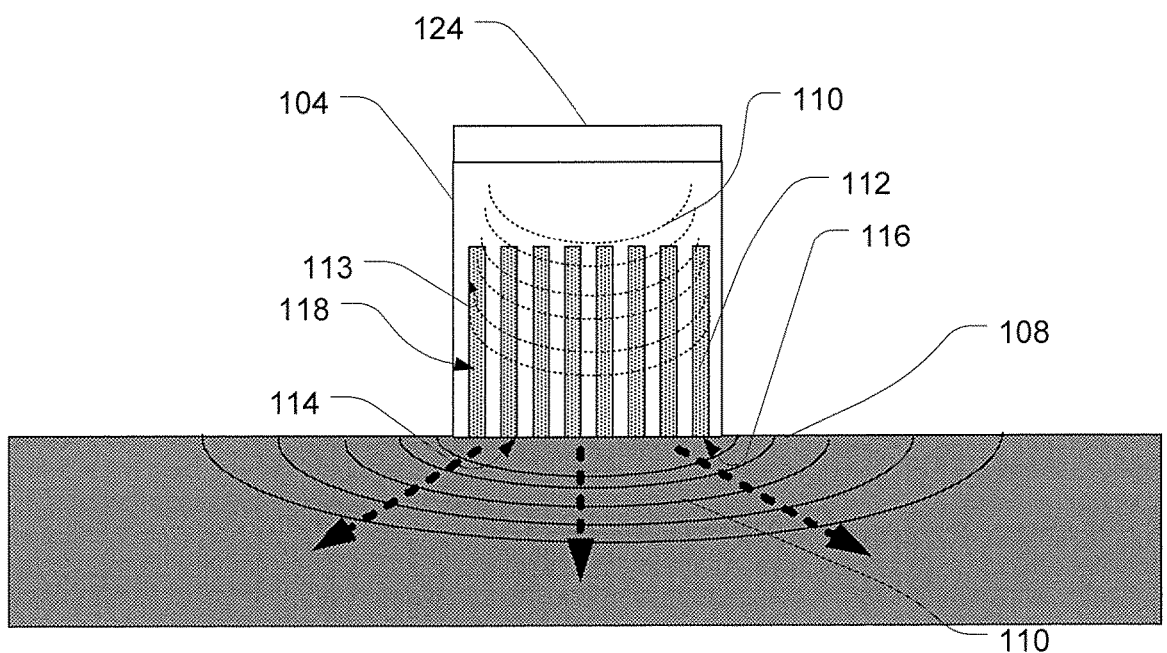
FIG. 1C shows a similar agent carrier body to that of FIG. 1B that includes an ultrasonic transducer.

In the embodiment of FIG. 1A, the applicator handle 103 has an ultrasonic transducer 101, which generates ultrasonic waves 110 that are transmitted through the applicator tip 102 to the agent carrier body 104 via the coupling rod 106. However, in alternative embodiments the applicator tip 102 can be fabricated to include within its structure, a system that is capable of generating ultrasonic waves itself without the need for an external ultrasonic transducer. FIG. 1C illustrates an alternative embodiment in which the agent carrier body 104 additionally includes an ultrasonic transducer 124.

It is preferred that the inner surface(s) of the channel 112 are functionalised. The inner surface 113 of the channels 112 may be functionalised with compounds or molecules having hydrophobic or hydrophilic properties or a combination of both moieties. Alternatively, the surface 113 of the channels 112 may be functionalised by contacting the surface of the channels with small molecules that are adsorbed to the surface of the channels, exposing specific functional groups that have the desired physical and/or chemical properties. The small molecules may be adsorbed through chemisorption or physisorption to the internal surface of the channels. Alternatively, or in addition to changing the water/oil affinity, the inner surfaces of the micro-channels and/or agent reservoirs may be functionalised by enabling them to become electro-conductive.

Alternatively, the surface 113 of the channels 112 may be functionalised by contacting the surface of the channels with small molecules that are adsorbed to the surface of the channels, exposing specific functional groups that have the desired physical and/or chemical properties. The small molecules may be adsorbed through chemisorption or physisorption to the internal surface of the channels. Alternatively, or in addition to changing the water/oil affinity, the inner surfaces of the micro-channels and/or agent reservoirs may be functionalised by enabling them to become electro-conductive.

Figure 2:
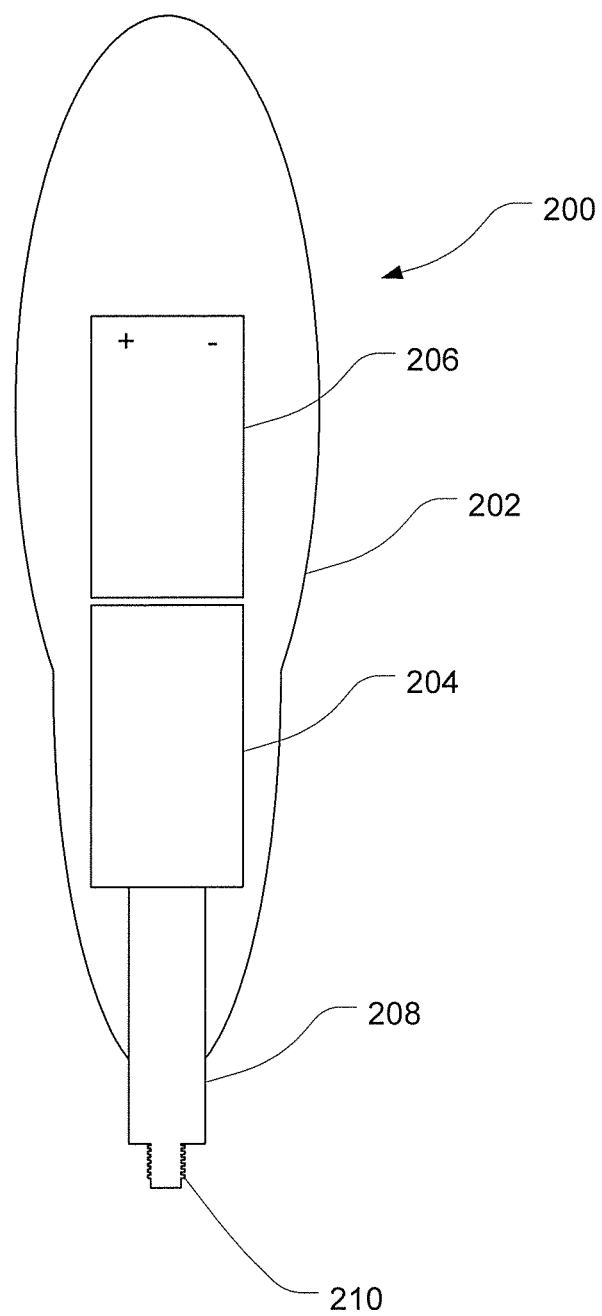
FIG. 2 provides a cross sectional block diagram of an embodiment of a handle assembly of the applicator device and its basic component parts.

FIG. 2 provides an illustration of an embodiment of the handle assembly 200 of an applicator device, usable with an agent carrier body of any type described generally herein, and as exemplified in any one of FIG. 8A to 10 or 23 to 30A. The handle assembly 200 includes a main housing 202, which contains an ultrasonic transducer 204. The transducer is powered by a battery 206 (or alternatively by an external power supply) and is configured to generate ultrasonic waves and transmit them to a coupling rod 208 that terminates in a connector 210. The connector 210 can be of any type for example a screw thread or bayonet fitting or the like, that enables the handle assembly 200 to engage with an agent carrier (through either direct or indirect engagement).

Figure 3:
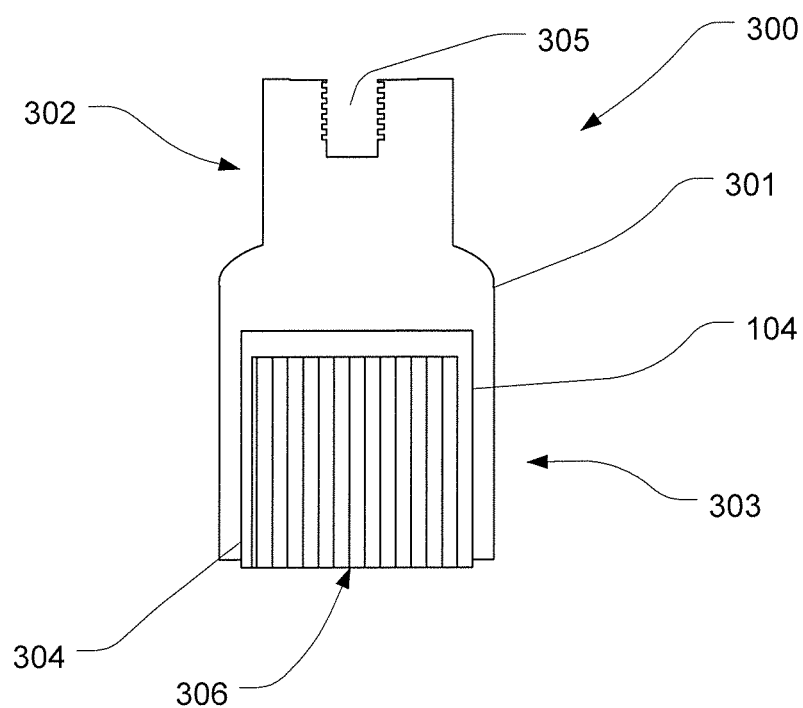
FIG. 3 is a cross sectional view through an agent carrier that takes the form of a single use applicator tip including an agent carrier body of the type previously described in the Applicant's Australian patent application 2013901606. As will be appreciated, any agent carrier body as generally described herein, and as exemplified in any one of FIG. 8A to 10 or 23 to 30A may be used as an alternative.

FIG. 3 is a schematic cross section of an applicator tip 300 that may be used with the handle assembly 200 of FIG. 2. The applicator tip 300 includes a housing 301 having a first end 302 and a second end 303. The first end 302 includes a mounting mechanism 305 such as a bayonet fitting or screw thread or the like, that makes a mechanical connection with a connector 210 of the handle assembly 200. The applicator tip 300 further includes a recess 304 at its second end 303 that is arranged to accept the agent carrier body 104 or an agent carrier body of any type described generally herein, and as exemplified in any one of FIG. 8A to 10 or 23 to 30A. The applicator tip 300 is configured, in use, to carry agent to the tissue-contacting surface 306 of the agent carrier body 104 and deliver it as required to tissue being treated by application of ultrasonic waves. In some embodiments the applicator tip 300 can include an agent reservoir, which is fluidically in contact with the micro channels formed in the agent carrier body 104.

FIGS. 4A, 4B, 4C, and 4D provide illustrations of various embodiments of single layer agent carrier bodies, and FIGS. 4E, 4F, 4G, 4H provide illustrations of various embodiments where an agent carrier body is created from stacked agent carrier layers.

The agent carrier body 400 is formed of a layer(s) of solid material and possesses a number or network of micro channels that may be a variety of geometric shapes and sizes. These micro channels can be used to store or retain an agent and also to deliver agent from within the agent carrier body 400 to a tissue-contacting surface 406 of the agent carrier body 400. The micro channels can be created by a micro-fabrication technique. For instance, in embodiments where the agent carrier body 400 is formed from silicon, the micro channels can be formed by lithography, etching and/or other processes. In embodiments made from metal, plastics or polymers the micro channels can be created by other techniques including the use of lasers of various types and wavelengths and molding and extrusion technologies. The use of these micro-fabrication techniques are particularly desirable as they provide the advantages of retained agent volume accuracy, the benefits of predicable micro-fluidics and further permits refinements such as specialised surface chemical treatment to either or both the exposed tissue-contacting surface and the internal walls lining the micron-scale cavities 402 of the agent carrier body 400. These benefits can be used, for example, to further enhance agent loading, retention and delivery to a target tissue.

The tissue-contacting surface 406 has a series of openings, fenestrations or pores 404. A wide variety of shapes and sizes of pores can be on the order of 10 to 100 μm, but other embodiments may have pore sizes up to 1000 μm. The micro channels 402 extend from the pores 404 in the tissue contact surface 406 at least partially through the agent carrier body 400. The micro channels 402 can be used for both retention of the agent and transportation of the agent to a tissue surface.

The pores 404 may have a patterned appearance and exhibit a range of geometries, for example: close packed hexagon structures, arrayed squares with assorted densities, mixed polygon mosaics, spirals, lines etc. The desired geometries are physically etched into the agent carrier body 400 so as to create arrays of micro channels 402 for retention and/or transport of an agent. The micro channels may be in a variety of shapes for example cylindrical, conical etc.

The walls of the micro channels 402 and/or other internal surfaces within the agent carrier body 400 may be treated such that: they have hydrophilic or hydrophobic characteristics that may be the same or opposite in nature to each other and/or the areas between the pores 404 of the tissue-contacting surface 406. The walls of the micro channels 402 and/or other internal surfaces within the agent carrier body 400 may be treated such that they conduct electric charge or can generate a local electric field that may have the same or opposite polarity to each other and/or the areas between the pores 404 of tissue contacting surface 406.

The agent carrier body 400 can be formed from a unitary piece of material. However, in alternative embodiments the agent carrier body may include a number of layers that are stacked. The use of micro-fabricated solid material as single or multiple layers to create an agent carrier body allows for improved acoustic transmission and thus improved delivery of agent to a target tissue site by ultrasound.

The dimensions and internal lining characteristics of the micro channels 402 and/or other internal surfaces within the agent carrier body 404, and the dimensions and number of layers comprising the agent carrier, will be tailored to suit the agent and the target tissues, and will vary as a consequence of agent properties, dose and formulation requirements, ultrasonic power and heat generation, and the duration of use.

FIG. 4B shows another embodiment, similar to that of FIG. 4A, except that the micro channels 402' are interconnected by internal linking channels 408. Such a structure provides some level of agent storage in addition to channels 402' alone.

FIG. 4C represents a further embodiment in which the single layer agent carrier body 400" has micro-channels 402" which terminate as pores 404" in the tissue-contacting surface 406" at one end of the micro-channels 402", and connect at their other end to an agent reservoir 410.

FIG. 4D provides surface views of a single layer agent carrier body shown in any one of FIGS. 4A to 4C. The agent carrier body 400" has a first surface 411 and a second surface 412 which is the tissue-contacting surface. As previously discussed, micro-channels extend from within the agent carrier body 400 (from a reservoir 410 or linking channel 408 if present) and terminate as pores 404 in the tissue-contacting surface 412.

In alternative embodiments, the agent carrier body has a stacked layer structure and includes at least two layers. More preferably, one or more layers have additional micro-reservoir volumes formed within them and which are in fluid communication with the micro-channels for holding agent prior to application to the tissues being treated. The micro-reservoir volume may be a single volume or a plurality of small volumes, e.g. each of which is contiguous with one or a group of micro-channels. There may be a single large reservoir volume in the layer furthest from the tissue-contacting layer that is fluidically connected with the channels. Alternatively, there may be multiple micro-reservoir volumes, with each of the micro-reservoir volumes being in fluid communication.

FIGS. 4E, 4F, and 4G correspond with FIGS. 4A, 4B, and 4C respectively, except that the agent carrier body 413 includes a first layer 414, 414', 414" and second layer 416, 416', 416". The first layer 414, 414', 414" is as generally described with respect to the single layer embodiment of FIGS. 4A, 4B, and 4C, except instead of having a tissue contacting surface 422, the first layer has an interface surface 415 including pores or blind holes that defines a portion of the micro channels that extend through the first and second layers when the layers are stacked together. The second layer 416, 416', 416" includes a first surface 420 that contacts the interface surface 415 of the first layer 414, 414', 414" and a tissue-contacting surface 422 having pores 426 that are formed by micro channels 424. As can be seen the micro channels 424 extend from within the first layer, through the second layer 416, 416', 416", and terminate at the tissue-contacting surface 422 of the second layer 416, 416', 416" as pores 426. In this way, the holes in the first layer 414, 414', 414" and second layer 416, 416', 416" are aligned to form the micro channels 424 so that the first layer 414, 414', 414" and second layer 416, 416', 416" are connected permitting fluid continuity in the system.

FIG. 4H illustrates a further alternative embodiment of a double stacked layer agent carrier body 413 in which the first layer 414'" contains an open-ended agent reservoir 425 that provides agent directly into the micro-channels of the second layer 416'".

FIG. 4I provides surface views of the various layers of a double layered agent 413" carrier shown in FIG. 4H. The first layer 414" has a first surface 430 and a second surface 432. The second layer 416" has a first surface and a second surface (which are the same and are generally represented as 434). The agent reservoir 425, is formed by a recess formed in first layer 414" that extends partially into it. The second surface 432 of the first layer 414" is aligned and placed over the interface surface of the second layer 416" such that substantially all of the micro-channels 424 formed in the second layer are fluidically connected with the agent reservoir 425 in the first layer 414".

Figure 4A:
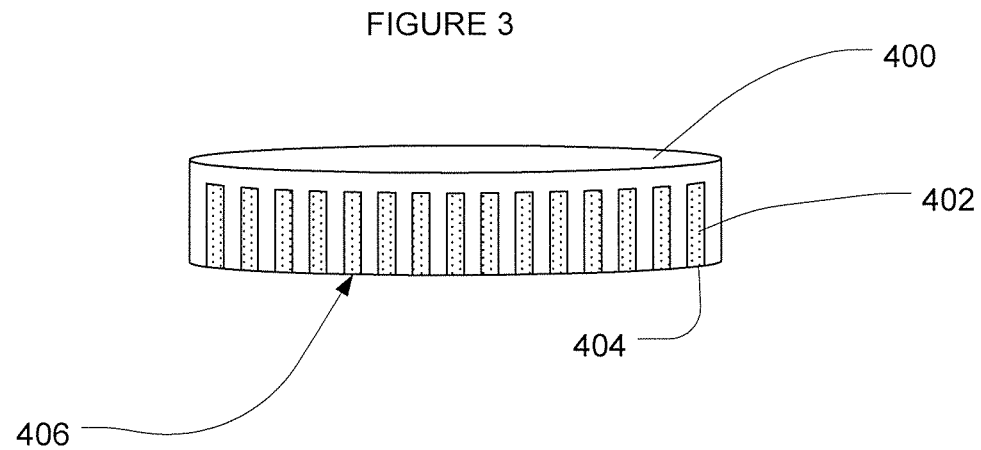
FIGS. 4A, 4B, and 4C provide illustrations of various embodiments of a single layer agent carrier body with different micro-channel, and or reservoir arrangements previously described in the Applicant's Australian patent application 2013901606.
Figure 4B:
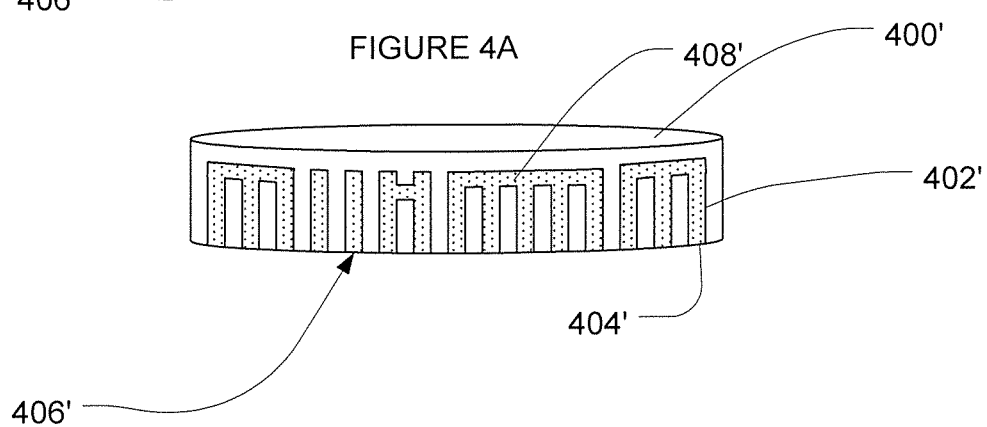
Figure 4C:
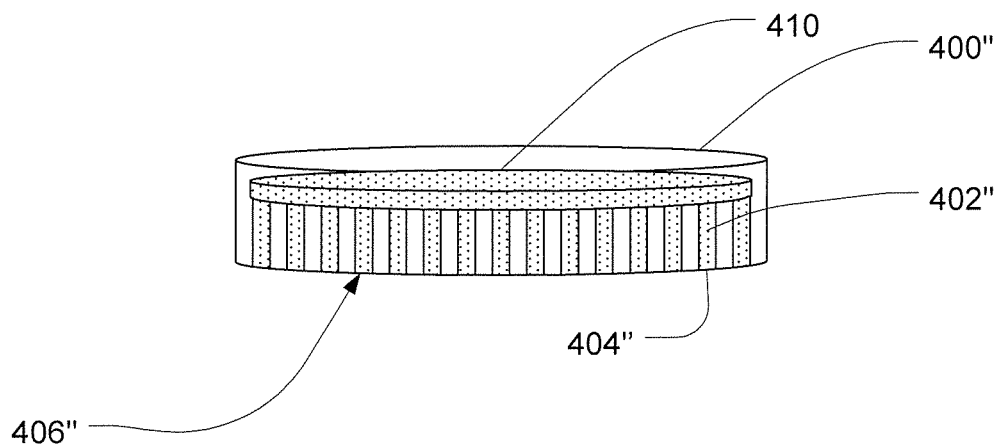
Figure 4D:
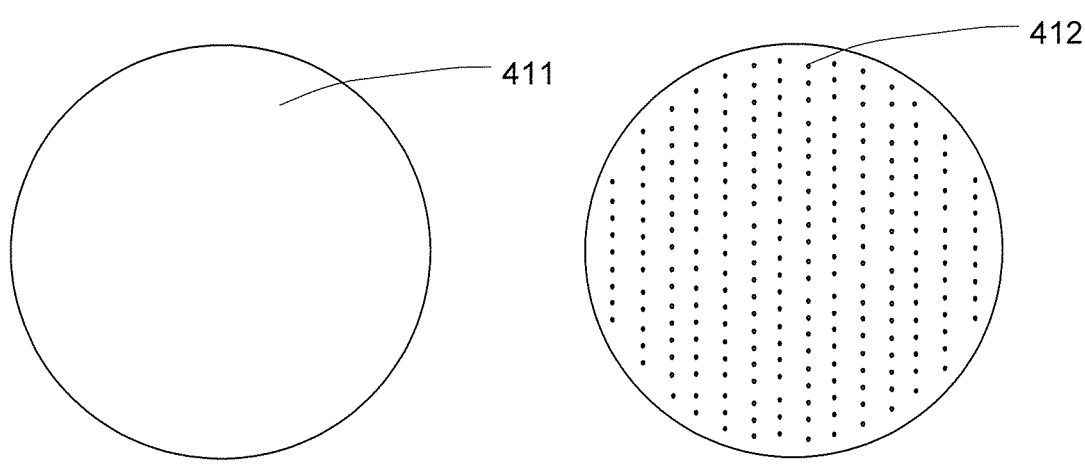
FIG. 4D provides an illustration of an embodiment of a first surface and a tissue contact surface of a single layer agent carrier body.
Figure 4E:
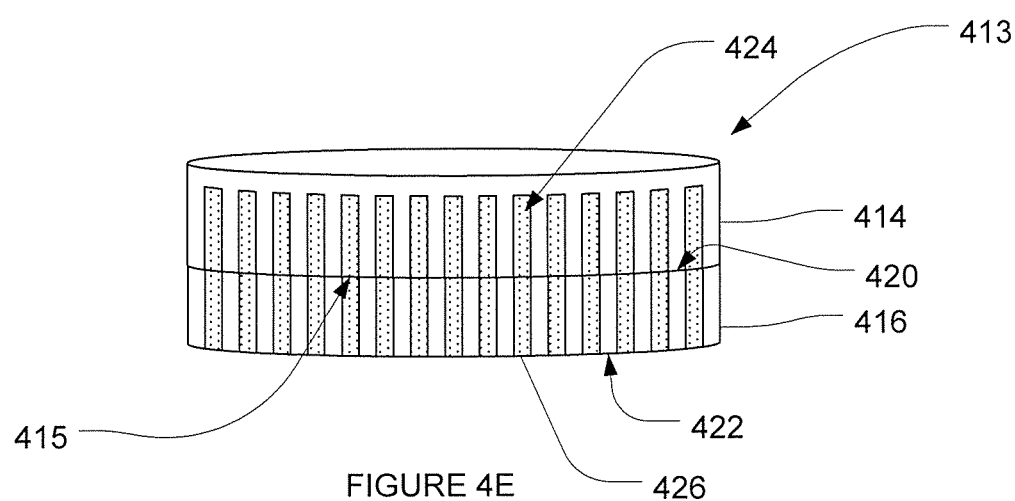
FIGS. 4E, 4F, 4G, and 4H provide illustrations of various embodiments of a multiple layer agent carrier body with different micro-channel and reservoir arrangements.
Figure 4F:
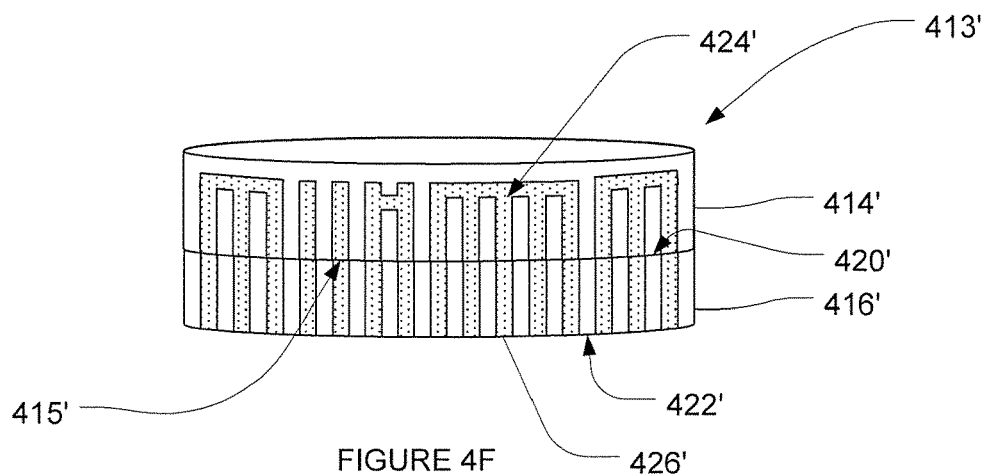
Figure 4G:
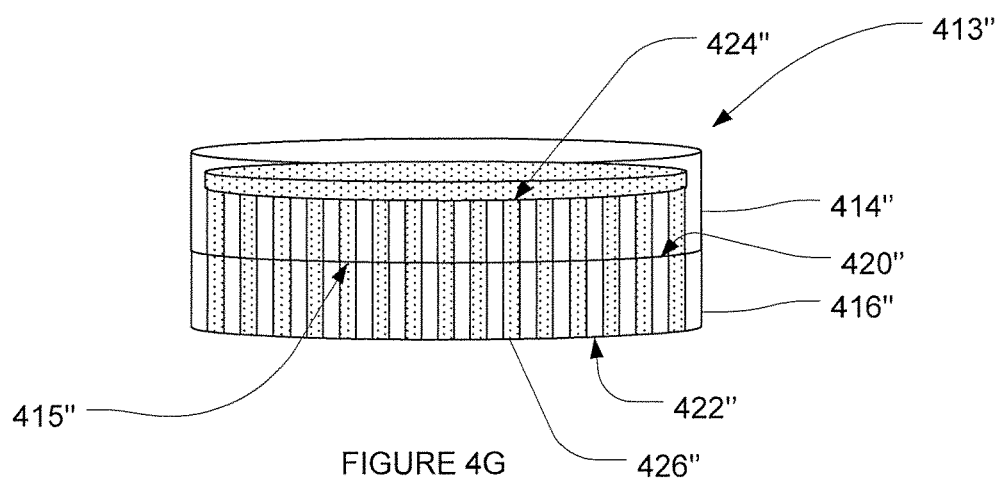
Figure 4H:
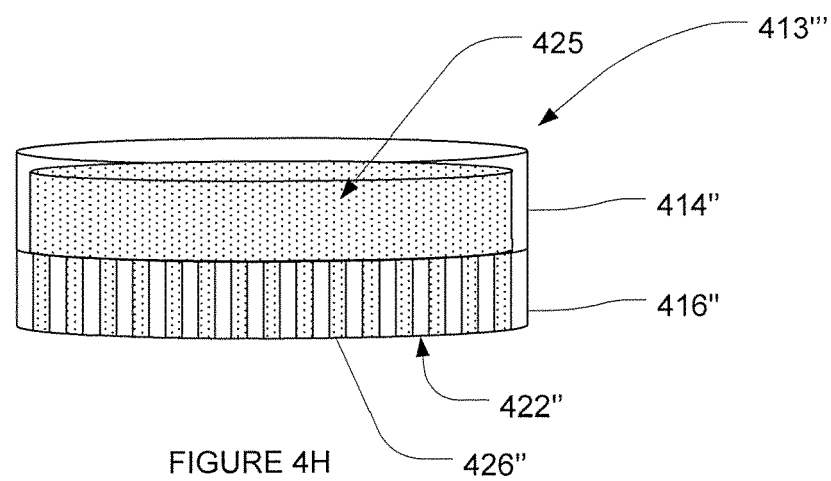
Figure 4I:
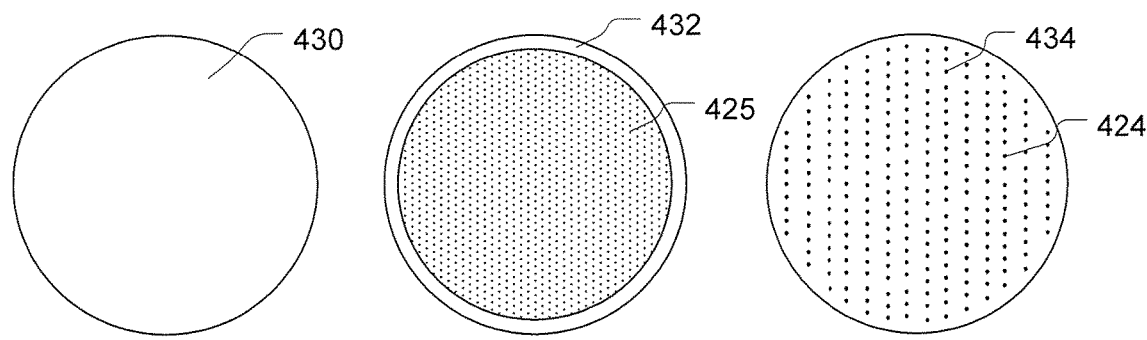
FIG. 4I provides an illustration of the embodiment shown in FIG. 4H of a first surface and a second surface of a first layer of the agent carrier body, and a first surface and a tissue contact surface of the second layer of the agent carrier body.
Figure 4J:
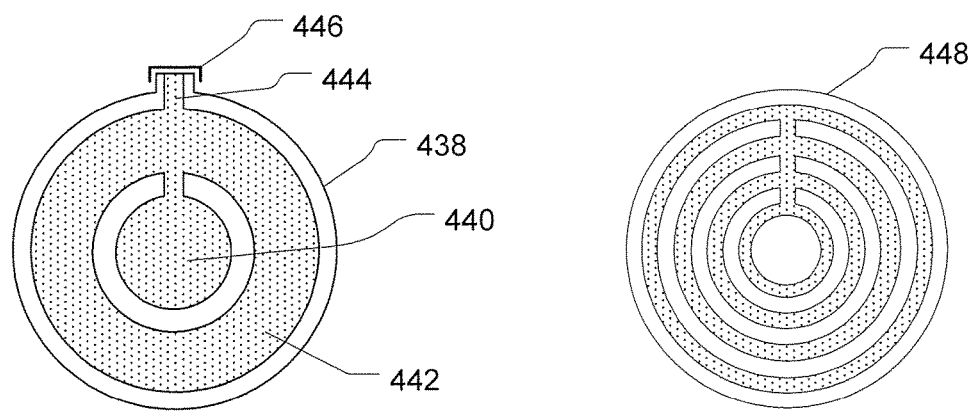
FIG. 4J provides illustrations of further example embodiments of agent reservoir contacting layer of an agent carrier body that can store additional agent and replenish the micro-channels as they are depleted of agent during the course of usage.
Figure 5A:
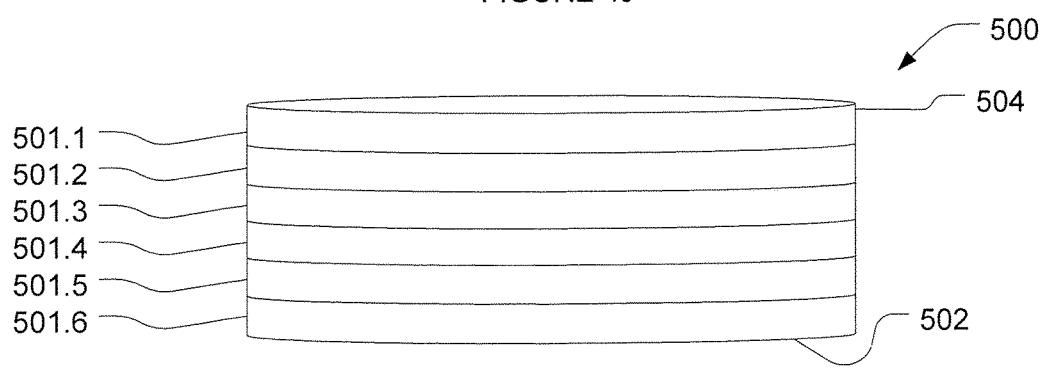
FIGS. 5A, 5B and 5C provide illustrations of various embodiments of the agent carrier body each of which has a differently configured surface contact layer.
Figure 5B:
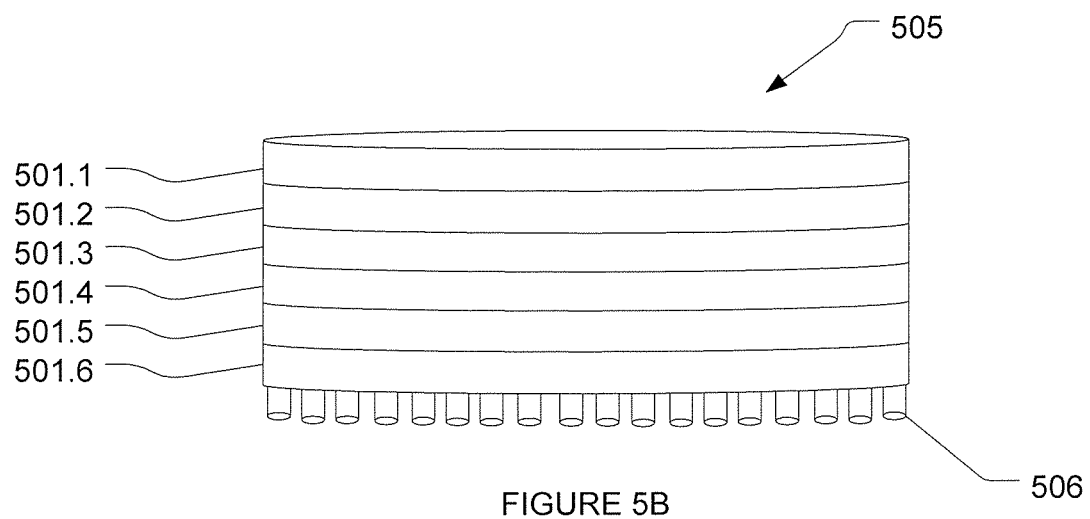
Figure 5C:
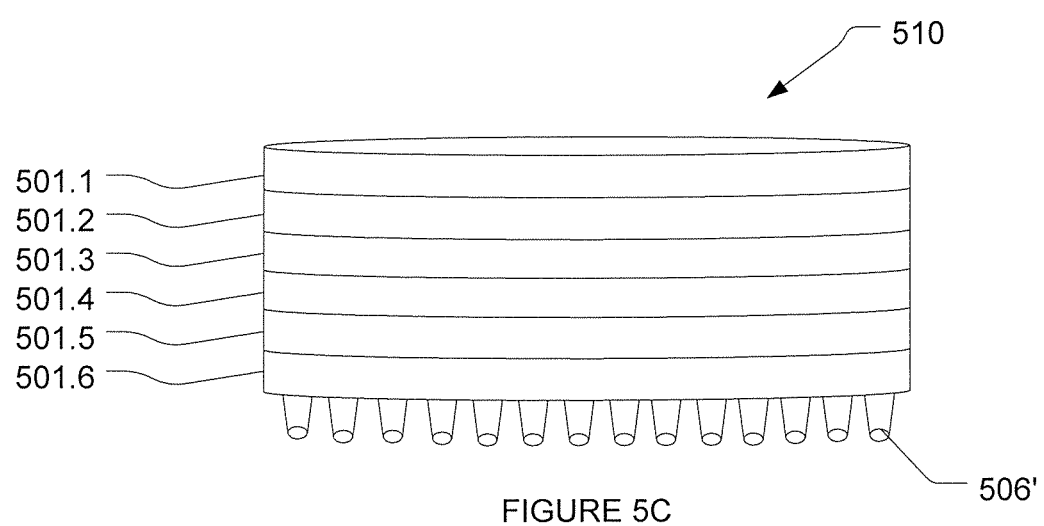
Figure 5D:
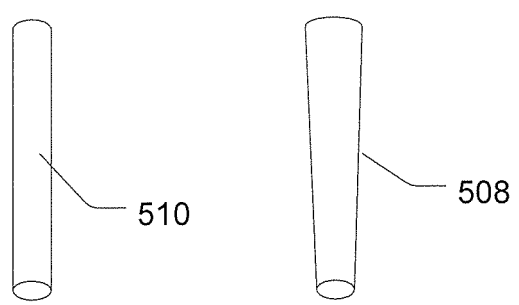
FIG. 5D provides an illustration of two exemplary types of micro-protrusions that extend from the agent carriers shown in FIGS. 5B and 5C.
Figure 6:
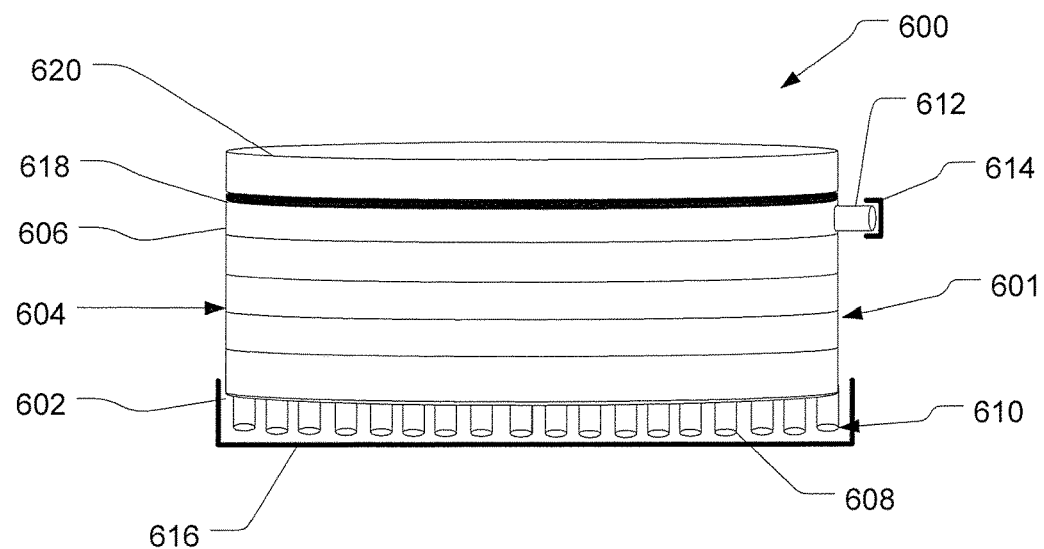
FIG. 6 provides an illustration of an embodiment of an agent carrier body having a stacked layer arrangement and an agent filling port.

FIG. 4J provides illustrations of further embodiments of agent reservoirs formed in an agent carrier body that can store additional agent and replenish the micro-channels as they are depleted of agent during the course of usage. The reservoirs may connect to micro-channels in the same agent carrier body layer as shown for example in FIG. 4G or connect to micro-channels in a contiguous layer in the agent carrier body as shown for example in FIG. 4H. Agent carrier body 438 includes a reservoir formed by two annular ring shaped reservoir volumes 440 and 442 and includes a conduit 444 extending through a port 446. When a vacuum is applied to the port 446, or the port 446 is injected with agent, a negative pressure or a positive pressure respectively is applied to the reservoir 440, 442. A layer of this type is arranged in a stack of layers to form the agent carrier body, the first layer overlies its adjacent layer such that any holes in the adjacent layer fluidically connect to the reservoir volumes to allow agent to travel via micro channels through the layers and to the tissue-contacting surface.

Agent carrier body 448 is another embodiment in which the reservoir consists of a number of concentric rings each fluidically connected to each other. It will be appreciated that other arrangements of the agent reservoir volumes within a layer are possible without departing from the invention.

Generally, the holes in a lower or intermediate layer of an agent carrier body extend through the whole thickness of that layer and in combination with subsequent fluidically connected holes in other layers, form a micro channel that extends from the tissue-contacting surface in the surface contact layer of the agent carrier. It will be appreciated that in certain instances the holes only extend partway into a particular layer; this can be the case for the first layer as illustrated for example in FIGS. 4E-4G.

As stated previously, it is preferred that the inner surface(s) of the micro channels and other internal surfaces of the agent carrier, such as those of the agent reservoirs, may be functionalised.

In the embodiments illustrated in FIGS. 5A, 5B and 5C the agent carrier body includes six layers including a surface tissue-contact layer and five layers stacked on top of one another overlying the surface contact layer.

FIG. 5A shows an embodiment of an agent carrier body 500 having six stacked layers 501.1, 501.2, 501.3, 501.4, 501.5, 501.6 The first end of the agent carrier body is a surface tissue-contact surface 502 on layer 501.6 that contacts the tissues being treated. On top of this layer there are a plurality of additional layers and a top most layer 501.1. In this embodiment the agent reservoirs and micro channels for holding and delivering agent (not shown) may extend through some or all of the layers 501.1-501.6 of the agent carrier 500. In some embodiments, the channels extend from the tissue-contact surface 502 in layer 501.6, through intermediate layers 501.5 to 501.2, and terminate in the top-most layer 501.1.

FIG. 5B shows an alternative embodiment of a six stacked layer agent carrier body 505 to that shown in FIG. 5A. In this embodiment, the surface tissue-contact layer 501.6 includes a number of micro-protrusions 506, which in this example are micro-tubules. FIG. 5C shows a further alternative agent carrier body 510 having a similar overall arrangement but in which the micro-protrusions 506' are micro-needles. The micro-protrusions are hollow, and included channels formed therein that form a part of the system of minor channels for delivering the agent.

Micro protrusions, such as micro-needles and microtubules can be created by secondary fabrication consisting of etching the tissue contact surface 502 of a tissue-contacting layer 501.6 such that the areas between the pores are largely removed. This leaves a wall around each pore of the required protrusion to surround each pore. The micro-needles and microtubules can be of any shape desired. For example, FIG. 5D shows the micro-protrusions as having a cylindrical shape (micro-tubules 510) and other micro-protrusions as having a frustoconical shape (micro-needles 508). In other embodiments, not illustrated, the surface 502 tissue contact layer 501.6 can be provided with other surface treatments, or surface engaging structures, such as a saw tooth structure, ripples, rings or the like to help the agent carrier body interface with the target tissue.

In a preferred embodiment each layer is disc shaped or cylindrical in shape. Preferably the layers have a thickness of from about 0.3 mm to about 1.0 mm, and even more preferably each layer has a thickness of about 0.5 mm. It is preferred that each layer has a diameter of from about 3 mm to about 10 mm, and even more preferably has a diameter of about 5 mm. The thickness dimension and the diameter dimension may vary between layers. While the layers and overall shape of the agent carrier body have been described as being disc shaped or cylindrical in cross sectional shape, as in FIG. 3, other shapes could be employed without departing from the ambit of the invention, e.g. rectangular, square, or other polygon, oval etc. Furthermore, while it is preferred that the overall shape of the agent carrier body is of constant cross section the overall shape of agent carrier body could change along its length e.g. the agent carrier body could be shaped as a frustum (whether conical or otherwise pyramidal), or a prism etc. The overall shape and/or the shape of components of the agent carrier and the agent carrier body can modified in order to maximise the efficiency of the device which is dependent on the transportation modality or combination of transportation modalities employed.

FIG. 6 provides an illustration of an agent carrier 600 having an agent carrier body 601 with stacked arrangement. The stack includes a bottom most layer 602, four intermediate layers 604, a top most layer 606. The bottom most layer 602 has micro-tubules 608 extending to form the tissue-contact surface 610. The agent carrier 600 additionally includes a port 612. In this embodiment the port 612 is part of the first layer 606. The port 612 is connected with micro-channels formed in the agent carrier body 601, preferably via an agent reservoir volume in the first layer 606 so that fluid can flow between them. The port 612 is configured to connect to a vacuum line or pressure injector so that a negative or positive pressure respectively can be applied to the port 612. This allows the agent to be loaded into the agent carrier from an external source. On application of a vacuum to the port 612, agent is drawn through the pores in the microtubules in the tissue contact surface 610, through micro-channels into the stack of layers of the agent carrier body 601 to fill the micro channels and the reservoir volumes. Alternatively, agent can be injected into the agent carrier via the port 612. Using either method, the agent carrier can be charged with an agent.

FIG. 6 also shows a closure or seal 614 applied to the port 612, and a closure or seal 616 applied over the surface contact layer 610. The seal 616 seals the surface of the surface contact layer 610 to maintain sterility and any vacuum that is created within the micro channels. Similarly, seal 614 seals the port 612 for similar purposes. It is preferred that this seal layer is a plastic film.

The embodiment of FIG. 6 also includes an additional layer 618 and an ultrasonic transducer 620. Layer 618 may be a simple insulation layer that serves to cover the fenestrations in the top layer (if the micro-channels extend the entire way through the top layer) to prevent the egress of fluids and/or to prevent release of a contained vacuum.

The transportation modality may use an electric field to cause a charged agent to be transported. The electric field can be provided by applying a voltage to an electrode in the agent carrier using an internal battery in the applicator device or by an external power supply. In a preferred form an electrode is located within the applicator device, a second external electrode, also connected to the applicator device power supply, can be located in such a way that the target tissue effectively becomes an electrode opposite in polarity to that of the internal electrode. The polarity of the electrodes can be selected such that the internal electrode is of the same polarity as the electric charge on the agent. The voltage established between the two electrodes transports an electrically charged agent through the agent carrier to the tissue-contacting surface and can enhance and/or permit the transport of the charged agent into the tissue via iontophoresis. Embodiments of the invention can use multiple delivery modalities using ultrasonic waves and electric current used in combination either alternately or simultaneously. Accordingly, Layer 618 can additionally be modified to include, or alternatively be, a material that serves as an electrode. The electrode can be positively or negatively charged and is used to generate a static or dynamic electric field. In the case where the top surface of the adjacent agent carrier layer does not have pores and the adjacent agent carrier layer is made from a material that is not electro-conductive, there is no direct contact between the electrode and the ions or charged agents contained within the micro channels or reservoirs however, ions and charged agents of the same polarity as that existing on the electrode will be repelled. If the adjacent agent carrier layer is made from a material that is electro-conductive and the adjacent agent carrier layer does not have holes, there is electrical conductivity established with the ions or charged agents contained within the micro channels or reservoirs. This scenario is functionally equivalent to the case where the surface of the adjacent agent carrier layer does have pores (and is not dependent on the electro-conductivity of the adjacent agent carrier layer) and the electrode is in direct contact with the ions or charged agents contained within the micro channels or reservoirs, where a further electrode, opposite in polarity to layer 618 can be placed on, or adjacent to, the target tissue. To complete the electric circuit, the electrode placed on or adjacent to the target tissue may be connected to the agent carrier; applicator handle; or other component of the application device (not shown). An applied voltage can provide the energy required to cause an electrically charged agent of the same polarity as the electrode of layer 618, to flow in the fluid contained in the micro channels of an agent carrier body 601 to migrate through the agent carrier, out of the pores to the tissue surface to be delivered into the tissue by iontophoresis.

This provides an alternative embodiment whereby the agent carrier is able to generate an electric voltage to facilitate the flow of an electric current to transport electrically charged agents through the agent carrier and out of the pores to the tissue.

In some embodiments the agent carrier body includes (as with layer 618), or is itself an electrode to facilitate the transport of a charged agent through the agent carrier and out of the pores to the target tissue. The electrode may be located adjacent to the stack of layers, or may be an electrode layer that is integrated within the stack of layers (as with layer 618).

In the above embodiment, ultrasonic energy and/or electrical voltage provide the energy required to move the agent through the agent carrier to its tissue contact surface where sonophoresis and/or iontophoresis enable the agent to be delivered into the target tissue.

As will be appreciated in the above embodiments, a layer including the tissue contacting surface e.g. 422, 422', 422" 502, 610 can be a layer including a tissue contacting surface being at least partly defined by a plurality of protrusions, such as those described in any one of FIGS. 8A to 10 and 23 to 28.

Figure 7A:
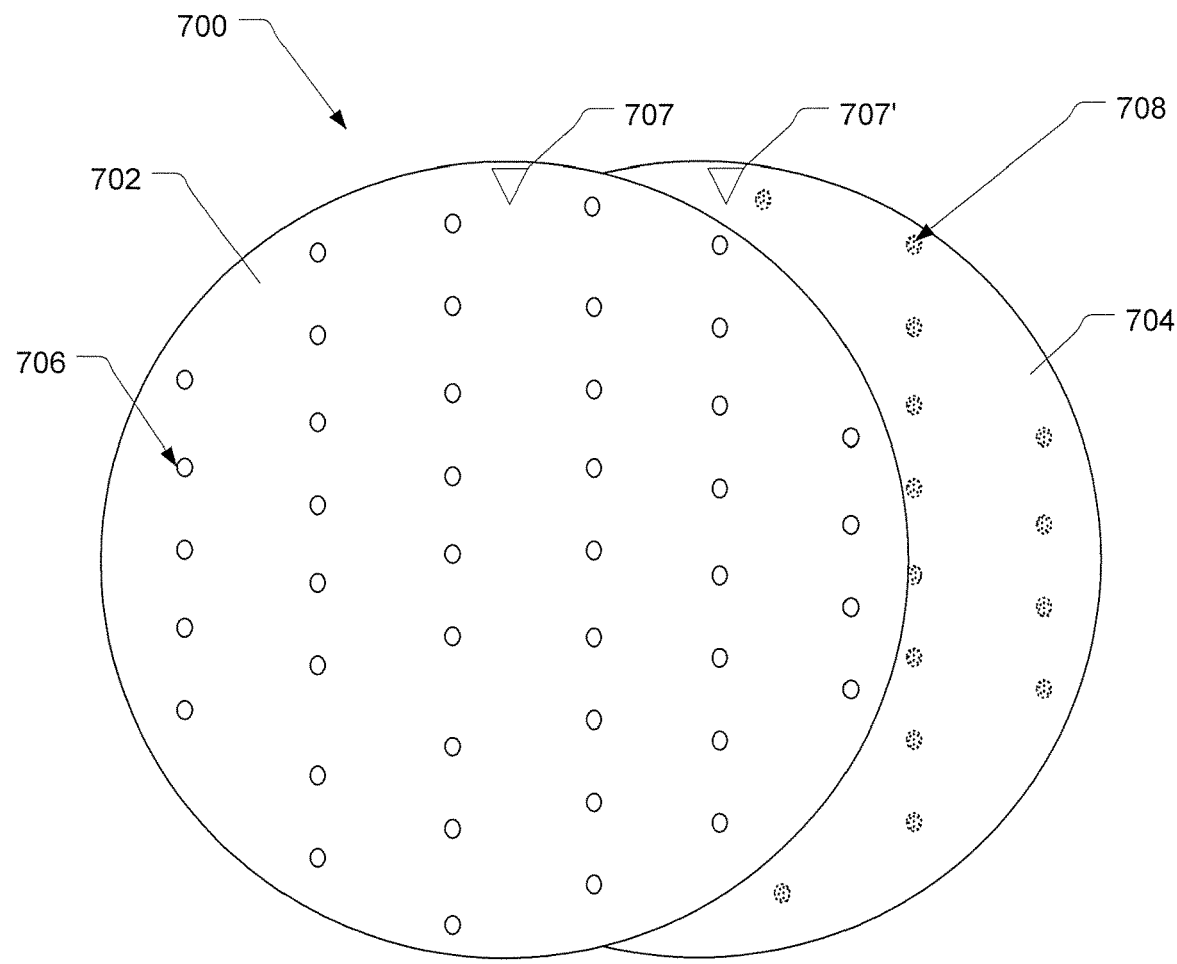
FIGS. 7A and 7B provide illustrations of embodiments of the holes, and the channels defined by the holes, in an agent carrier body that has a stacked layer structure.
Figure 7B:
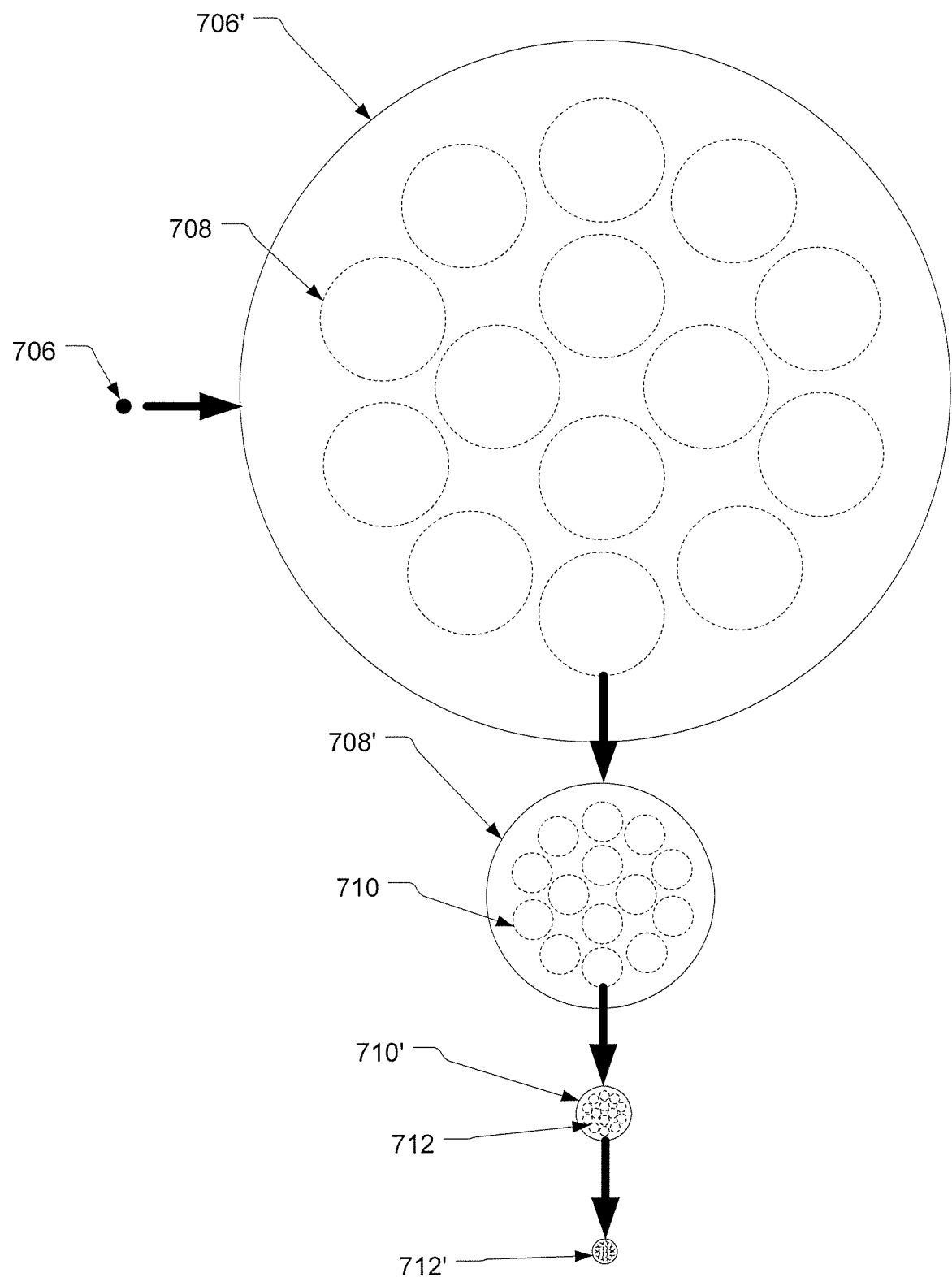

FIGS. 7A and 7B provide an illustration of an embodiment of the holes, and the channels defined by the holes, in a stack of layers forming the agent carrier body according to an embodiment of the present invention. FIG. 7A provides an illustration of a stack of layers 700 that includes two layers, 702 and 704. Layer 702 is a layer that is further from the tissue-contacting surface than layer 704. The layer 702 includes a plurality of holes 706; the layer 704 includes a plurality of holes arranged as a cluster of holes 708. These layers 704, 702 are arranged adjacent to each other in the stack of layers 700 such that each cluster of holes 708 in layer 704 is aligned with a hole 706 in layer 702. The holes in the layer 704 are more numerous and smaller than the holes in layer 702. To facilitate alignment in the layers during device fabrication each layer 702, 704 can be provided with a datum point or structure 707, 707' which define the alignment of the layer. Layers can then be aligned with their respective datum points 707, 707' arranged in a predetermined fashion (e.g. aligned with each other) to achieve correct alignment of holes in respective layers 702, 704, thereby forming micro-channels that extend through multiple layers of a stack 700.

FIG. 7B provides a further illustration of the variation and alignment between holes of different sizes in different stack layers of the agent carrier body. Hole 706' is a magnified version of hole 706. The hole 706' overlies a first cluster of holes 708 (shown in dotted lines) in the next adjacent stack layer. Hole 708' is a magnified version of hole 708. The hole 708' overlies a corresponding cluster of holes 710 (shown in dotted lines) in the next adjacent stack layer. Similarly Hole 710' is a magnified version of hole 710. The hole 710' overlies a corresponding cluster of holes 712 (shown in dotted lines) in the next adjacent stack layer. Hole 712' is a magnified version of hole 712 and so on until the final layer.

Multiple layers can be arranged such that progressing from the top most layer, through the intermediate layers, to the surface contact layer, the diameter of the holes decreases and the number of holes may be increased. Each subsequent layer includes a cluster of holes that is in alignment with a hole in the adjacent subsequent layer. For example, a first layer (which may be the top most layer or an upper one of the intermediate layers) has a number of holes. This first layer overlies a second layer, wherein the second layer has clusters of holes that are arranged beneath the holes in the first layer. This second layer may overlie a third layer and each hole in each of the cluster of holes in the second layer overlies a further cluster of smaller holes in the third layer (additional layers may also be provided in this manner).

The channels define a flow path for the agent through the agent carrier body to the tissue surface. The channels are defined initially by the diameter of the holes in the first hole possessing layer. Subsequent layers have clusters of holes that are aligned with the holes in this first hole possessing layer. Therefore, progressing from the first hole possessing layer through subsequent layers, the channels become multifurcated into numerous branches. It will be understood that these numerous branches all form a part of the channel.

Figure 7C:
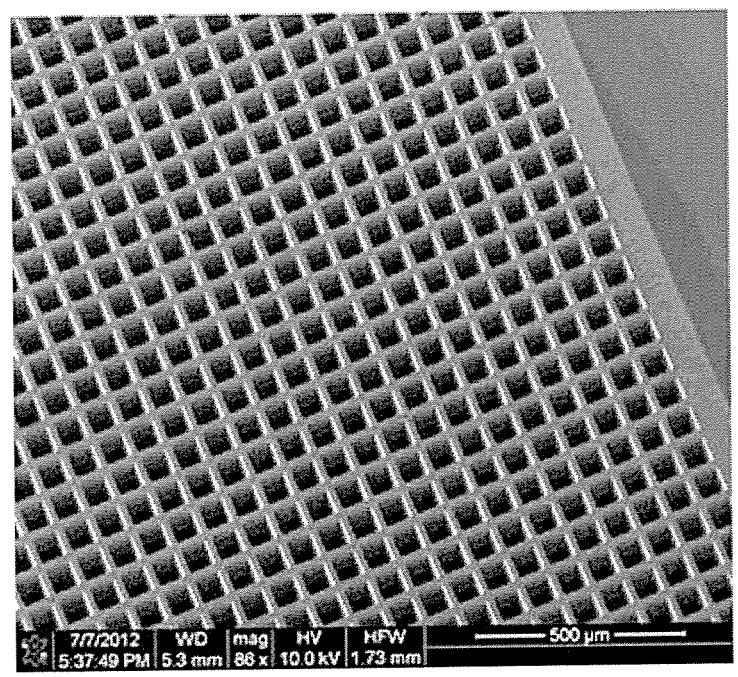
FIGS. 7C to 7E provides magnified images of the holes and micro-channels created by the micro-manufacturing process.
Figure 7D:
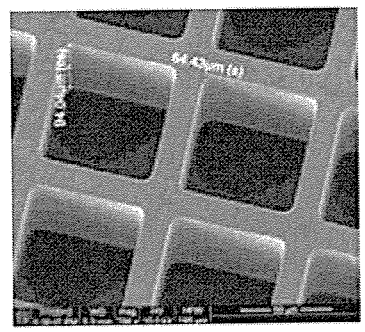
Figure 7E:
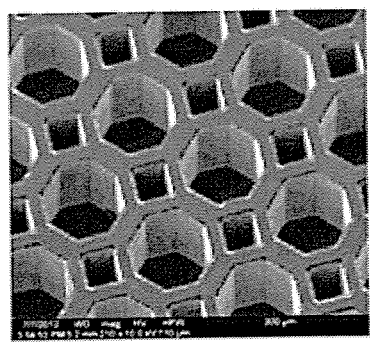

FIGS. 7C, 7D, and 7E show magnified images detailing examples of micro-channels created by a micro-manufacturing process. FIGS. 7C and 7D (7D showing a higher magnification of 7C) shows a layer in which the holes have square cross-sections. FIG. 7E shows a layer that includes holes having square and hexagonal cross-sections.

3. PROTRUSION-BASED EMBODIMENTS

The following series of embodiments include a plurality of microstructures formed from micron-scale protrusions that together define the tissue contacting surface of the agent carrier body. These micro-scale structures contact the target tissue and the agent to be delivered surrounds them. In preferred forms the agent carrier body has a peripheral structure, typically a wall, that surrounds the protrusions and contains the agent in use. This embodiment has a lower ratio of microstructures to fluid within the agent carrier body compared to an agent carrier body comprised of microchannels. Preferably these embodiments maintain direct contact between the ultrasonic source and the target tissue via the protrusions, and possibly also the peripheral structure. As will be appreciated the application of ultrasound will be generally in accordance with the parameters set out in the overview above.

More specifically FIGS. 8A to 10 and 23 to 30A illustrate several embodiments that employ an agent carrier body including a tissue contacting surface for engaging tissues under treatment, the tissue contacting surface being at least partly defined by a plurality of protrusions. The protrusions preferably extend outward from an inside of a void and terminate at said tissue contacting surface. The void may be formed by a peripheral structure, where at least part of said peripheral structure may terminate at the tissue contacting surface.

In some embodiments the peripheral structure terminates in a common plane with the protrusions. In others at least some of said protrusions defining the tissue contacting surface extend outward from the void beyond the peripheral structure. In some embodiments, the protrusions may terminate in a plane and the peripheral structure may terminate short of the plane such that the protrusions extend beyond the peripheral structure.

In such embodiments is should be noted that the protrusions of the preferred embodiments do not act as microneedles. Unlike microneedles, the protrusions of the preferred embodiments are not intended to penetrate any layer of tissue. The function of protrusions includes engaging the target tissue by applying pressure resulting in a frictional force on the surface. This aids the positioning of the device (e.g. on the slippery surface of mucous membranes) and enhances the sonophoretic effect.

As will be appreciated, the agent carrier bodies exemplified in these figures, can be used in place of any agent carrier body illustrated herein e.g. agent carrier body 104, 810, 902, 903, 903', 903", 903''', 903'''' and 1302, or with any of the agent carriers described herein, e.g. agent carriers 300, 800, 800' and 900, 900', 900", 900''', 900''''.

In the preferred embodiments, protrusions include the following properties:
 They do not have a needle-like tip, that is, they do not narrow to a point such that their width does not decrease to near zero at the tip.
 The cross-section is relatively constant, at least near their tip, and most preferably along their whole length. In most cases the width will not narrow by more than 20%, and preferably less than 10% towards its tip.
 they typically have a tip width greater than 10 µm. Thus the scale of the protrusions also differs generally from that of microneedles.
 They do not enter an intact epithelial surface of the target tissue.
 They aid in stabilizing the device by the frictional force they apply when the device is placed in contact with the tissue. This is particularly advantageous on mucous membranes that tend to have a low friction surface due to local mucous secretions.
 They generally have a height to width aspect ratio (across their shortest cross sectional width) of between 1:1 to 10:1. Whilst higher aspect ratios may be used it is difficult to achieve acceptable strength that they can withstand handling, loading and application of ultrasonic energy without damage. As will be appreciated cross sectional shape will greatly affect the strength of them and will be chosen accordingly.
 In preferred embodiments the protrusions occupy more than 5% of the volume surrounding them in which agent is carried. This percentage needs to be high enough so that the capillary force or other forces retain the agent within the agent carrier body against gravity or other forces caused by normal handling. In embodiments used with water-like agents, will typically have a density of projections of greater than 5% and most preferably greater than 10%. It should also be appreciated that as the agents become thicker, e.g. protein rich agents, the density of protrusions, or their size and/or wall surface area, can be lowered.

FIGS. 8A to 8G illustrate schematic representations of alternative embodiments of an agent carrier body and agent carrier body layers which include multiple protrusions that together define the tissue contacting surface of the agent carrier body.

In this embodiment the agent carrier body 750, can be used for delivery of an agent to a tissue via a transportation stimulus. The agent carrier body 750 includes a tissue contacting surface 752 for engaging tissues under treatment. In this example the tissue contacting surface is defined, at least partly by a plurality of protrusions 754.

The protrusions 754 may be of any shape, but in the present example are generally cylindrical. Preferably the protrusions have a constant cross sectional shape along their height. The protrusions 754 extend outward from an inside of a void 756 that is formed within the agent carrier body 750. The outward ends 758 at least partly define the define the tissue contacting surface of the agent carrier body 750, The void 756 is formed by a peripheral structure 760, which in this case takes the form or a peripheral wall or rim. The rim 760 also defines part of the tissue contacting surface 752.

The peripheral structure 760 in this embodiment terminates in a common plane with the protrusions, to define a planar tissue contacting surface 752. However, in other embodiments the at least some of said protrusions 754 can extend beyond, and/or stop short of the peripheral structure so that tissue contacting surface 752 is not planar. In some embodiments the protrusions 754 may all extend beyond the peripheral structure 760.

The void 754 acts as a reservoir to hold agent within the agent carrier body 750. However unlike previous embodiments this reservoir is located on the tissue contacting surface side of the agent carrier body.

The protrusions 754 are located within the reservoir so that they are in fluid communication with the agent in the reservoir. This allows the protrusions 754 to act on the agent within the agent carrier body 750 and transmit the transportation stimulus into the agent, whereas in the embodiments above the walls of the micro channels acted on the agent within the agent carrier body.

Embodiments of this type generally have more volume for holding agent than embodiments described above. By having a larger filling volume, the possibility of air entrapment may also be reduced. These improved filling properties may give certain embodiments improved filling accuracy and repeatability, which contributes to an increase in dose accuracy, that may be important in medical applications. Furthermore the improved filling may lead to better ultrasonic energy transmission as dampening by retained air spaces is reduced.

It is preferred that the inner surface(s) of the void 754 are functionalised. The inner surface of the void 754 and the protrusions 752 may be functionalised with compounds or molecules having hydrophobic or hydrophilic properties or a combination of both moieties. Alternatively, the surface of the void 754 and the protrusions 752 may be functionalised by contacting the surface of the channels with small molecules that are adsorbed to the surface of the channels, exposing specific functional groups that have the desired physical and/or chemical properties. The small molecules may be adsorbed through chemisorption or physisorption to the internal surface of the channels. Alternatively, or in addition to changing the water/oil affinity, the inner surfaces of the micro-channels and/or agent reservoirs may be functionalised by enabling them to become electro-conductive. In a preferred form loading of the agent carrier body is performed by virtue of capillary forces when the agent carrier is in contact with the agent.

Figure 8A:
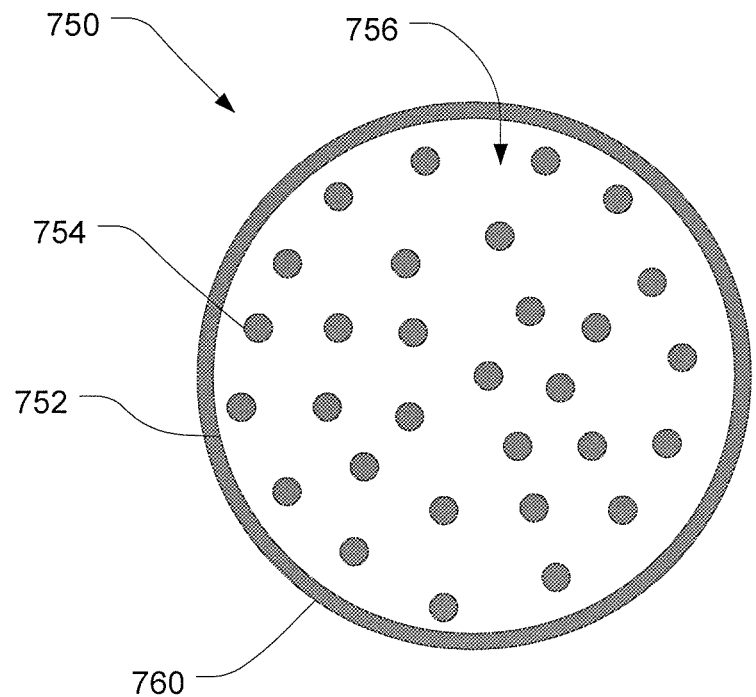
FIGS. 8A and 8B are schematic representations of an alternative embodiment of an agent carrier body, according to an aspect of the present invention, and respectively illustrate plan and perspective views thereof.
Figure 8B:
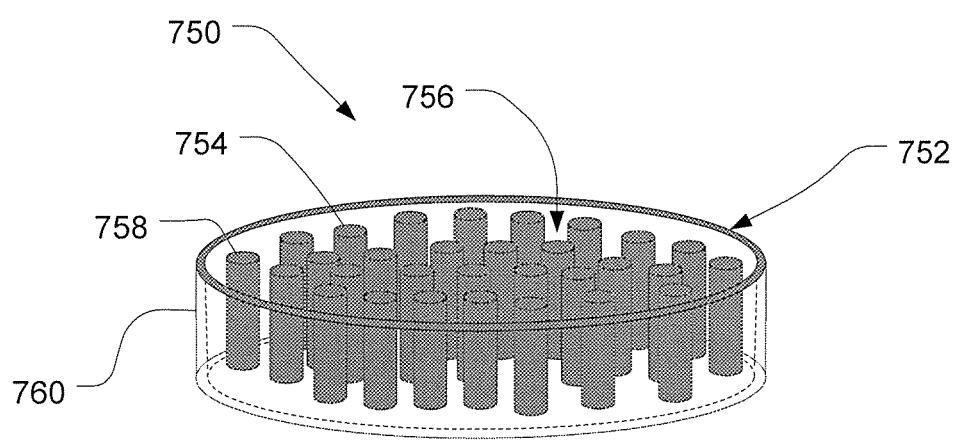
Figure 8C:
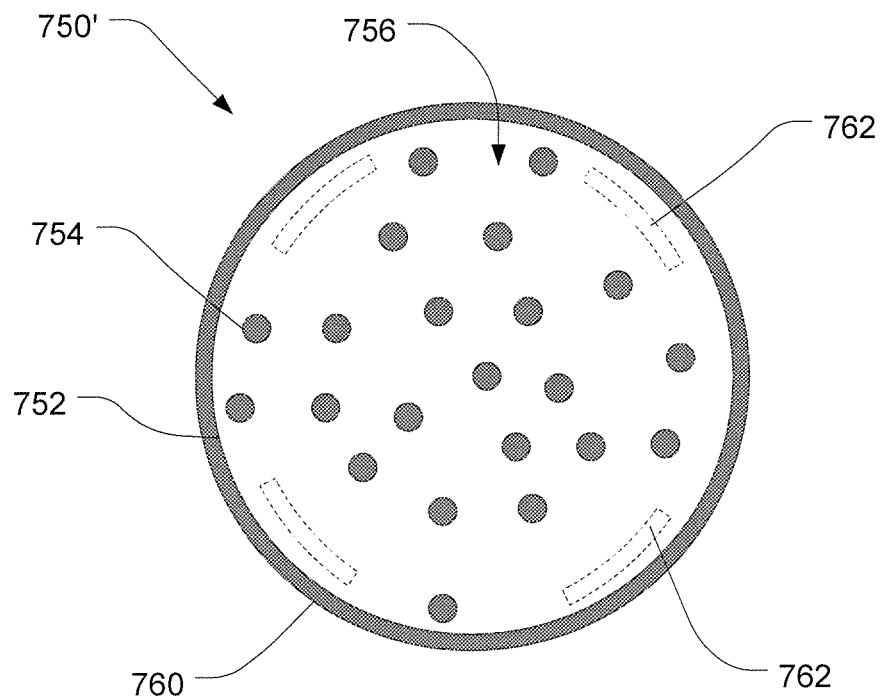
FIGS. 8C and 8D are schematic representations of an alternative embodiment of an agent carrier body layer having micro channels formed through it, and respectively illustrate plan and perspective views thereof.
Figure 8D:
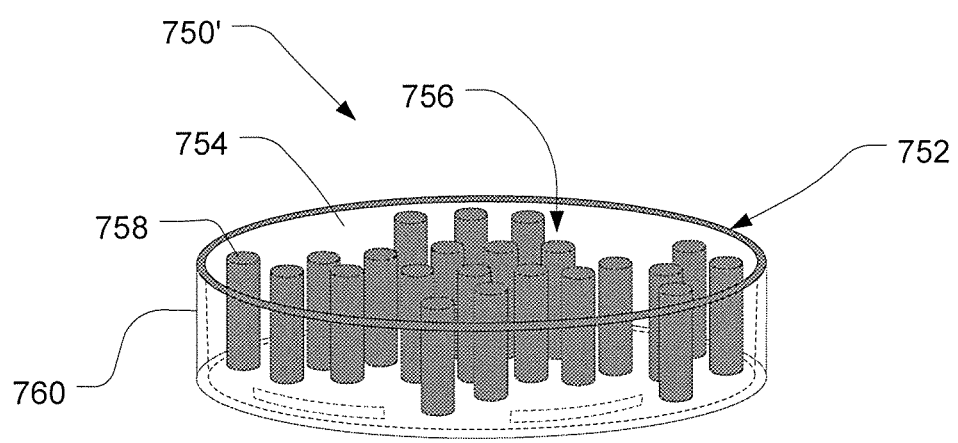

FIGS. 8C and 8D show an agent carrier body layer 750'. In general the agent carrier body layer 750' is the same as the agent carrier body 750 and like features are like numbered. However the agent carrier body layer 750' additionally includes one or more micro channels 762 extending through it. The micro channels 762 extend through the agent carrier body layer so that the reservoir 756 may be fluidly connected to an adjacent agent carrier body layer as in previous embodiments. In this example, four micro channels are used.

Figure 8E:
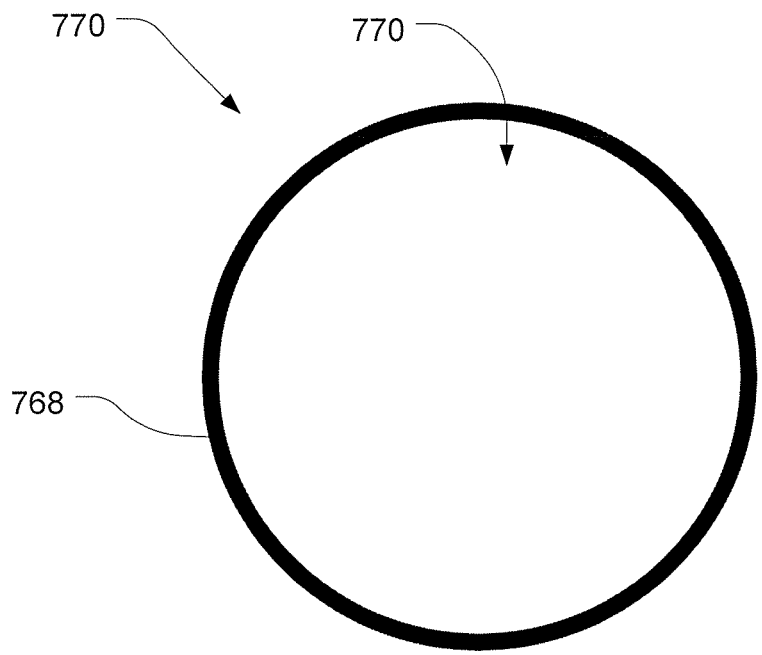
FIGS. 8E and 8F are schematic representations of an alternative embodiment of an agent carrier body layer having a reservoir formed therein, and respectively illustrate plan and perspective views thereof.
Figure 8F:
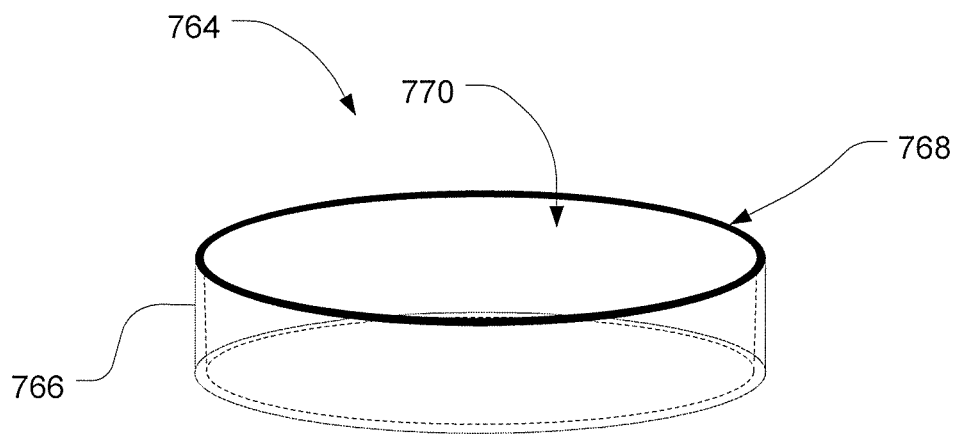

FIGS. 8E and 8F are schematic representations of an agent carrier body layer having a reservoir formed therein. The agent carrier body layer 764 is generally cylindrical in form and includes a peripheral wall 766 that defines a reservoir volume 770 within it. In use the agent carrier body layer 764 is stacked on the agent carrier body layer 750' such that the outer rim 768 of the wall 766 contacts the back of the agent carrier body layer 750' such that a reservoir volume 770 closed. The micro channels 762 in the agent carrier body layer 750' allow agent within the reservoir volume 770 to pass into the reservoir 756 for dispensing.

Figure 8G:
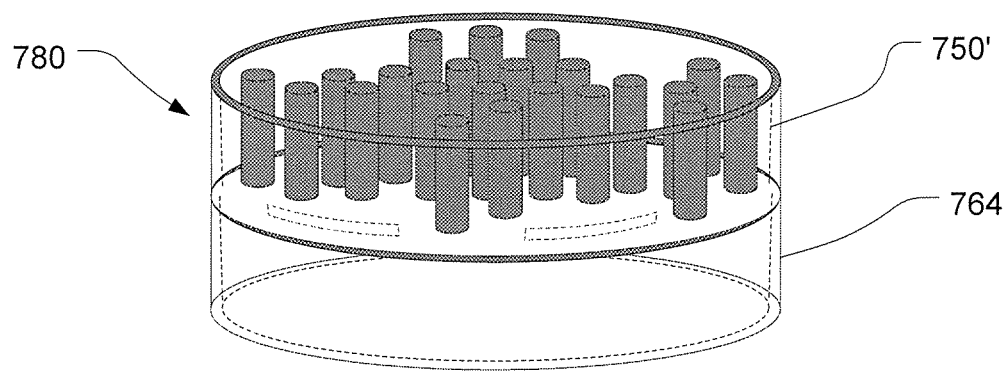
FIGS. 8G and 8H are schematic representations of an agent carrier body formed by the agent carrier body layer of FIGS. 8E and 8F stacked with the agent carrier body layer of FIGS. 8C and 8D, and respectively illustrate the agent carrier body in unfilled and filled configurations FIG. 9A and is an electron micrograph of a portion of an agent carrier body of any one of FIGS. 8A to 8H.
Figure 8H:
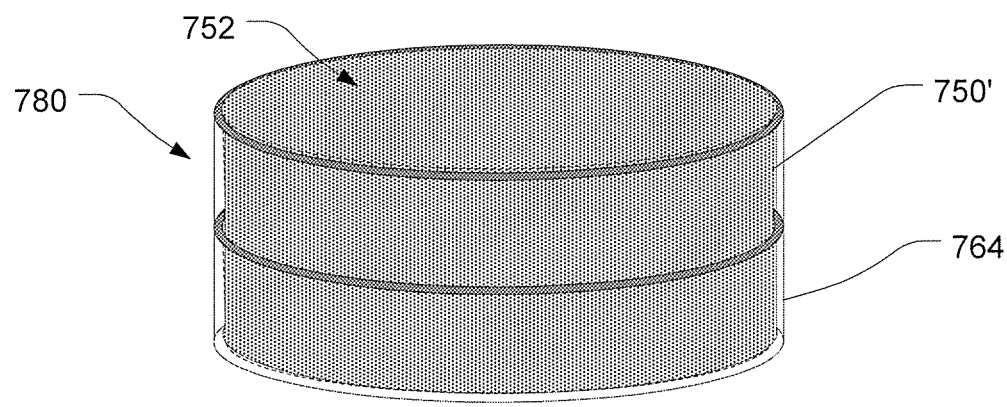

FIGS. 8G and 8H are schematic representations of an agent carrier body formed by the agent carrier body layer of FIGS. 8E and 8F stacked with the agent carrier body layer of FIGS. 8C and 8D to form an agent carrier body 780. The agent carrier body 780 includes a stack of layers including the tissue-contacting layer 750' which includes the tissue contacting surface 752 and one other layer 764. More layers could also be stacked to form an agent carrier body.

In FIG. 8H the agent carrier body 780 is shown filled with agent. In this configuration the agent is filled to the tissue contacting surface 752.

Figure 9A:
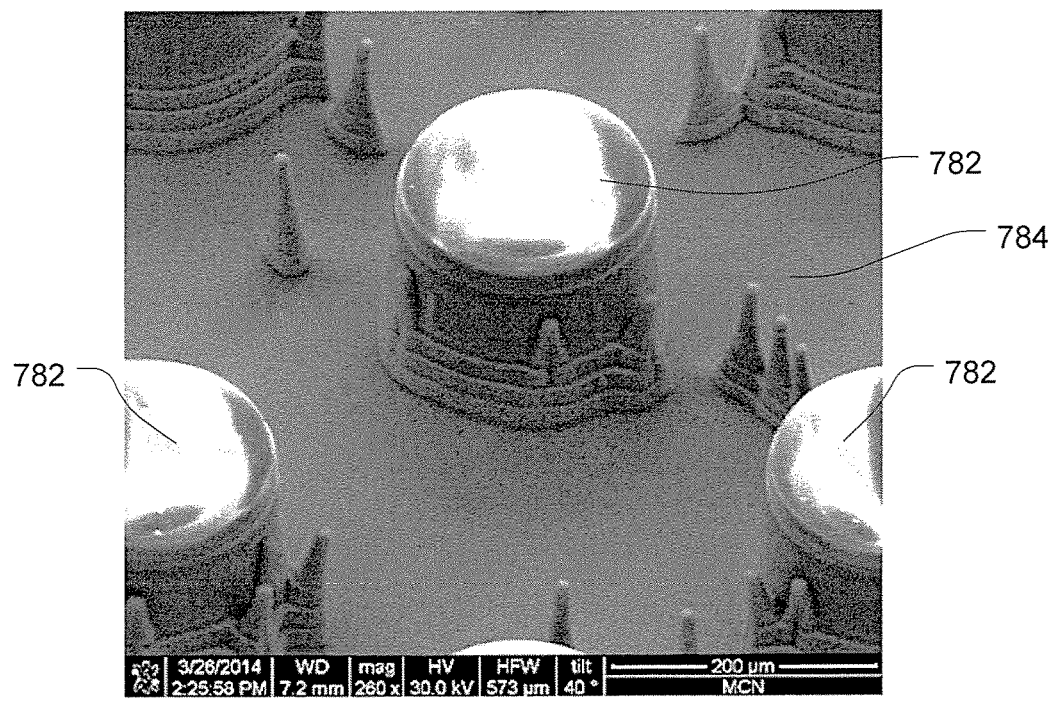
FIG. 9B and is an electron micrograph of a single protrusion of an agent carrier body of any one of FIGS. 8A to 8H.
Figure 9B:
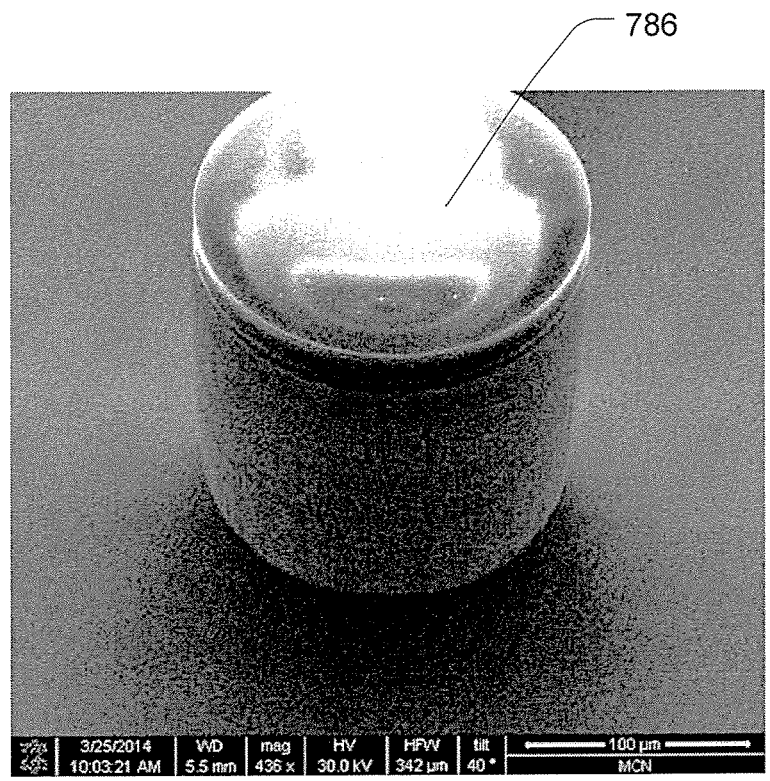

FIG. 9A and is an electron micrograph showing a portion of an agent carrier body (or layer thereof) of the type schematically illustrated in FIGS. 8A to 8H. FIG. 9A shows part of three pillars 782 that operate as protrusions 754. The surface 784 is the base of the void 756 from which the pillars 782 extend. FIG. 9B and is an electron micrograph showing a close up portion of another pillar 786. As can be seen these embodiments from their respective scales, the pillars 782 and 786 are around 200 micrometers wide and a similar height. However in other embodiments different heights and widths may be used.

Figure 10:
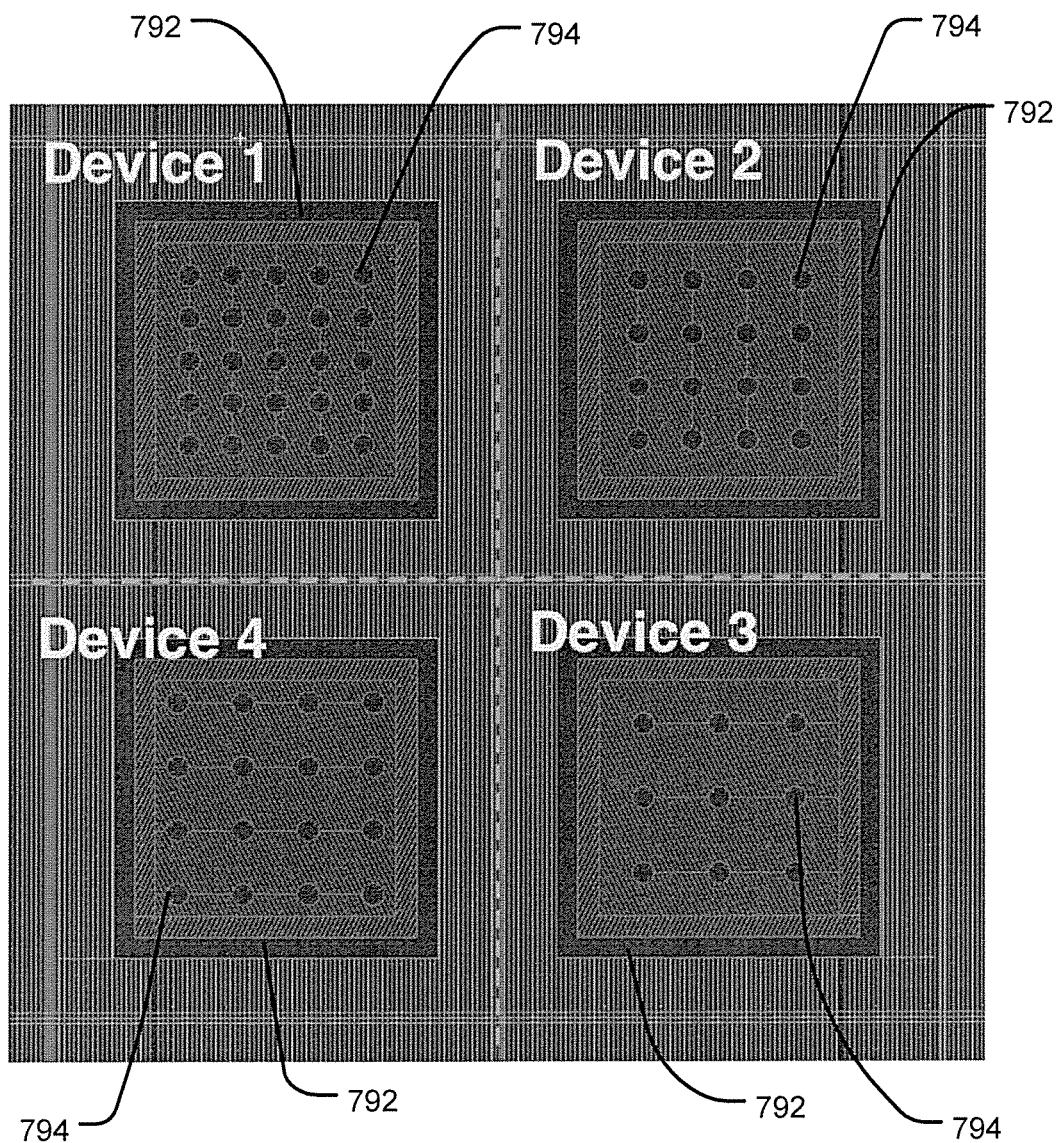
FIG. 10 illustrates a series of four mask designs, each suitable for forming a respective agent carrier body (or layer thereof) in embodiments of the present invention.

FIG. 10 illustrates a series four mask designs, each suitable for forming a respective agent carrier body (or layer thereof). The masks are used in a micromachining process for forming the protrusions and peripheral structure of a tissue contacting surface of an agent carrier. The protrusions are to be arranged in a pattern, in this example in a regular array.

In FIG. 10 the mask for each device (Devices 1 to 4) includes a first mask section 792 for defining a square peripheral wall. Device 1 includes an array of 25 mask sections 794 arranged in a 5×5 array to create a 5×5 array of protrusions. Device 2 includes an array of 16 mask sections 794 arranged in a 4×4 array to create a 4×4 array of protrusions. Device 3 includes an array of 9 mask sections 794 arranged in a 3×3 array to create a 3×3 array of protrusions. Device 4 also includes an array of 16 mask sections 794 arranged in a 4×4 array to create a 4×4 array of protrusions. As can be seen, the protrusions of Device 4 are spaced more widely than that of Device 2. The height of the protrusions in embodiments of the present invention can be chosen to create a void having a desired volume. In some embodiments the protrusions can be greater than 200 µm in height. In some forms they can be less than 1 mm in height. In some embodiments the protrusions can be greater than 300 µm in height. In some forms they can be less than 800 µm in height. In some embodiments the protrusions can be greater than 400 µm in height. In some forms they can be less than 700 µm in height. In some embodiments the protrusions can be greater than 500 µm in height. In some forms they can be less than 600 µm in height. In some embodiments heights greater than 1 mm or less than 200 µm could be used.

Figure 23:
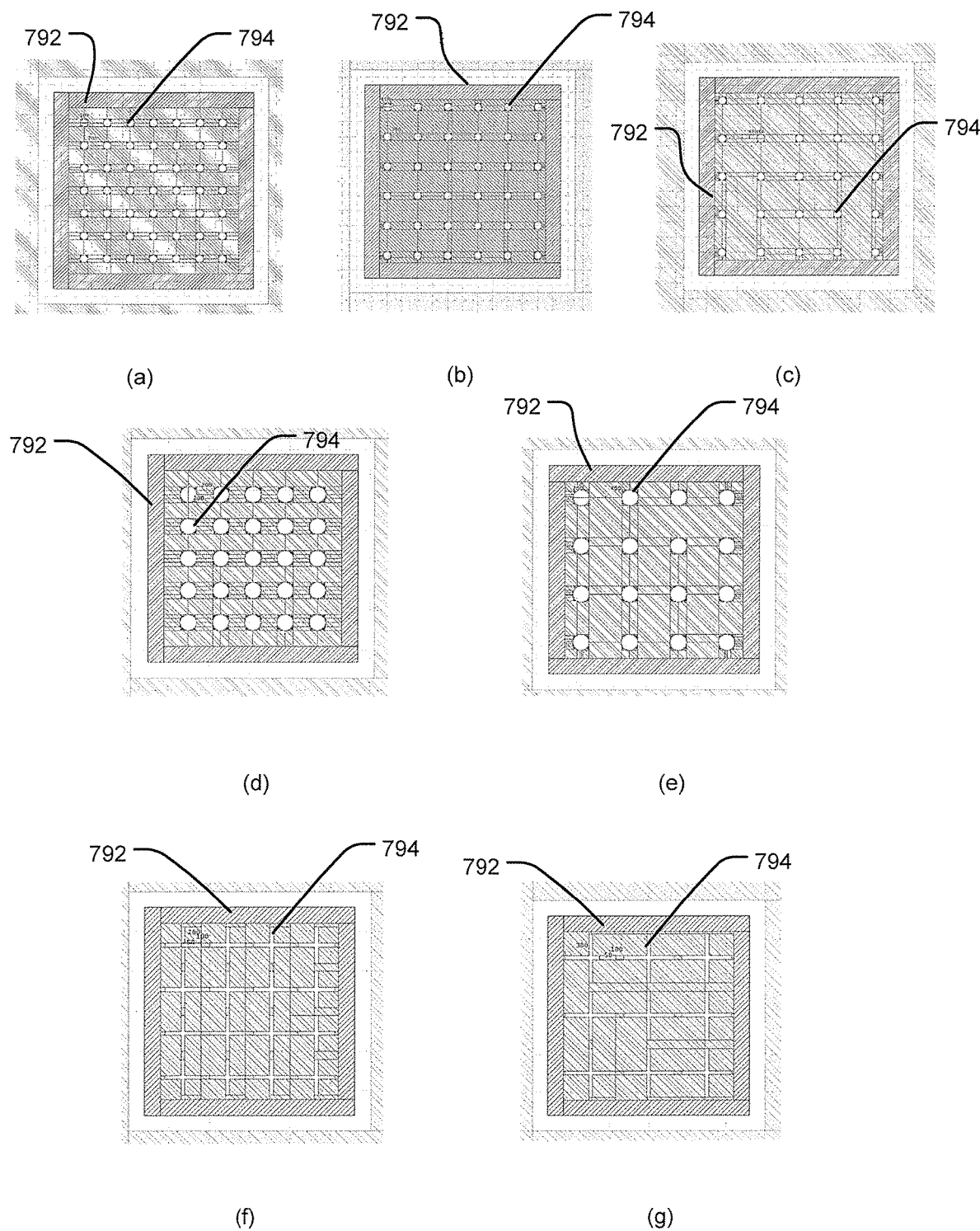

FIG. 23 illustrates a series (a) through (g) of mask designs for creation of various agent carrier bodies (or layers thereof). Figures (a) to (e) are embodiments with round protrusions 794, whereas figures (f) and (g) have protrusions 794 that are cross-shaped in plan-view. The embodiments are summarised in the following table.

| Example | Array | Protrusion width µm | Protrusion separation µm | Protrusion shape |
|---------|-------|---------------------|--------------------------|------------------|
| a | 7 × 7 | 100 | 200 | round |
| b | 6 × 6 | 100 | 300 | round |
| c | 5 × 5 | 100 | 400 | round |
| d | 5 × 5 | 200 | 200 | round |
| e | 4 × 4 | 200 | 400 | round |
| f | 4 × 4 | 450 | 100 | cross 200 µm arm length, 50 µm arm thickness |
| g | 3 × 3 | 650 | 100 | cross 300 µm arm length, 50 µm arm thickness |

It will be appreciated that these embodiments are not exhaustive in any way and many alternative embodiments, having different protrusion dimensions, separations, cross sectional shapes can be devised. It should also be noted that, whilst these embodiments are contained within a square rim designated by reference numeral 792, other shapes can be used. Furthermore, the array of protrusions need not be a regular array or have even density or distribution across the chip. All protrusions 794 used in an embodiment need not have the same cross sectional shape.

Examples (f) and (g) have cross shaped protrusions 794. The cross shaped protrusions have the advantage that they have an increased wall surface area compared to round protrusions, but a reduced cross sectional area, thus maximising agent storage volume. The geometry of cross shaped protrusions also have relatively good mechanical properties, insofar as each arm acts as a buttresses to support the transversely extending arm.

Figure 24:
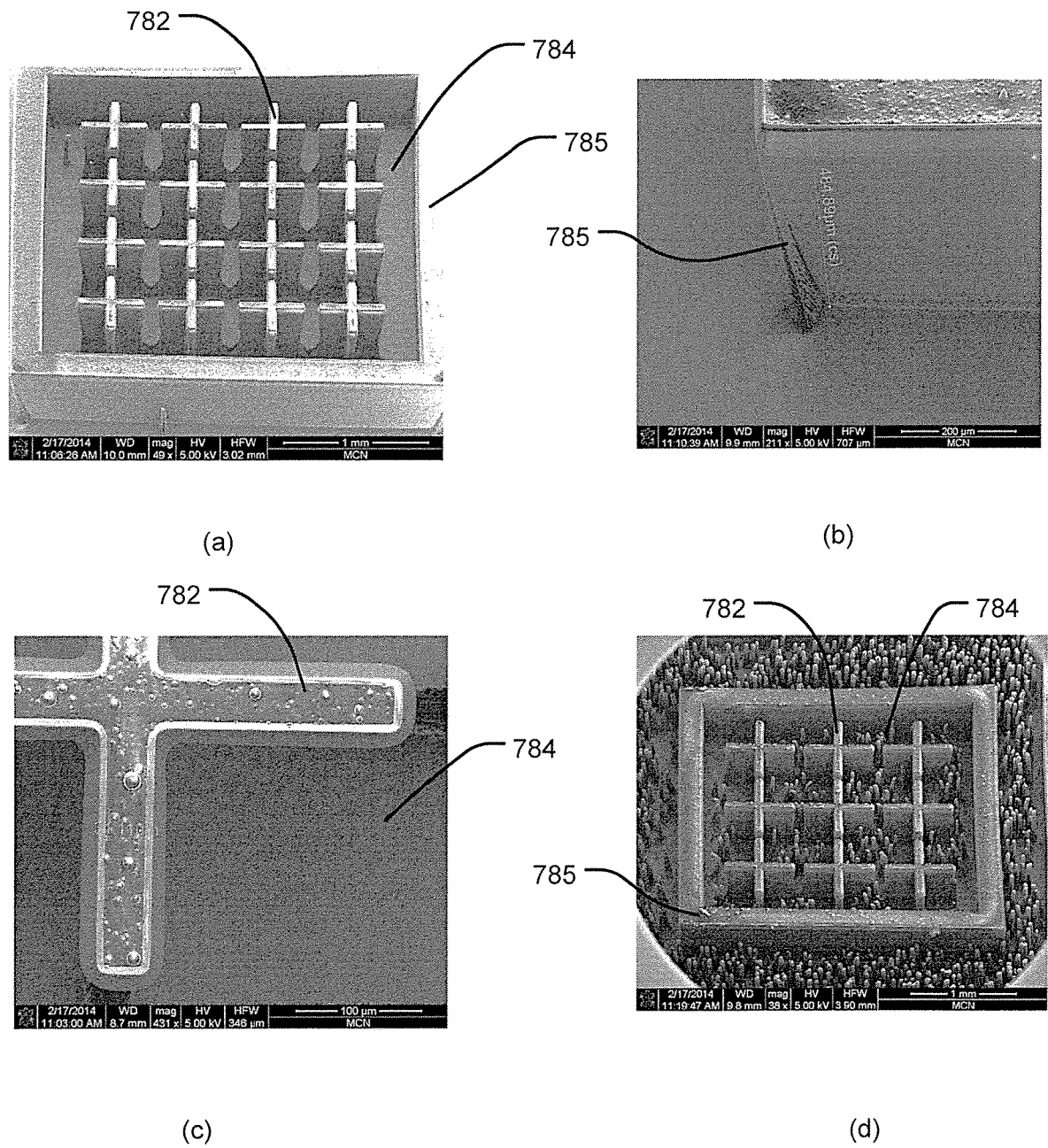
FIGS. 24 to 28 illustrate a series of electron micrographs of agent carrier bodies and regions thereof of various embodiments.

FIGS. 24 to 28 illustrate a series of electron micrographs of agent carrier bodies and regions thereof. FIGS. 24(*a*) to (*c*) show a first embodiment. This embodiment has a 4×4 array of cross shaped protrusions 782 extending upward from a void 784. The void 784 is surrounded by a peripheral wall 785, as in previous embodiments. In use agent to be delivered is retained in the agent carrier body by using the void 784 as a reservoir. As can be seen the protrusions 782 are cross shaped in cross sectional shape over their whole height although their width changes. The changes, particularly near their tip are relatively small, such that the topmost surface, which forms the tissue contacting surface of the agent carrier body, is substantially flat. In this embodiment the peripheral wall 785 is around half a millimetre high, and most specifically 484.89 μm. The protrusions are substantially the same length. The width of the cross profile in this embodiment is 31.11 μm. This is compared with a nominal cross section, as defined by the mask of 50 μm and represents almost a 40% tapering of the protrusion. However, as can be seen the protrusions are not sharp like microneedles despite the small thinning towards the top. This flat surface and the plurality of densely packed protrusions prevent mechanical damage or penetration of the surface by these embodiments.

FIG. 24(*d*) is a further embodiment also having cross shaped protrusions 782 surrounded by a generally square peripheral rim 785. In this example the protrusions are arranged in a 3×3 pattern.

Figure 25:
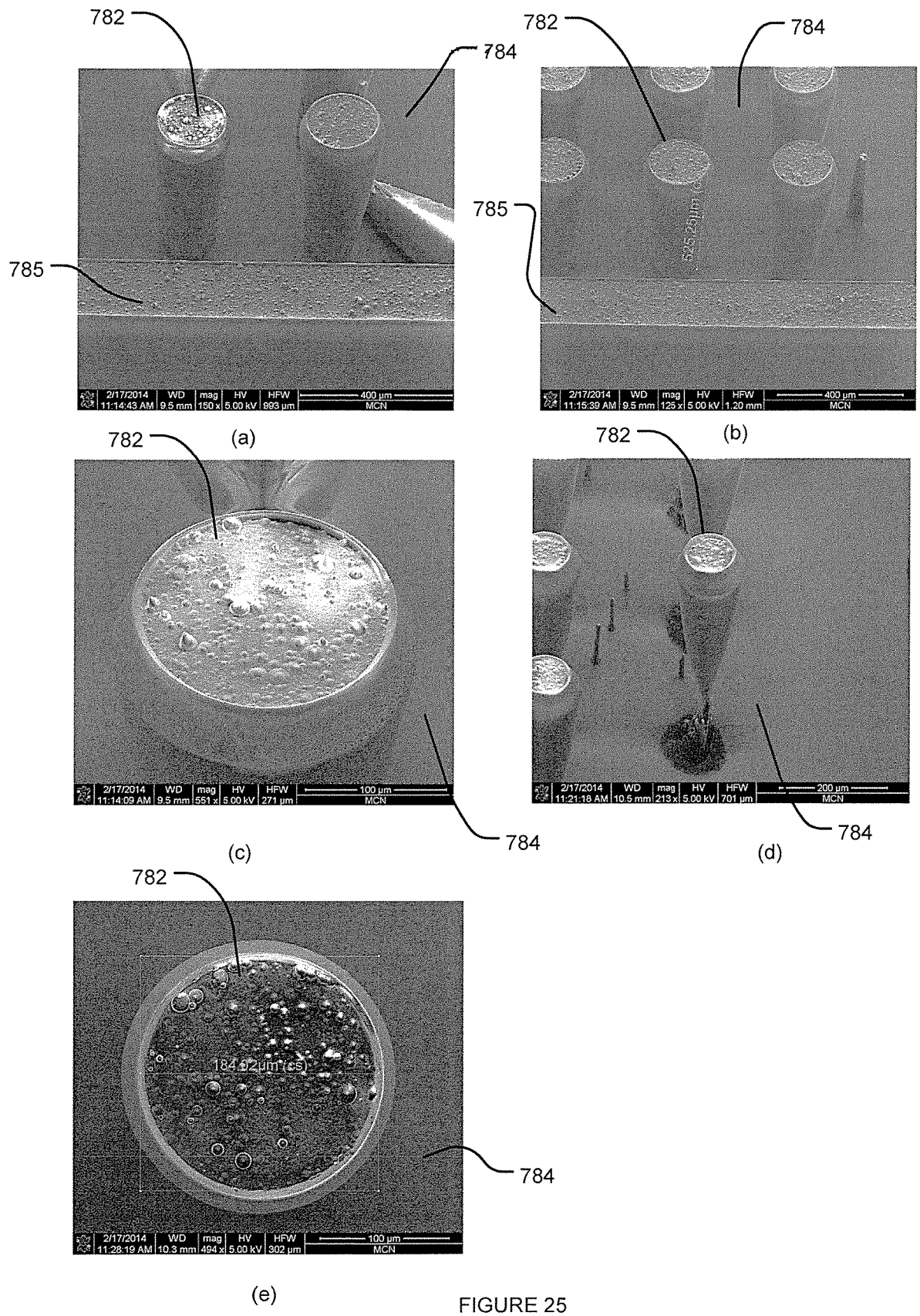

FIGS. 25 (*a*) to (*e*) are electron micrographs of several embodiments with circular cross section. Like features are like numbered and will not be described in detail. As will be observed however, despite a narrowing of the protrusions 782 towards their tip, the tip is flat and not pointed like a microneedle. Again in this embodiment the protrusions are about half a millimetre high (525.25 μm, as shown in picture (b). The diameter of the tip of a protrusion, as illustrated in FIG. 25 is 184.02 μm.

Figure 26:
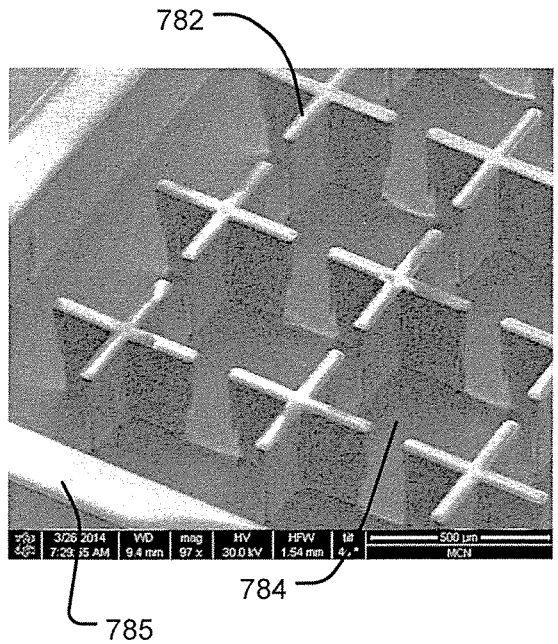
Figure 26:
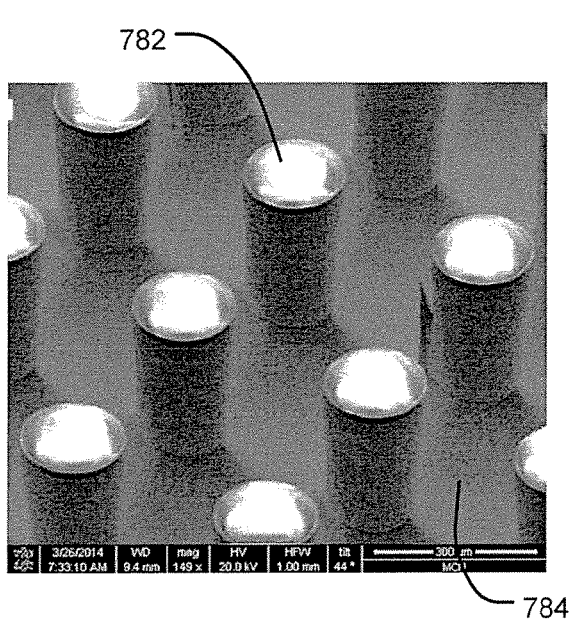
Figure 26:
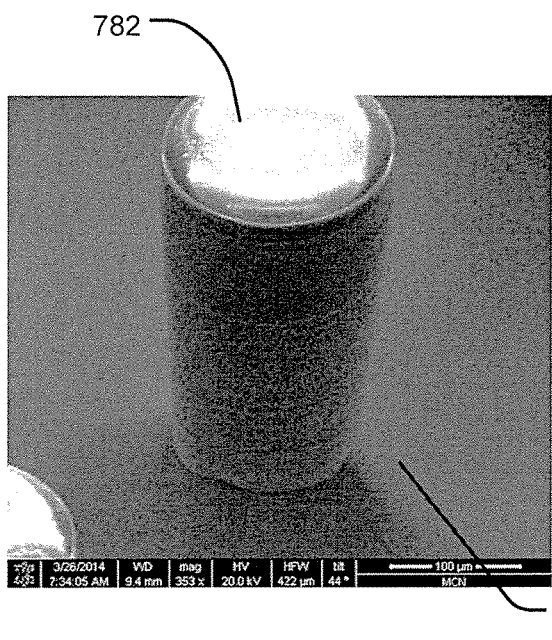
Figure 26:
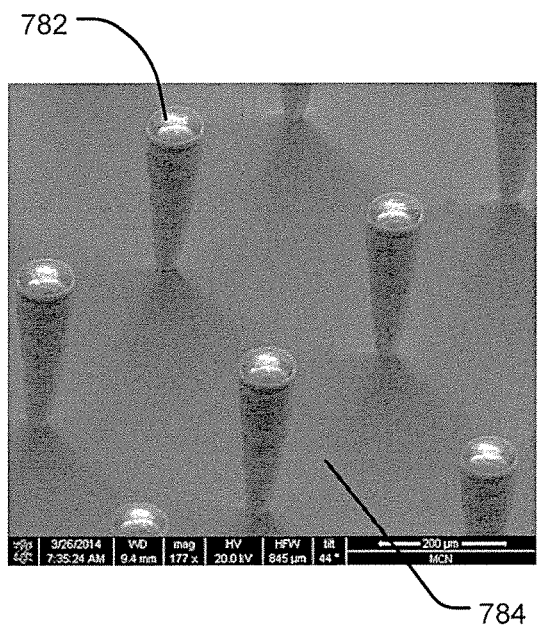

FIGS. 26 (*a*) to (*d*) are electron micrographs of several additional embodiments having cross shaped (a) and circular cross section (b) to (d). In this example the sides of the projections 782 are more vertical than previous embodiments. That is, their sides taper less than the previous embodiments. This is most noticeable in picture (a) to (c).

Figure 27:
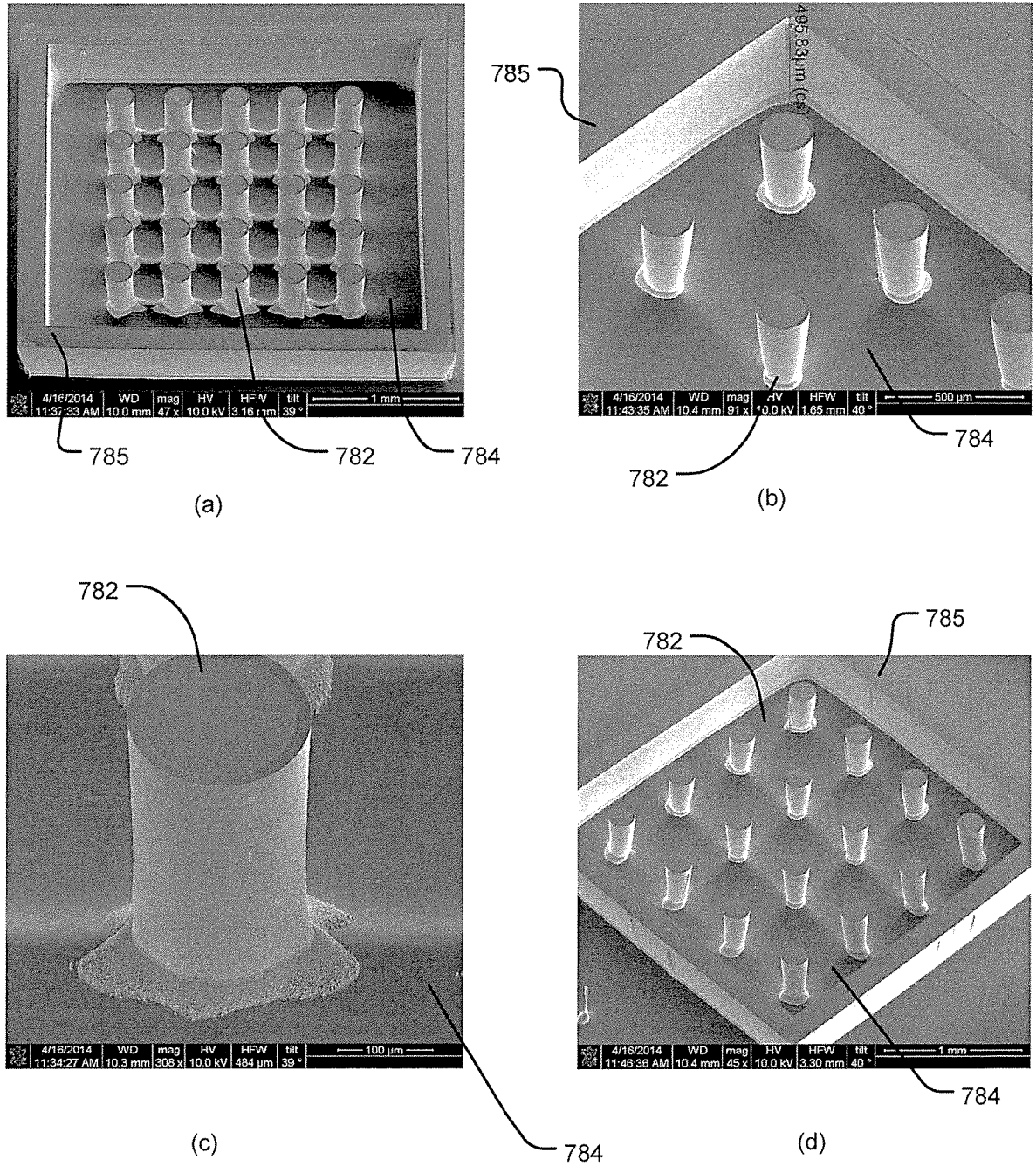
Figure 28:
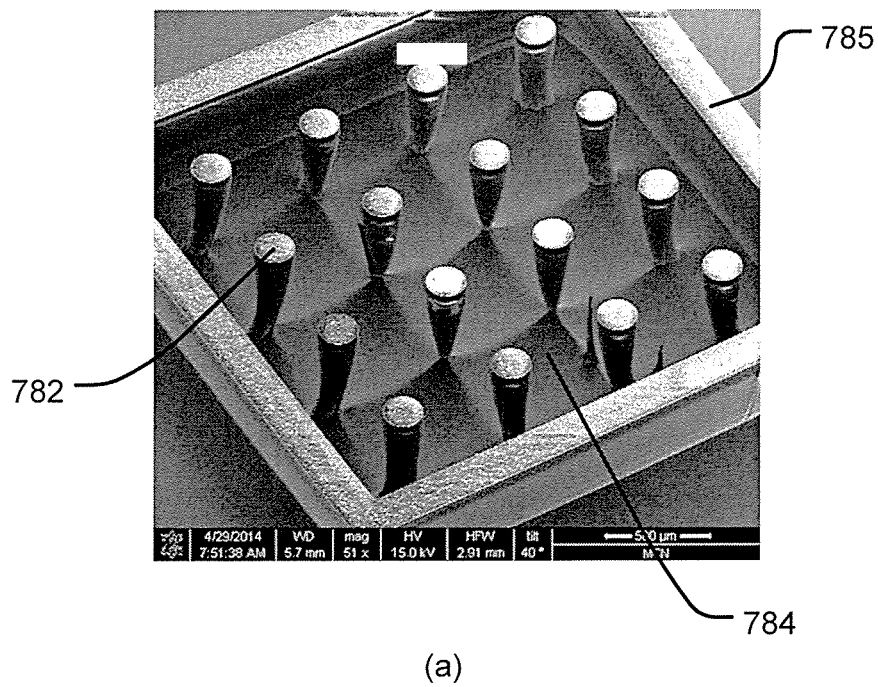
Figure 28:
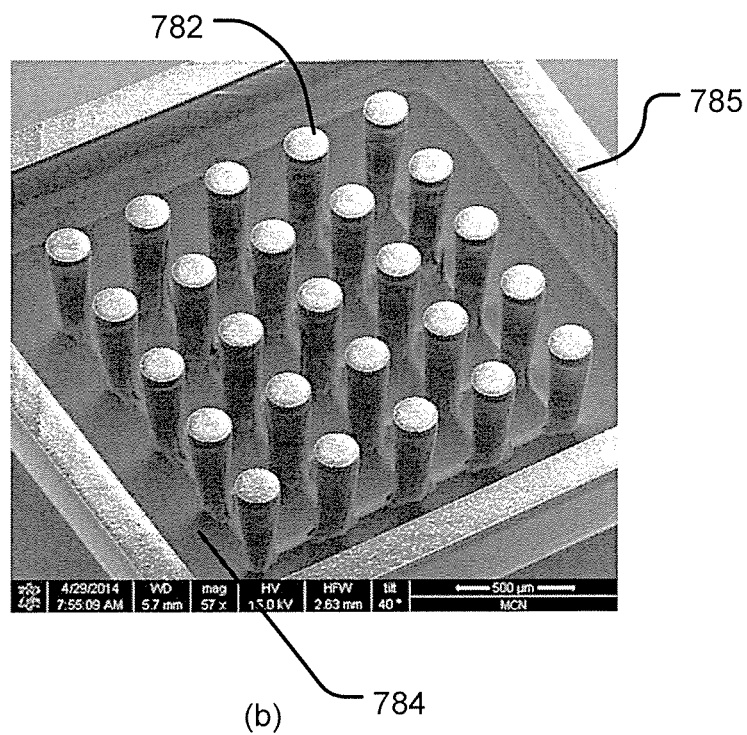
Figure 31A:
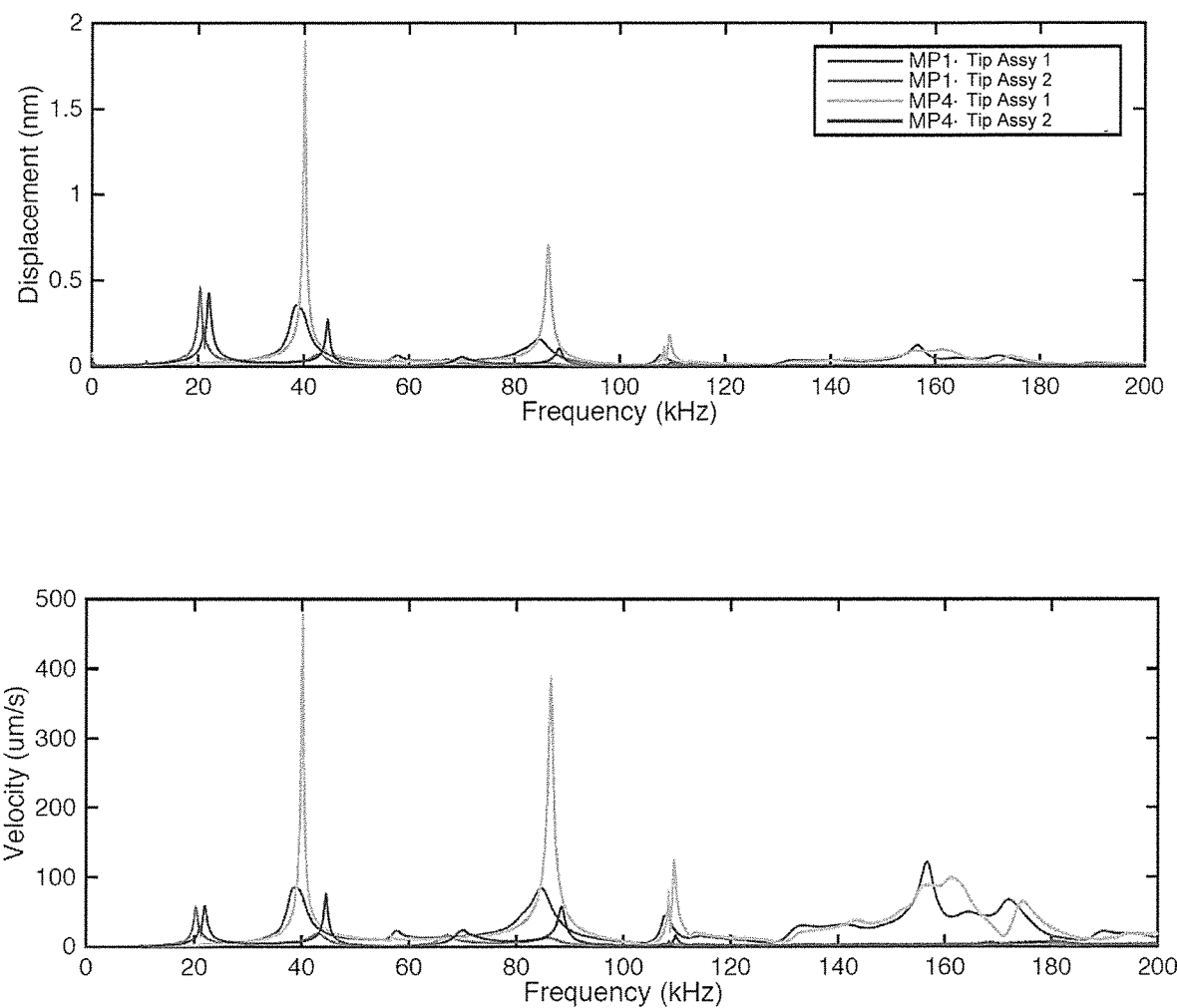
FIG. 31A to 31D illustrates plots of the displacement (nm) and velocity (m/s) during operation of five types of applicator useable with embodiments of the present invention having different tips.
Figure 31B:
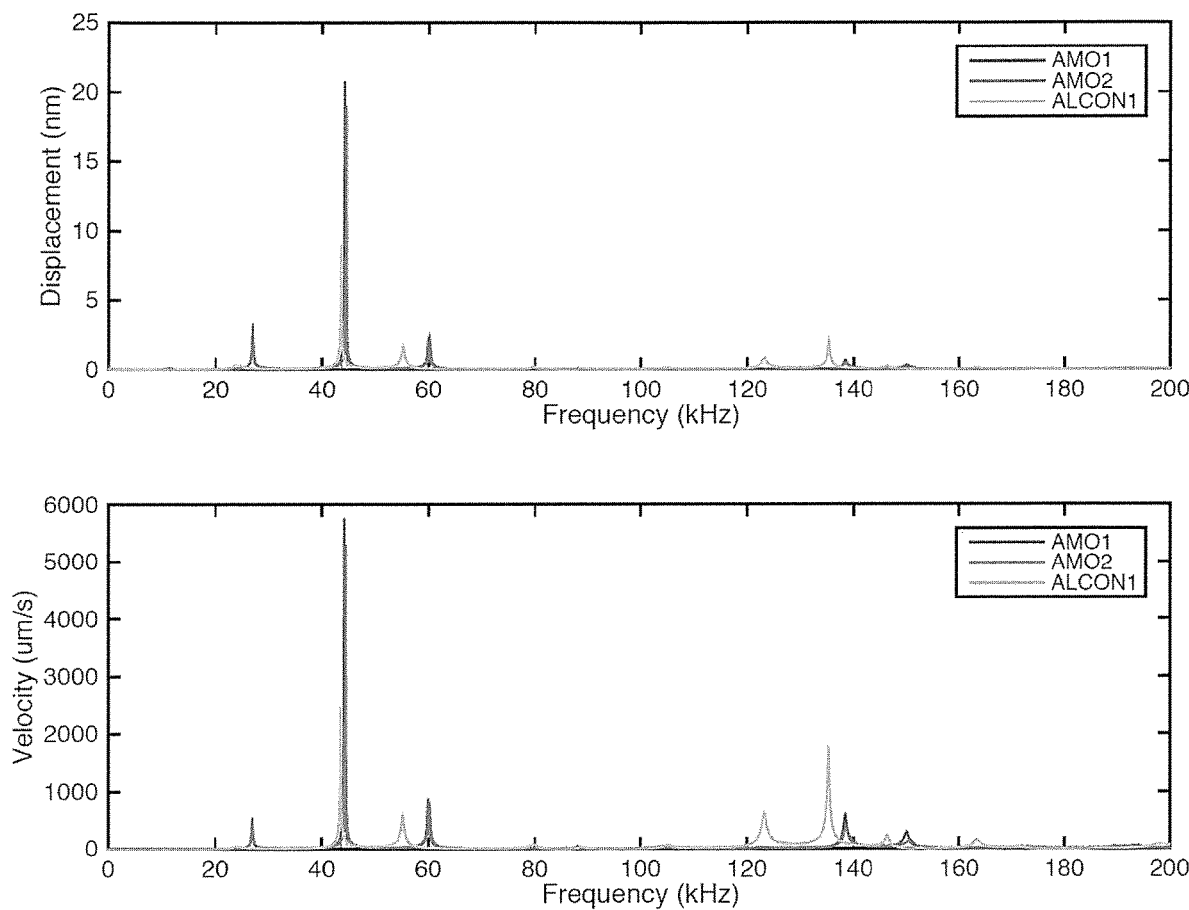
Figure 31C:
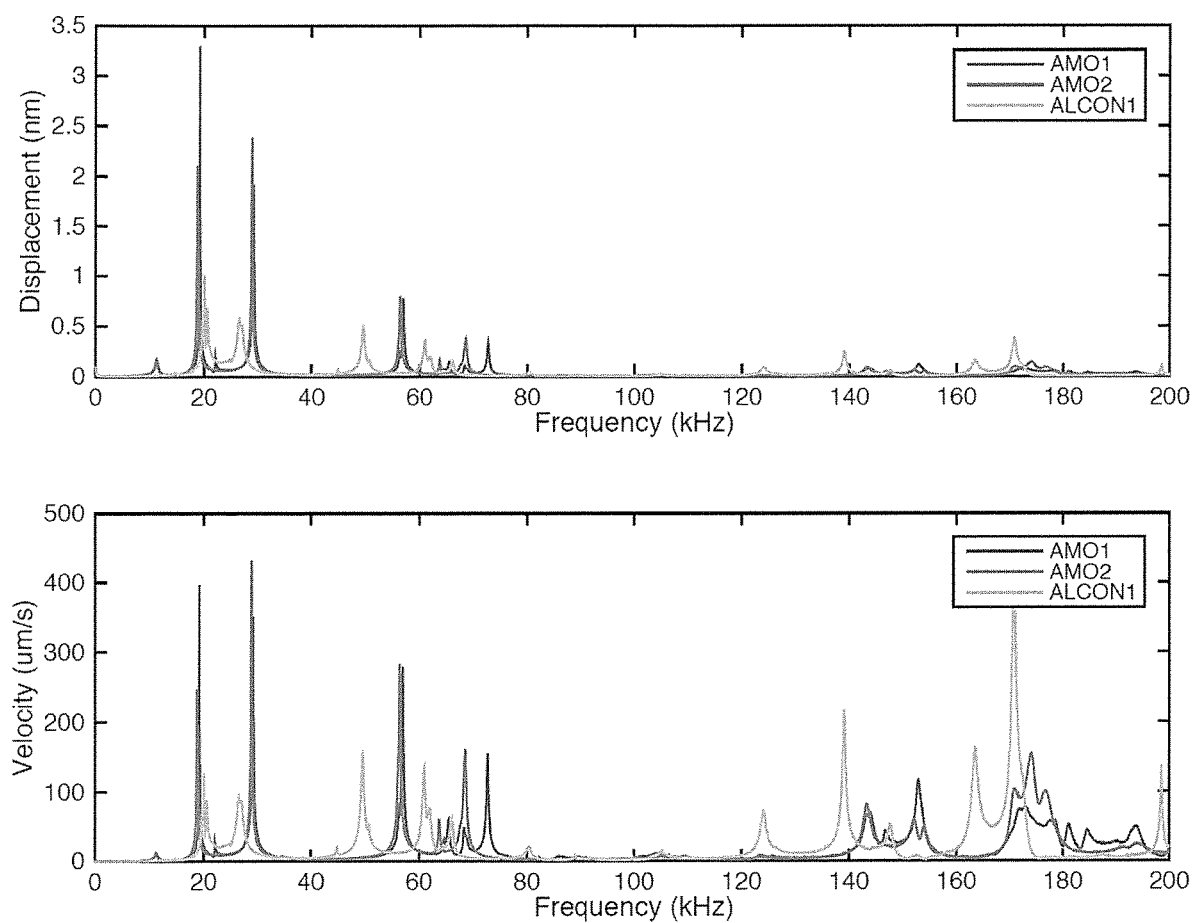
Figure 31D:
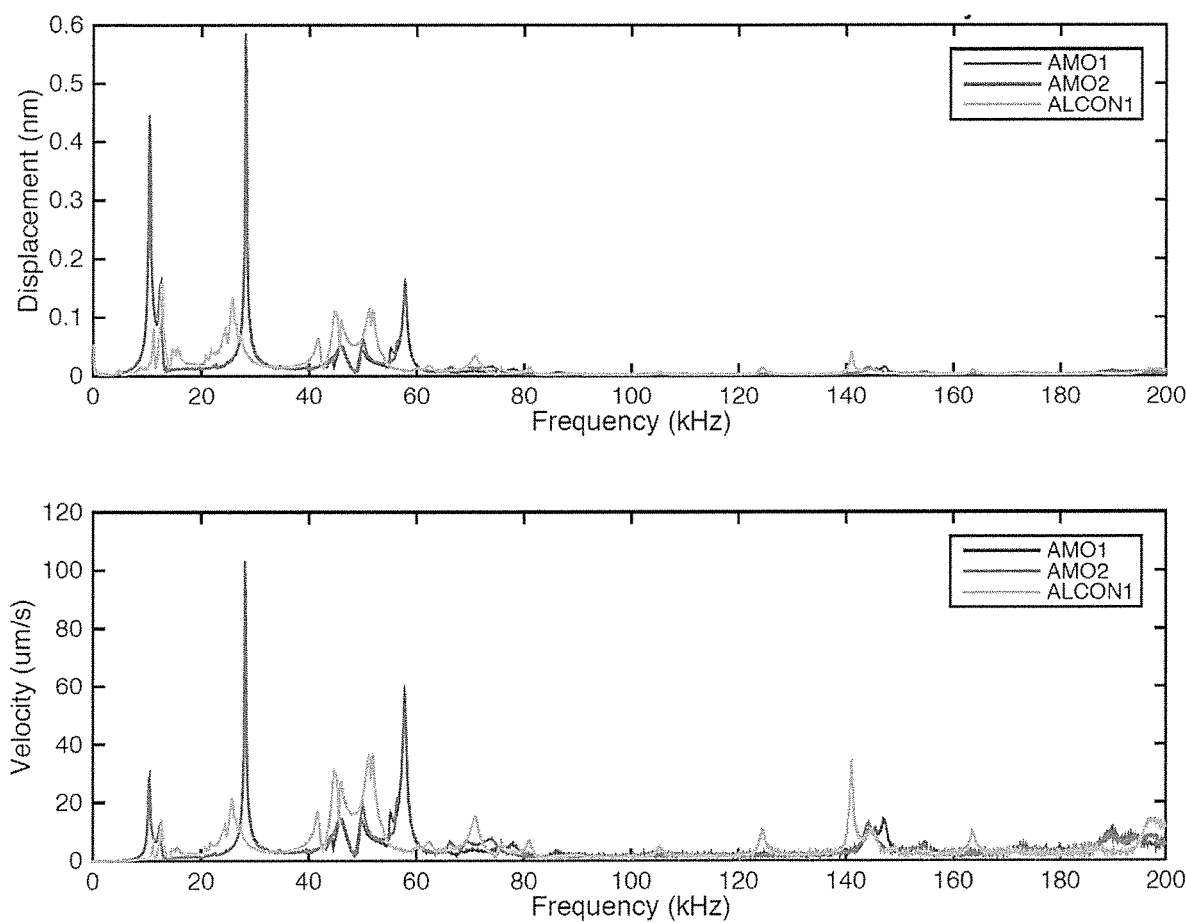
Figure 32:
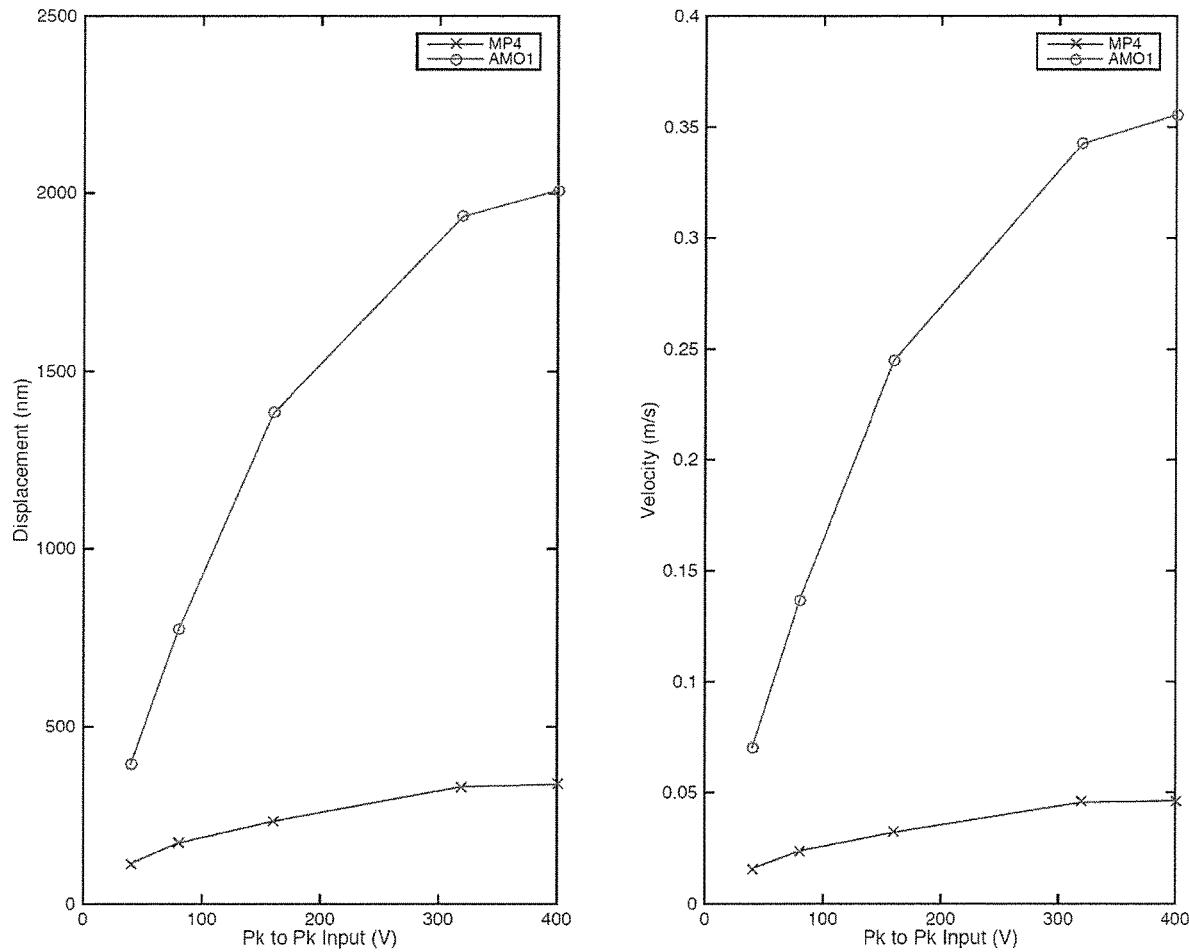
FIG. 32 illustrates the tip displacement of the MP4 and AMO 1 applicators when driven at selected frequencies over a range of drive voltages.

FIGS. 27 (*a*) to (*d*) are electron micrographs of several additional embodiments having protrusions with a circular cross section. Again in these examples the sides of the projections 782 are more vertical than previous embodiments. The height of the peripheral wall and protrusions are again around half a millimetre. Two final embodiments are shown in FIGS. 28(*a*) and (*b*). These example are a 4×4 array and 5×5 array respectively.

In this micrograph the protrusions also taper at their bottom. The tapering is a result of the etching process used during manufacturing, and is largely unintentional. However, in some embodiments, this tapering can be used to advantage as it increases the volume of the void in which agent is held.

4 HYBRID AND ALTERNATIVE EMBODIMENTS

FIGS. 29 and 30 illustrate two hybrid embodiments of the agent carrier body. In FIG. 29 the agent carrier body 104 includes a plurality of micro channels 112 arranged around its peripheral edge in the rim 785. It also has an array of protrusions 782 formed within a central void 784.

FIGS. 30 and 30A illustrates an alternative embodiment, which can be viewed as a protrusion-based embodiment, but with a textured, or profiled rim. In this case the agent carrier body has a peripheral rim 785 which is castellated. The rim 785 has a series of channels or fenestrations 785A that extend through the rim 785 from the peripheral edge to the void 784. The void 784 also contains protrusions 782 in a 3×3 array. To illustrate the arrangement better a cross section along line 30A-30A is provided in FIG. 30A.

An agent carrier having a plurality of agent carrier bodies, perhaps arranged in a pattern such as an array, could also be provided.

5. LOADING AND USE EXAMPLES

Figure 11A:
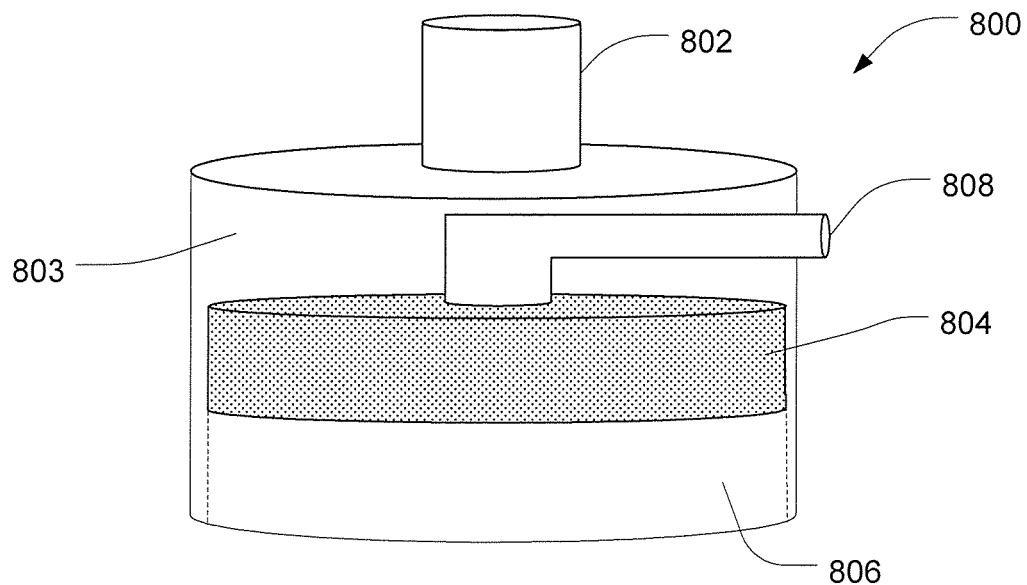
FIGS. 11A to 11C provide an illustration of a various embodiments in which an agent reservoir is provided in an agent carrier in a location external to the agent carrier body. As will be appreciated any
Figure 11B:
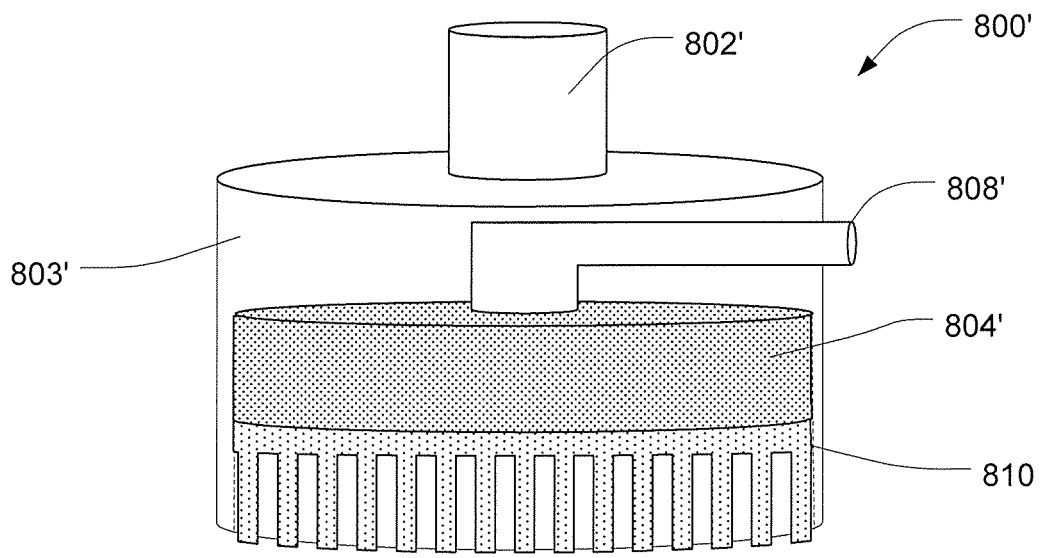
Figure 11C:
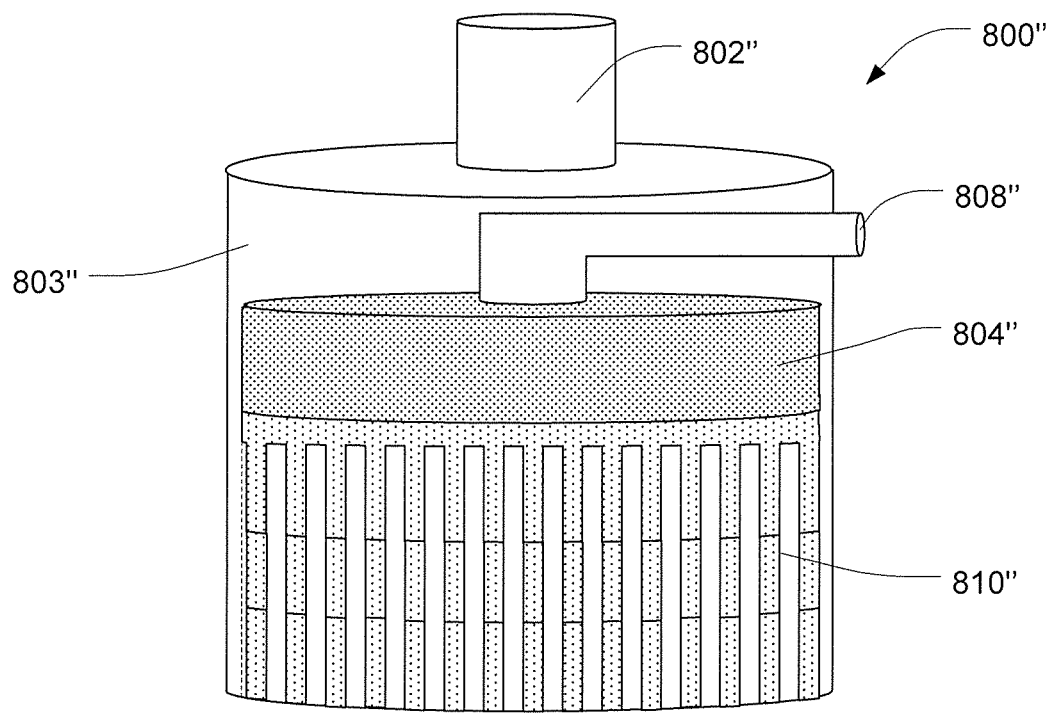

FIGS. 11A, 11B, and 11C illustrate an embodiment in which the agent reservoir is provided within the agent carrier as a separate component to the agent carrier body.

FIG. 11A illustrates a portion of an applicator according to a further embodiment of the present invention. In this figure there is illustrated an embodiment of an applicator tip 800 attached to a coupling rod 802, for coupling the applicator tip 800 to a handle portion of a hand-held agent applicator device. The applicator tip 800 includes an agent reservoir 804 formed within the tip's housing 803. The housing 803 also includes a recess area 806 for receiving an agent carrier body. The agent reservoir 804 includes a port 808. The port 808 may be configured for a number of different uses. In certain embodiments the port 808 may be used to inject the agent reservoir 804 with an agent. In other embodiments the port 808 may be used to apply a vacuum to the agent reservoir 804 to draw agent into the reservoir 804.

FIG. 11B provides applicator tip 800' with an agent carrier body 810 inserted into the recess area 806 (not shown due to the presence of the agent carrier body 810). As will be appreciated from the description in FIG. 11A, the agent reservoir 804' may be filled with an agent by suction applied to the port 808' whereby the agent is drawn through the agent carrier body 810 via its micro channels for storage/holding in the reservoir 804. Alternatively, port 808' may be used to directly inject the agent reservoir 804' with an agent which then fills both the reservoir 804' and the micro channels in the agent carrier 810 with the agent.

FIG. 11C provides a further embodiment of an applicator tip 800" as generally described above, and accordingly corresponding features have been like numbered with the addition of double prime to indicate the change of embodiment. The applicator tip 800" is connected to coupling rod 802". It includes an agent reservoir 804" and a stacked agent carrier body 810". In other respects it is the same as the previous examples.

FIGS. 12A, 12B, 12C, 12D, and 12E provide illustrations of mechanisms, modifications and methods of charging an agent carrier with agent and/or other substances that assist in the loading, retention and delivery of agent by the system.

The loading mechanisms, generally illustrated in FIGS. 12A to 12E, may also be used alone, or in combination, as methods for lining the surface of the agent carrier or its cavities with hydrophilic or hydrophobic moieties prior to loading an agent, or with moieties that can conduct electric charges and/or participate in generating or propagating electric fields prior to loading an agent.

Figure 12A:
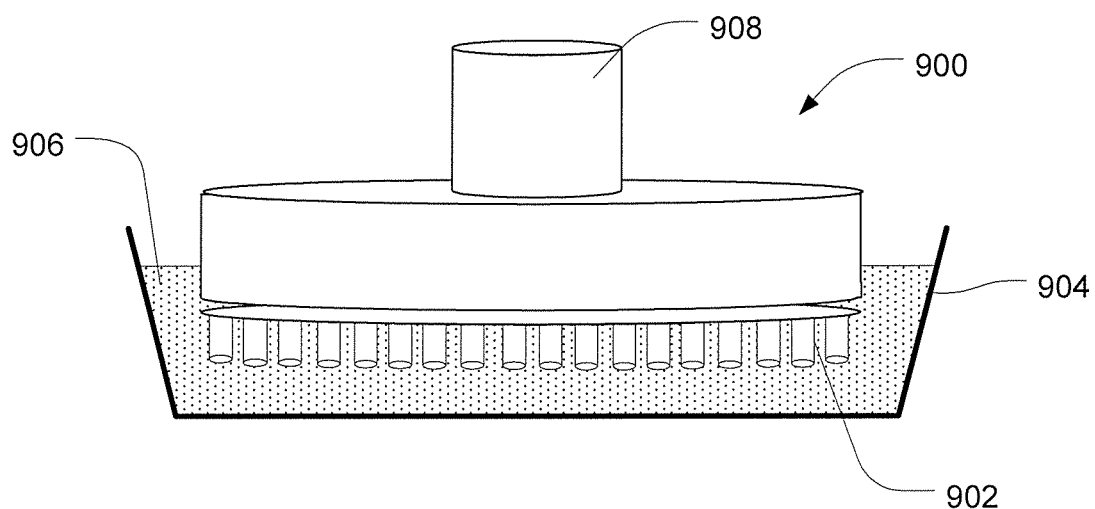

FIG. 12A provides an illustration of an embodiment of a method for charging an agent carrier with an agent. In this embodiment, the applicator tip 900 containing the agent carrier body 902 is connected to a hand-held applicator device (not shown) via its coupling rod 908. The agent carrier body 902 is at least partially immersed in a container 904 containing an agent 906. Ultrasonic vibration created by an ultrasonic transducer of the applicator device is coupled, via the coupling rod 908 to the applicator tip 900, and through it, to the agent carrier body 902. The vibration expels air from the micro channels and at least partially fills the micro channels and/or agent reservoirs within the agent carrier body 902 with agent 906.

Figure 12B:
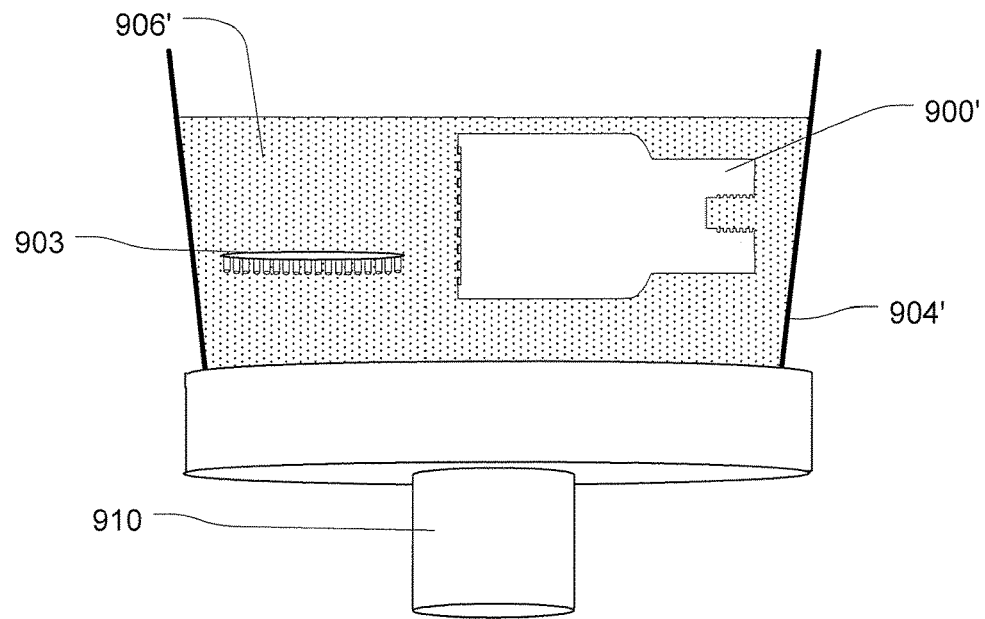

FIG. 12B provides an illustration of another embodiment of a method for charging an agent carrier with an agent. In this embodiment, the agent carrier is a removable applicator tip 900'. The applicator tip 900' and/or a separate agent carrier body 903 are at least partially immersed in a container 904' containing an agent 906'. Ultrasonic vibration created by an external source 910 is applied to the container 904', which expels air from the micro channels and/or agent reservoirs of the agent carrier contained in the applicator tip 900' (not shown) and/or the separated agent carrier body 903 and at least partially fills the micro channels and/or agent reservoirs of the agent carrier within the applicator tip 900' and/or the separated agent carrier body 903 with agent 906'. In other embodiments loading may be performed by simple immersion of the agent carrier or agent carrier body without application of ultrasonic vibration.

Figure 12C:
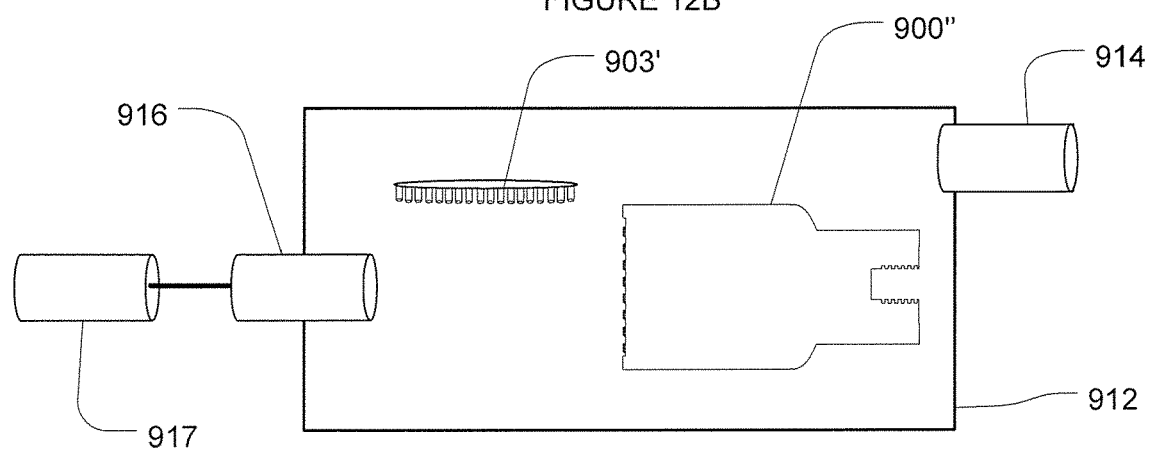

FIG. 12C provides an illustration of a vacuum chamber 912. Vacuum is applied at the port 914 to remove air from the chamber 912 and the air within the micro channels and/or agent reservoirs of an agent carrier held within an applicator tip 900" or a separated agent carrier body 903'. When the vacuum is complete, a valve controlling the agent entry port 916 is opened so that agent stored in chamber 917 is drawn into the chamber 912 through the agent entry port 916 and into the micro channels and/or agent reservoirs in the agent carrier body 902" in the applicator tip 900" and/or the separated agent carrier body 903'. Ingress of agent occurs via the pores in the tissue-contact surface of the agent carrier(s). Once charged with agent, the applicator tip 900" and/or the separated agent carrier body 903' is removed from the agent containing fluid and a seal layer may be applied over exposed surfaces.

Figure 12D:
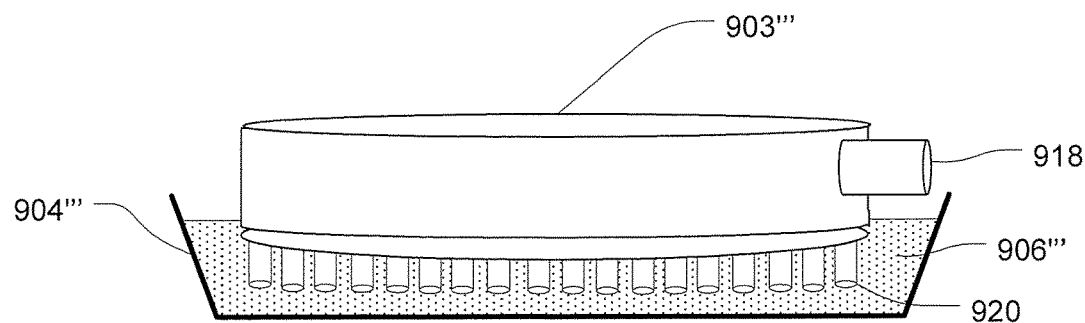

FIG. 12D provides another embodiment of a method in which a vacuum is used to charge an agent carrier body 903''' with agent 906'''. Agent 906''' is held within a container 904'''. The agent carrier 903''' is placed within the container 904''' and at least partially submerged so that the pores of the tissue contact surface 920 of the agent carrier body 903''' are in the agent solution 906'''. A vacuum is applied to port 918 to draw agent solution up through the micro channels in the agent carrier 903''' so that the micro channels and/or agent reservoirs are at least partially filled with the agent solution 906'''.

In an alternative embodiment of a method for charging an agent carrier body with agent, an agent can be directly injected into the port so that the air in the agent carrier (i.e. in the micro channels and/or agent reservoirs) is expelled and replaced by the agent.

Figure 12E:
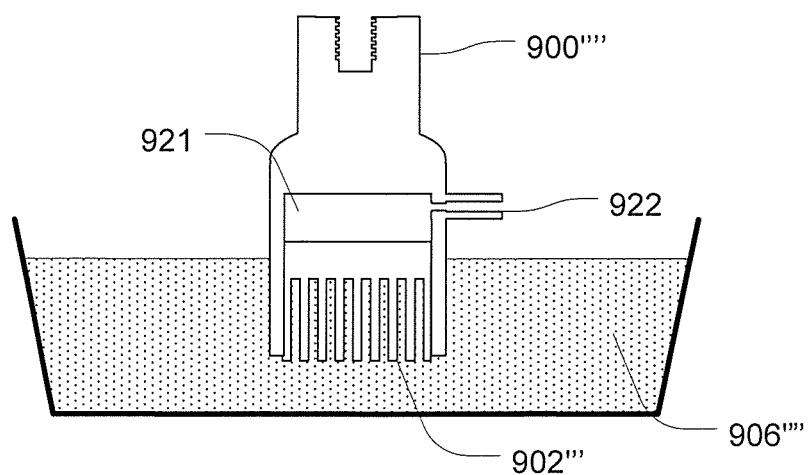
Figure 13A:
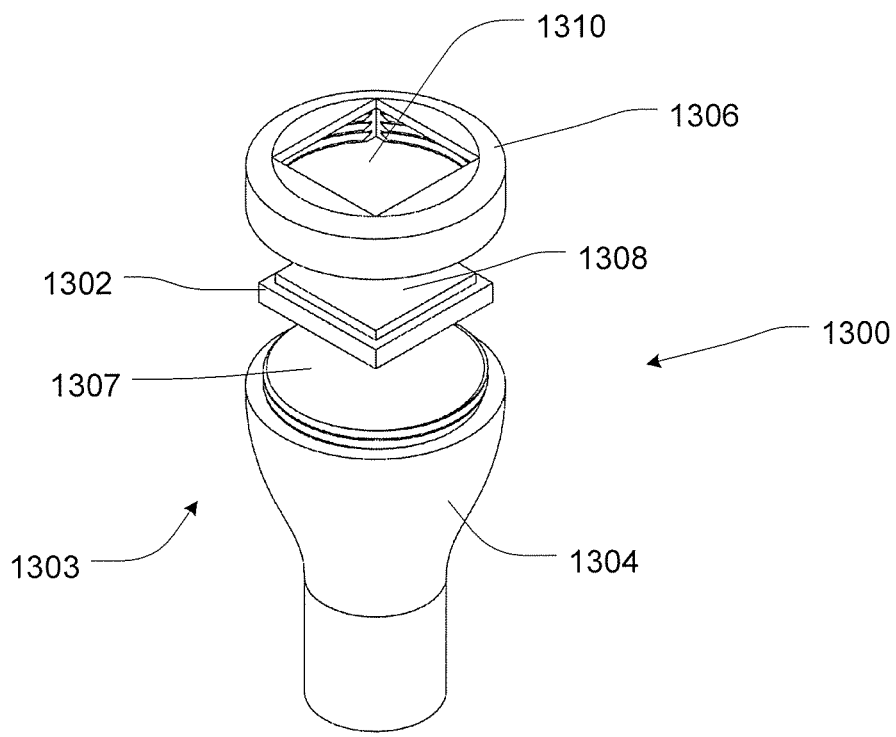
Figure 13B:
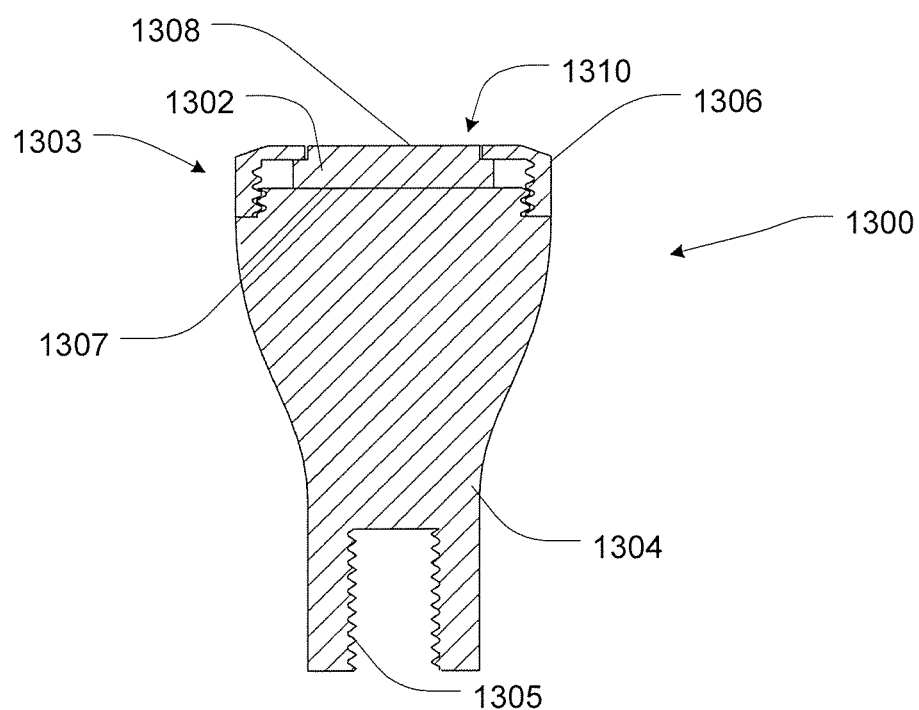

FIG. 12E provides a similar method to that in FIG. 12D except an applicator tip 900'''' having an agent carrier body 902''' is to be charged with agent. The applicator tip 900'''' is illustrated in cross section to illustrate that the applicator tip includes a reservoir 921 within its housing that is separate from any reservoir formed within the agent carrier body 902'''. The applicator tip 900'''' includes a vacuum port 922 that provides access to the reservoir 921. As above, a vacuum is applied at the vacuum port 922 which draws agent solution up through the micro channels in the agent carrier body 902''' so that the micro channels and/or agent reservoirs in either the agent carrier body 902''' or applicator tip's 900'''' housing are at least partially filled with the agent solution 906''''.

In an alternative embodiment of a method for charging an agent carrier or applicator tip having an agent carrier with agent, agent can be directly injected into a port so that the air in the agent carrier (e.g. in the micro channels and/or agent reservoirs) is expelled and replaced by the agent.

As will be appreciated, the loading techniques described above can be used with suitable micro-channel, hybrid or protrusion based agent carrier bodies described herein or devised. However, agent carrier bodies or agent carriers which permit direct access to an agent reservoir may be loaded by directly placing agent into the reservoir, e.g. by pipetting the agent onto the reservoir. One example of such a mechanism was used in the experiments described below. In this example the agent was pipetted into the void on the tissue contacting surface of the agent carrier body of a protrusion-based agent carrier body. In a similar manner, agent may be pipetted to a reservoir on the back of the agent carrier body for delivery via micro channels to the tissue contacting surface.

The agent carrier may be provided as either empty agent carriers or as charged agent carriers that are filled with an agent. Where empty agent carriers are provided, an end user will need to charge the agent carrier with agent prior to use.

The invention also relates to a method of charging the agent carrier with an agent and discharging agent from the agent carrier.

The method of discharging agent from the agent carrier or dispensing agent to a tissue surface includes applying the agent carrier to a tissue surface and dispensing agent from the agent carrier to the tissue surface. Preferably the process of dispensing the agent includes applying ultrasonic waves to the tissue surface to facilitate penetration of the agent into the tissue through sonophoresis.

As will be appreciated from the foregoing the agent carrier or an agent carrier body itself can be an item separable from the applicator device. In a preferred form the agent carrier or agent carrier body is a single use item that is removable or interchangeable. This aids in the sterility required for medical usage and facilitates among other things cleaning and sterilising of the hand-held applicator device between patients. The solid physical nature of the preferred embodiments facilitates mounting and handling of the agent carrier in circumstances where they are replaceable. Moreover, the use of a solid material for the agent carrier body to contain the agent facilitates loading of an agent into an agent carrier, packaging, handling of agent carrier bodies pre-loaded with agent.

Importantly, the use of solid materials for the agent carrier body facilitate the propagation of ultrasonic waves that are used to move an agent through the agent carrier and enhances and/or permits the entry of an agent into the target tissue by sonophoresis.

FIGS. 13A and 13B illustrate one embodiment agent carrier. The applicator tip 1300 is generally speaking equivalent to the agent carrier tip 102 shown in FIG. 1. In this example the agent carrier 1300 takes the form of an applicator tip with a removable and interchangeable agent carrier body.

The agent carrier 1300 includes the following main components: An agent carrier body 1302, and a tip housing 1303 that includes a tip body 1304 and an agent carrier body retaining cap 1306.

The agent carrier body 1302 is generally rectilinear in plan view, and in this example it is square. The agent carrier body 1302 may be made in accordance with any one of the examples given above or aspects described herein. The agent carrier body 1302 has a tissue contacting surface 1304.

The tip body 1304 serves to both connect the agent carrier 1300 to an agent applicator device and conduct transmission stimulus, in the form of ultrasonic energy to the agent carrier body 1302. To achieve this, the tip body 1304 is provided, on a first end thereof, with a mounting mechanism 1305 in the form of a screw thread. The mounting mechanism 1305 is used to make a mechanical connection with a corresponding connector of a handle assembly. The second end of the tip body 1304 is shaped to operate as a horn to conduct ultrasonic energy, via mating surface 1307, to the agent carrier body 1302.

The agent carrier body retaining cap 1306 serves to retain the agent carrier body 1302 and hold it in contact with the mating surface 1307. The agent carrier body retaining cap 1306 has an aperture 1310 formed in it, through which the tissue contacting surface 1308 of the agent carrier body 1302 is exposed in use. The agent carrier body retaining cap 1306 is mounted to the tip body 1304 using a screw thread.

As will be appreciated there are many morphological and mechanical variations can be made in such a system. For example the shape of the components, including the agent carrier body, and its associated tissue contacting surface may be varied. The present square embodiment is particularly convenient when the agent carrier body is made from a semiconductor material and its manufacturing process most conveniently outputs square components. The shape of the tip body can be varied to optimise transmission of ultrasonic energy if ultrasonic energy is used as a transportation stimulus. The shape of the aperture thorough which the tissue contacting surface of the agent carrier body is exposed can be varied. In some cases it may differ from the shape of the tissue contacting surface of the agent carrier body.

The method of engagement of the agent carrier retaining cap with the tip body can be varied widely to use any convenient type of mechanism. In this example engagement is by screw thread, however the agent carrier retaining cap could be press fit onto the tip body, or engaged with snap fasteners, or a bayonet fitting, to give a non-exhaustive list or alternatives. Similarly the mounting mechanism of the agent carrier body can be varied to use any known coupling mechanism.

An agent carrier having a plurality of agent carrier bodies, perhaps arranged in a pattern such as an array, could also be provided.

6. TRIAL RESULTS AND TREATMENT METHODOLOGIES

In a further aspect of the present invention there is provided methods for delivering an agent to a living tissue, e.g. animal, plant or human. It is considered that by selectively choosing the operational parameters of the non-invasive agent applicator presently described, the amount of agent delivered to a selected depth within tissue may be controlled.

The controlled parameters may include one or more of:

Application pressure;

Ultrasonic frequency;

Ultrasonic waveform;

Ultrasound direction;

Ultrasonic power level;

Ultrasonic application duration; and

Ultrasound duty cycle.

In particularly preferred forms, the system parameters can be chosen to control the delivery of an agent to a desired depth in the target tissue. An example of this would be setting system parameters such that transepithelial delivery of an agent predominantly into the stroma of the cornea would occur. Advantageously, this presents the opportunity to deliver a drug, vaccine or other agent to a selected tissue depth where it is known to be most efficacious.

In this regard, the present invention in one form provides a method of controlling the amount of agent delivered to a selected depth within tissue using an agent carrier, agent carrier body or applicator of any one of the aspects or embodiments described herein.

Experimental Testing

A series of experiments were conducted using mice to determine if an agent can be successfully delivered to tissues using embodiments of the present invention. The transportation stimulus in each case was ultrasonic energy only. In the present experiments a vaccine virus was administered using an embodiment of the present invention, using ultrasonic energy only, applied to the inside of the lip to determine whether the agent was presented to the immune system, and may induce an immune response. Researchers noted that no damage occurred to the mucous membrane of the lip by the application of the device for the period required to achieve a systemic immune response in Experiment 2.

6.1 Experimental Summary

Experiment 1

Mice were vaccinated with an embodiment of the present invention illustrated in FIG. 7*c* using two agent carrier bodies (termed “microchips” in this discussion) totaling around 2-5×106 plaque forming units (pfu) of the fluorescent labelled recombinant poxviral vector-based HIV vaccine per mouse.

The proportion of antigen presenting cells taken up the vaccine antigen (0.025-0.068 vs 0.025-0.022), and the proportion of dendritic cells recruited to the draining lymph nodes (0.25-0.54 vs 0.22-0.49) were similar in immunised and unimmunised mice, respectively (FIGS. 1 and 2). The key conclusion was that an immune response was not instigated using only two microchips.

Experiment 2

A full heterologous prime-boost vaccination using recombinant poxviruses expressing HIV antigens was conducted using three microchips per mouse prime, and the responses were compared to mice primed intranasally (i.n.) (positive control), and to mice not primed with any vaccine (negative control). All mice were given an intramuscular (i.m.) booster vaccination two weeks after the priming vaccination.

The magnitude of the systemic immune responses (responses in the blood compartment) induced by different vaccination routes were evaluated by determining the percent of HIV-specific CD8 T cells in spleen. One of the mice vaccinated using an embodiment of the present invention generated an immune response that exceeded the positive control thus demonstrating proof of concept.

Experiment 3

In a further experiment a preliminary prime-boost vaccination experiment was conducted using embodiments of the present invention illustrated in FIG. 10. Mice were primed with the lip delivery system using three microchips according to each embodiment (around 2-5×10$^6$ pfu) of FPV-HIV per mouse, followed by an intramuscular booster vaccination. The percent of HIV-specific CD8 T cells was used to assess the magnitude of the immune responses induced. Data indicated that microchips 1 (1% of cells) and 2 (0.6%) performed slightly better than microchips 3 and 4 (0.5%). It was also noted that during loading and delivery the microchips 1 and 2 performed much more effectively than microchips 3 and 4.

Experiment 4

Full prime-boost vaccination experiment was performed using the microchips 1 and 2 of FIG. 10. In this experiment one of the mice in each of the groups vaccinated generated an immune response that exceeded the intranasal positive control, whereas the other two mice in each group had responses similar to the oral vaccine negative control group.

Table 1 summarises the experimental parameters and outcomes of each of the experiments.

2. Evaluate whether antigen presenting cells (APC) are recruited to these LN the relative number of dendritic cells (DCs) and macrophages at these sites were identified by the staining for characteristic cell surface markers Methods:

1. Mice were immunised with FPV-HIV-GFP and responses were evaluated 24 hours post vaccination. In these experiments, mice were also kept as either
   a) unimmunised controls (FIGS. 14 and 15), or
   b) controls vaccinated with only FPV-HIV (i.e. no GFP fluorescent antigen, FIG. 16).

Mice were given the vaccination with two microchips, one to the left and one to the right lip (around 5×10$^6$ pfu per mouse).

2. At 24 h the different draining lymph nodes were harvested, pooled, and single cell suspensions were prepared in complete medium (Ranasinghe et al., 2011, Ranasinghe et al., 2006, Ranasinghe et al., 2007, Ranasinghe et al., 2013)

3. 1×10$^6$ cells were aliquoted and stained with the different cell surface markers. [Antigen presenting MHC-II cells were stained with antibody to the I-A$^d$ APC cell surface marker Antibodies to cell surface markers CD11b-PE and CD11c-PerCP were used to identify DCs, (FIG. 15) and antibody to cell surface marker F4/80-PE Cy7 was used to identify macrophages (data not shown)] (Ranasinghe et al 2103)

TABLE 1

Summary of the prime-boost vaccination experiments conducted on the original microchip, and microchips 1 and 2.

| Chip identification where relevant[a] | Priming: route dose FPV-HIV[b] | Booster: route dose VV-HIV[c] | % HIV-specific CD8+ T cells (tetramer test)[d] | | | Magnitude of HIV-specific CD8+ T cell response (ICS test)[d] | | |
|---|---|---|---|---|---|---|---|---|
| | | | M#1 | M#2 | M#3 | M#1 | M#2 | M#3 |
| Original Mc (×3) Test group | Lip ~2.5 × 10$^6$ pfu | i.m. 1 × 10$^7$ pfu | 15.1 | 1.03 | 1.06 | 10.5 | 0.73 | 0.78 |
| Positive control | i.n. 1 × 10$^7$ pfu | i.m. 1 × 10$^7$ pfu | 8.94 | 9.33 | | 8.85 | 8.14 | |
| Negative control | | i.m. 1 × 10$^7$ pfu | 1.36 | 1.40 | | 1.03 | 0.78 | |
| Mc1 (×3) Test group | Lip ~2-5 × 10$^6$ pfu | i.m. 1 × 10$^7$ pfu | 0.38 | 15.6 | 0.67 | 0.06 | 1.5 | 0.08 |
| Mc2 (×3) Test group | Lip ~2-5 × 10$^6$ pfu | i.m. 1 × 10$^7$ pfu | 0.81 | 0.73 | 0.46 | 0.12 | 0.08 | 2.0 |
| Negative control | Oral 5 × 10$^6$ pfu | i.m. 1 × 10$^7$ pfu | 1.17 | 0.45 | 2.87 | 0.8 | 0.05 | 0.35 |

[a](×3) - refers to the number of microchips of vaccine administered to each mouse, thus "×3" means that three microchips were applied;
Mc - is an abbreviation of "microchip" and us used to designate which type was used in each test;
[b]Dose, is represented in plaque forming units (pfu) of the priming vaccine, fowl pox virus expressing HIV antigens (FPV-HIV) are provided. The route of vaccination delivery; is indicated as follows:
"Lip" designates that administration was made using an embodiment of the present invention applied to the tissues of the lip of the subject; "i.n." designates intranasal delivery; "oral" designates delivery directly into the mouth
[c]The booster vaccine is vaccinia virus expressing HIV antigens (VV-HIV), and in all cases this was delivered using intramuscular (i.m.) route
[d]In both cases, systemic immune response was investigated. M# represents mouse number.

6.2 Experimental Detail

Experiment 1

Aims: To determine whether the lip delivery system using the embodiment of FIG. 7c induced antigen uptake in the draining lymph nodes (LN), the antigen presentation and immune cell recruitment was monitored 24 hours post vaccination as follows:

1. Uptake of the vaccine antigens was monitored in cervical, mediastinal and/or mesenteric lymph nodes following administration of a number of microchips of a fluorescently labelled vaccine, recombinant fowl pox virus expressing HIV antigens together with green fluorescent protein (FPV-HIV-GFP);

4. Different cell subsets were analysed based on the fluorescent-labelled cell surface marker expressed on the cell surface using flow cytometry analysis (FACS). These experiments were repeated three times, combined results are presented in FIGS. 14 to 16

5. In these experiments singe colour controls (SS) and fluorescent minus one (FMO) controls were also used to set up the gating and perform the correct analysis of the different cell subsets.

Figure 14:
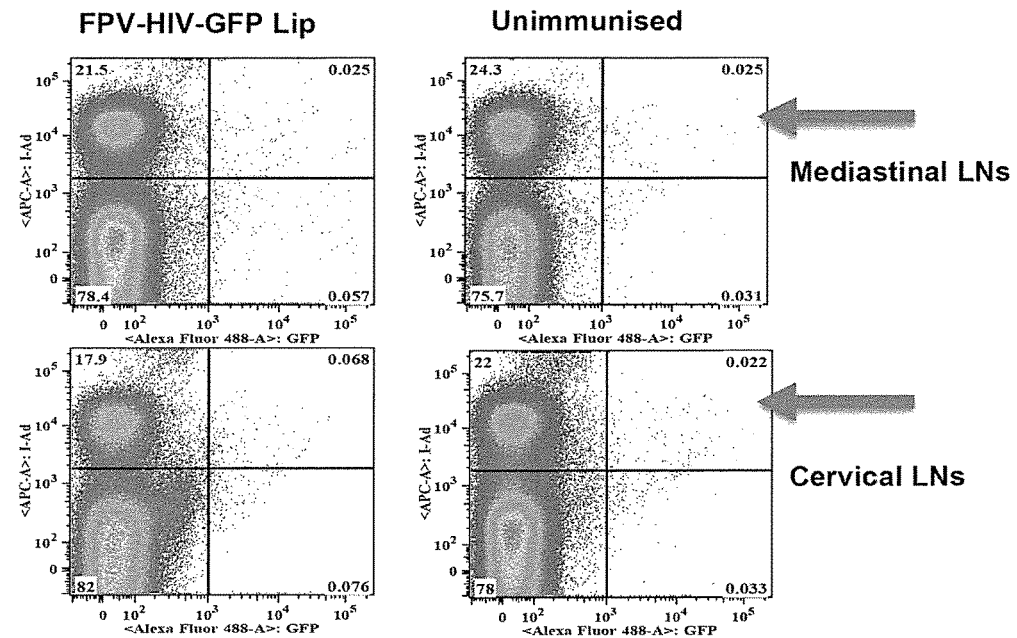
Figure 15:
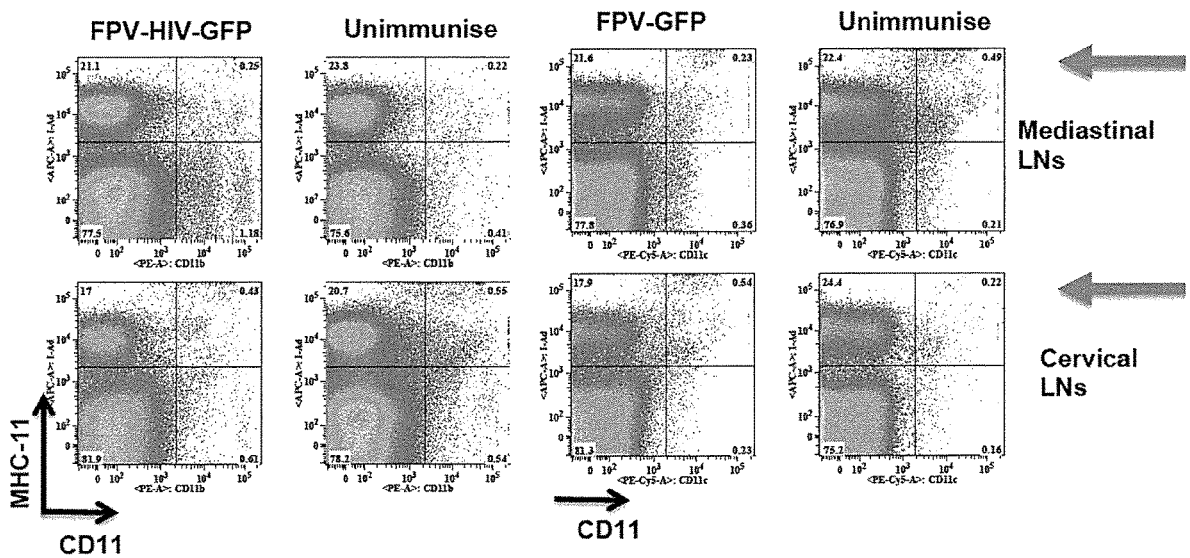
Figure 16:
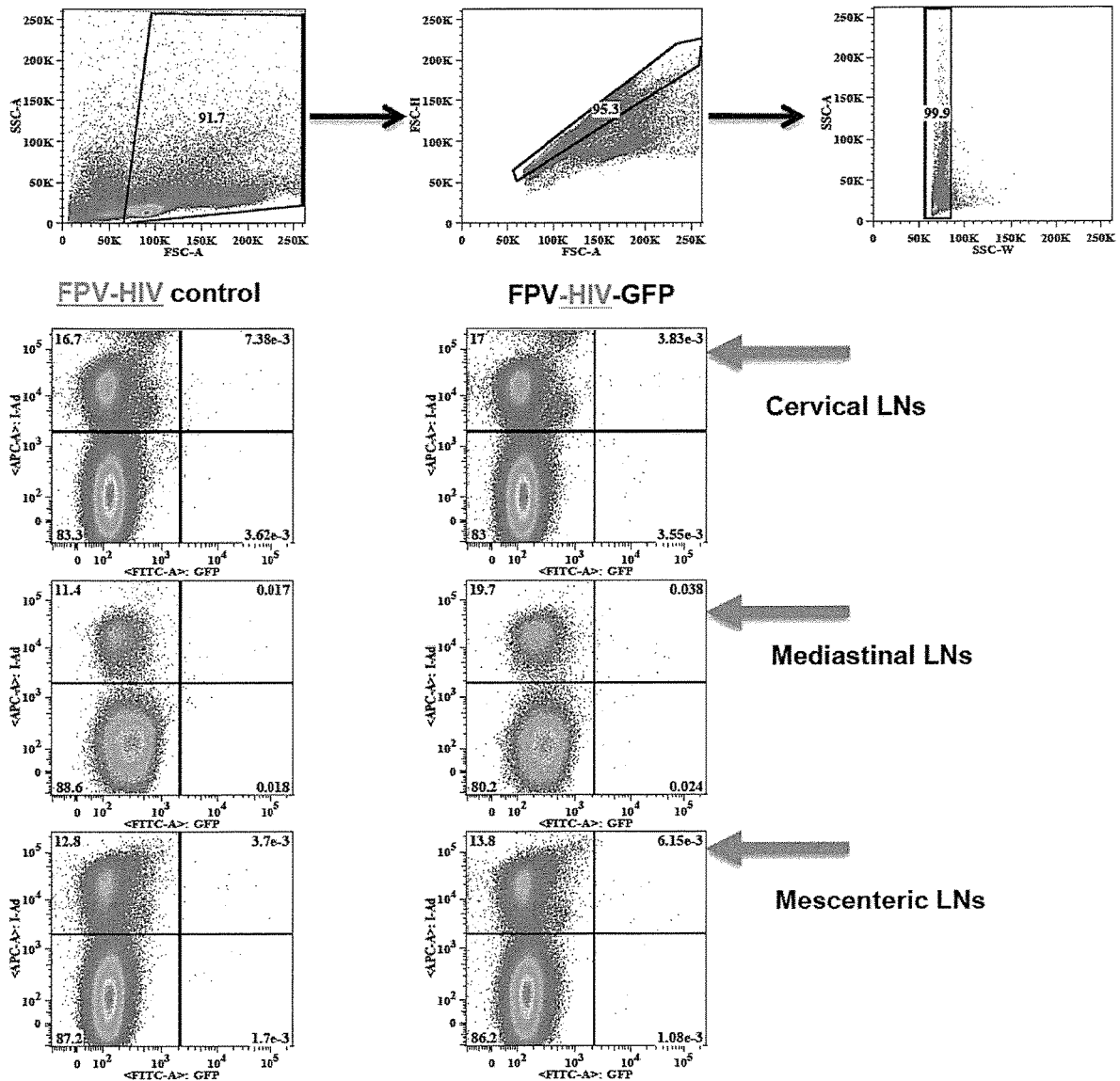

Results and Conclusions:

FIGS. 14 to 16 illustrate graphically the outcomes of the experiments. In this regard, FIG. 14 shows plots for the evaluation of the uptake of FPV-HIV-GFP vaccine 24 h post lip delivery, illustrating I-Ad APC MHC-II cells containing the fluorescent GFP antigen of the vaccine detected in the top right hand quadrant indicated by the arrow. Note in this and other FACS plots, each dot represents a single cell.

FIG. 15 illustrates plots for the evaluation of recruitment of antigen uptake by different dendritic cell subsets to the respective draining lymph nodes 24 h post lip delivery. The proportion of dendritic cells, identified as being MHC-11+, and either CD11 b+ (left two columns) or CD11c+ (right two columns) are indicated in the top right hand quadrant (refer to arrows).

FIG. 16 illustrates plots for the evaluation of the uptake of FPV-HIV-GFP vaccine 24 h post lip delivery in cervical, mediastinal and mesenteric nodes (repeat experiment 3) I-Ad APC MHC-II cells containing the fluorescent GFP antigen of the vaccine are detected in the top right hand quadrant indicated by the arrow. (Note that the top three graphs show the gating strategy).

As can be seen, no differences in the antigen uptake and presentation (FIGS. 14 & 16) or the DC subsets recruited to the draining lymph nodes (FIG. 15) were detected between the mice that received the FPVHIV-GFP vaccine and the controls. The data indicated that;
  i) Vaccine delivery applied at a dose of two microchips per mouse (dose ~2-5×10$^6$ pfu) was not effective.
  ii) Thus, to obtain any immune outcomes, a minimum of 3 chips or more per mouse were used in the subsequent prime-boost vaccination experiments.

Experiment 2

In this next experiment an evaluation of the efficacy of lip delivery with the same microchip as experiment 1, using prime-boost vaccination was performed.

Aims: To test whether lip prime followed by intramuscular (i.m.) booster vaccination can induce effective HIV-specific CD8 T cell immunity compared to intranasal prime (i.n.)/i.m. booster vaccination strategy using:
  1. HIV gag-specific tetramer staining.
  2. Intracellular cytokine staining (ICS) of IFN-γ in HIV-specific CD8 T cells.

Figure 17:
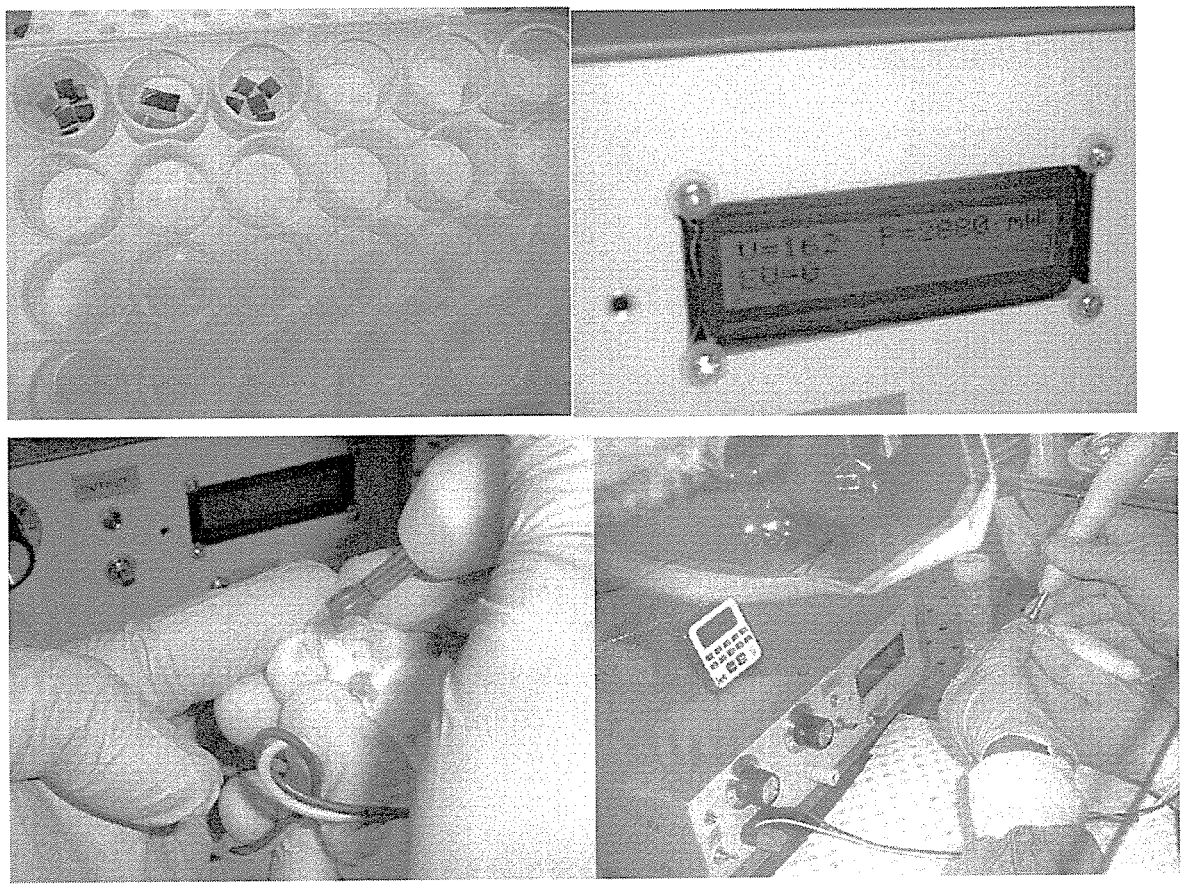

Methods:

FIG. 17 are photographs showing the following phases of the experiments performed. The phases illustrated include: Loading the microchips (top left), Ultrasonic system settings (top right) and lip delivery to the mice (bottom photos). The experimental method was performed as follows:
  1) Priming Vaccination with FPV-HIV
  a. Vaccine (~600-800 μl of the stock) was sonicated (i.e. output: 30%; 3 cycles for 10 seconds per cycle) as for routine i.n. delivery. 300-400 μl/well of the sonicated virus was added into two wells of a 48 well plate.
  b. Microchips were soaked in FPV-HIV (5×10$^8$ PFU/ml) in a 48 well plate (FIG. 17 top left). It was assumed that each microchip could absorb and expel 5 μl, thus the dose per microchip was calculated to be 2.5×10$^6$ pfu.
  c. Six microchips per well were submerged in liquid without any overlap and incubated for 30 minutes on ice (FIG. 17 top left).
  d. One microchip was taken out to test whether the chips were loaded with virus, by placing the loaded microchip in a well containing PBS. If the microchip floated it meant the chip was not loaded, but if it sank it was considered to be loaded.
  e. Controls: positive control two mice were immunised i.n. (20 μl/mouse 1×10$^7$ pfu) and two mice were vaccinated with i.m. booster (1×10$^7$ pfu) only to solely test its effect.
  f. Test group: three mice were immunised for the lip/i.m. group as follows. The microchip was mounted to the delivery applicator, similar to that illustrated in FIG. 1, that was connected to the power source. Ultrasonic gel was used between the arm and the microchip for better contact). Power was switched on.
  g. Microchip was pressed firmly onto the inner lip region of an anesthetised mouse. (FIG. 17 bottom)
  h. Output switch was turned on an ultrasonic energy was applied for 30 seconds, to deliver the virus into the lip region. At this time point the instrument settings were transducer drive voltage V=95-160; P=2800-3200 mW.
  i. To check whether the virus has been delivered from the microchip, the chip was placed in PBS as before. If the chip floated it suggested that the virus was successfully expelled from the chip. 80% of the time the chip floated suggesting that the vaccine was expelled. If two microchips failed to deliver the vaccine correctly, the mouse was discarded and a new mouse was immunised.
  j. This was repeated for 3 microchips per mouse, using one new chip each time.

2) Intramuscular Booster Vaccination Using 10$^7$ PFU VV-HIV
  a. Booster vaccination was performed two weeks post FPV-HIV priming vaccination
  b. Booster vaccine was prepared for 9 mice total 9×10$^7$ PFU in 900 μl of PBS.
  c. Virus was sonicated exactly as done for the FPV-HIV.
  d. Mice were anesthetized with isoflurane using a nose cone and 50 μl of VV-HIV per quadriceps muscle was delivered i.m.

3) Preparation of Spleen Samples for Analysis 7-14 days post booster vaccination spleens were harvested from each mouse, and single cell suspensions were prepared as described in Ranasinghe et al (2006).

The magnitude of the HIV-specific CD8 T cell responses was assessed with tetramer staining and intracellular cytokine staining, using 4×10$^6$ spleen cells from each mouse according to the plate scheme in Tables 2 and 3 as follows:
  a. Tetramer staining was performed as described in (Ranasinghe et al., 2011, Ranasinghe et al., 2006, Ranasinghe et al., 2007, Ranasinghe et al., 2013)

Cells were stained for 45 min at room temperature with K$^d$Gag197-205-APC tetramer and anti-CD8α FITC in FACS buffer.

Cells were washed and fixed in 0.5% PFA prior to analysis using FACS.
    b. Intra cellular cytokine staining (ICS) for IFN-γ was also performed as described (Ranasinghe et al., 2011, Ranasinghe et al., 2006, Ranasinghe et al., 2007, Ranasinghe et al., 2013)

Cells were stimulated over night with K$^d$Gag197-205 peptide for 1 h at 37° C.+5% CO2

Brefeldin A was added to each well and incubated for further 5 hours at 37° C.

Cells were surface stained for 25 mins at 4° C. with anti-CD8α FITC in FACS buffer.

Cells were fixed/permeabilized using IC/fix and IC/perm from eBioscience

Cells were then intracellular stained with anti-IFN-γ, for 25 mins at 4° C. (Table 2)

Positive stain—anti IFN-γ APC in in IC Perm

Single colour controls and FMO's.

TABLE 2

Plate Scheme for Tetramer Staining.

|   | 1 | 2 | 3 | 4 | 5 | 6 | 7 | 8 | 9 |
|---|---|---|---|---|---|---|---|---|---|
| A ss cont | Unstain | FITC | APC | | | | | | |
| B | LIP 1 | LIP 2 | LIP 3 | i.n. 1 | i.n. 2 | Boost only 1 | Boost only 2 | FMO CD8 | FMO tetramer |

TABLE 3

Plate Scheme for ICS.

|   | 1 | 2 | 3 | 4 | 5 | 6 | 7 | 8 | 11 |
|---|---|---|---|---|---|---|---|---|---|
| A ss cont | Unstain | FITC | APC | | | | | | |
| B stimulated | LIP 1 | LIP 2 | LIP 3 | i.n. 1 | i.n. 2 | Boost only 1 | Boost only 2 | FMO CD8 | FMO IFN-g |
| C Unstim | LIP 1 | LIP 2 | LIP 3 | i.n. 1 | i.n. 2 | Boost only 1 | Boost only 2 | | |

SS = Single colour control,
FMO = Fluorescent minus one

Figure 18:
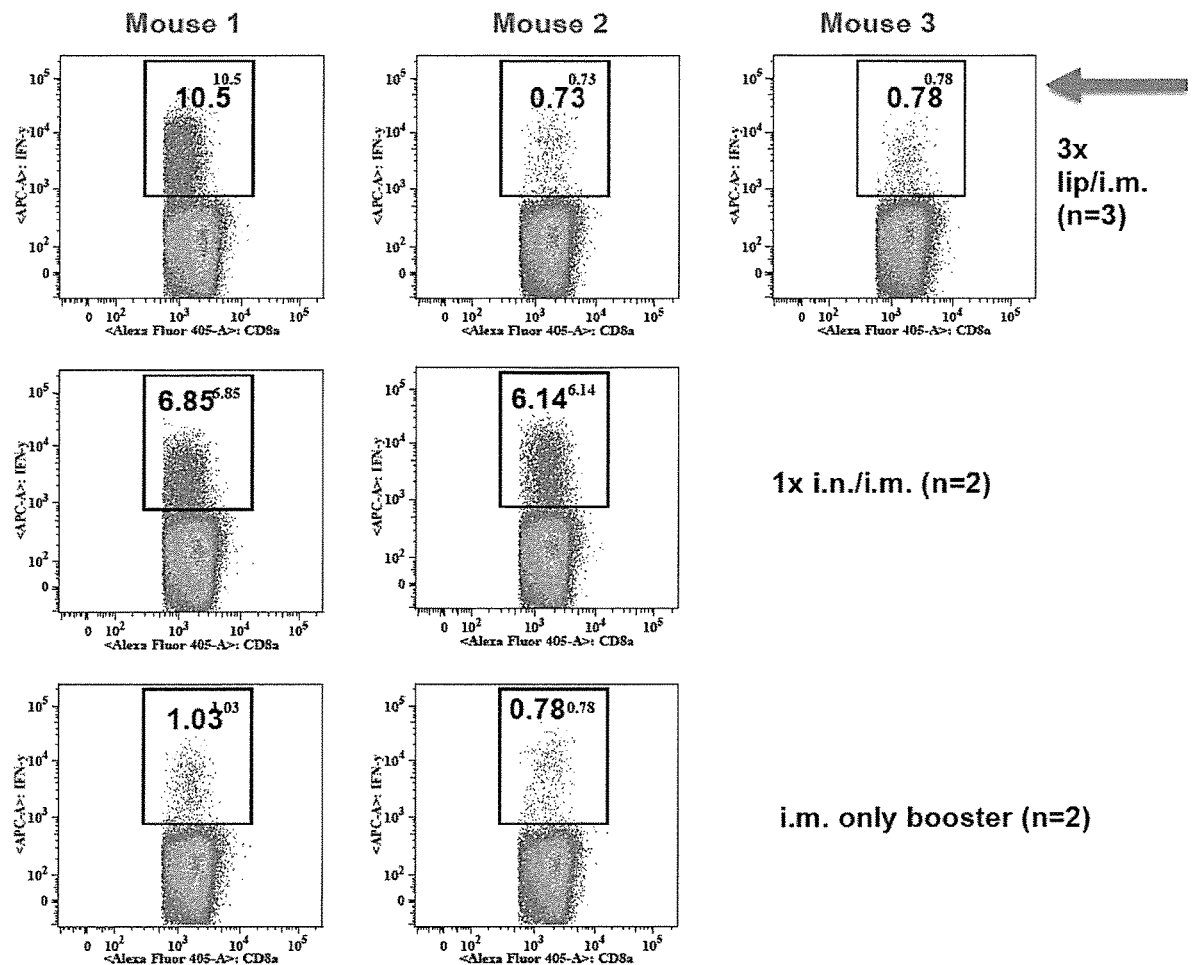
Figure 19:
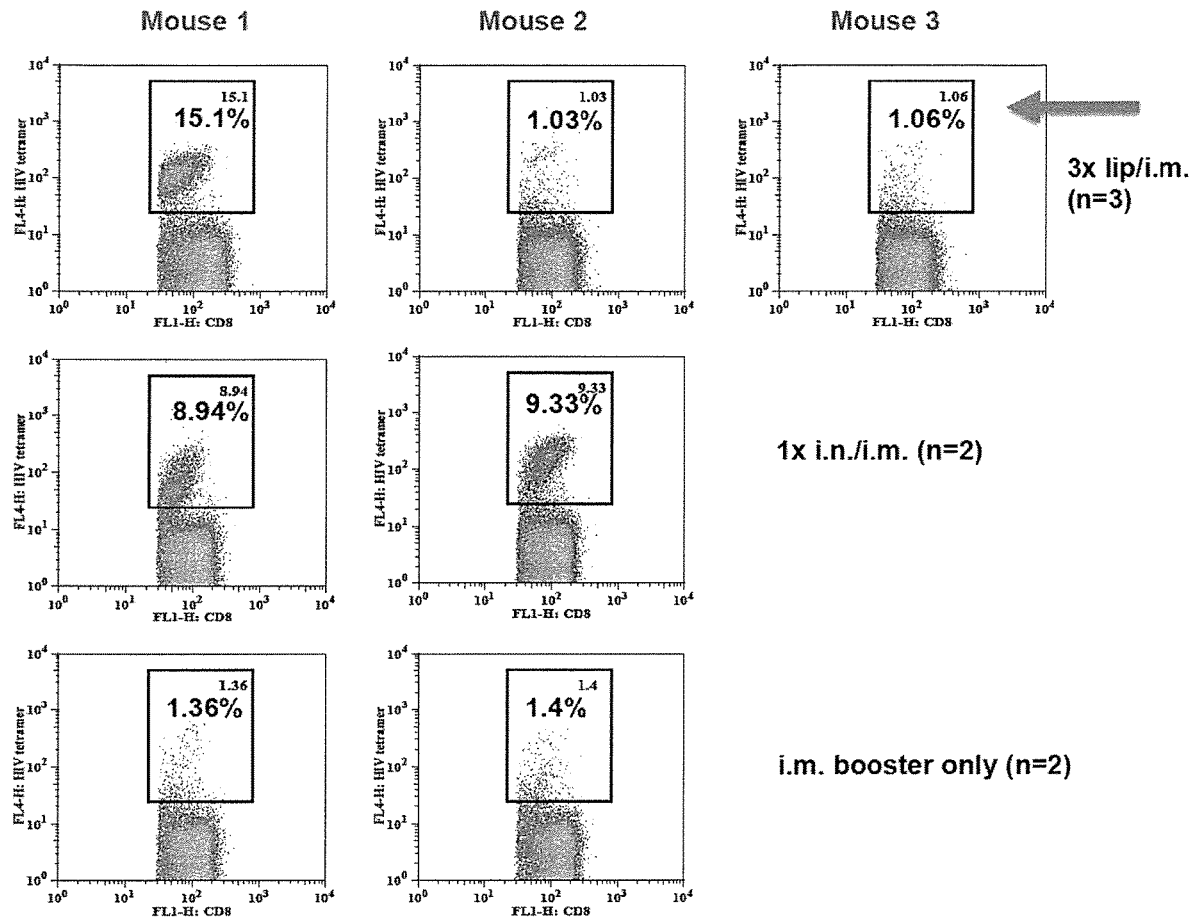

Results and Conclusions:

FIG. 18 shows plots illustrating the evaluation of the magnitude of HIV-specific splenic CD8 T cells using IFN-γ intracellular staining. The FACS data were analyzed using Cell Quest Pro or FlowJo analysis. The box indicates the percentage of HIV-specific splenic CD8 T cells expressing IFN-γ following Lip/i.m. (top 3 mice), i.n./i.m. (middle 2 mice) and booster only (bottom 3 mice) vaccinations. FIG. 19 illustrates plots enabling evaluation of HIV-specific splenic CD8 T cells using tetramer staining. Cells were stained as described in materials and methods. The FACS data were analysed using Cell Quest Pro or FlowJo analysis. The box indicates the percentage of HIV-specific splenic CD8 T cells following different routes of vaccine delivery. Lip/i.m. (top three mice), i.n./i.m. (middle two mice) and booster only (bottom two mice).

The HIV-specific tetramer (FIG. 18) and IFN-γ staining (FIG. 19) data indicated that unlike the i.n./i.m. delivery strategy that gave highly consistent results (FIG. 18—range 8.94-9.33%), the lip/i.m. delivery strategy did not yield consistent outcomes (FIG. 19—range 1.03-15.1%). Whilst it appears that this is due to the inconsistency of the priming of the mice during lip delivery (Note: see also lip/i.m. compared to i.m. booster only), one mouse (mouse 1) showed an immune response that exceeded that of the i.n./i.m. delivery strategy, indicating that a response is possible using embodiments of the present invention.

Data also revealed that 3× lip or 4× lip microchip delivery was more effective than 5× lip microchip delivery (data not shown). These experiments were performed twice and data were found to be very similar between the experiments (Experiments 4 & 5). Data are representative of one experiment.

Experiments 3:

A further experiment was performed to test prime-boost vaccination strategy to assess the efficacy of lip delivery using four protrusion-based embodiments of the present invention illustrated in FIG. 10.

Figure 20:
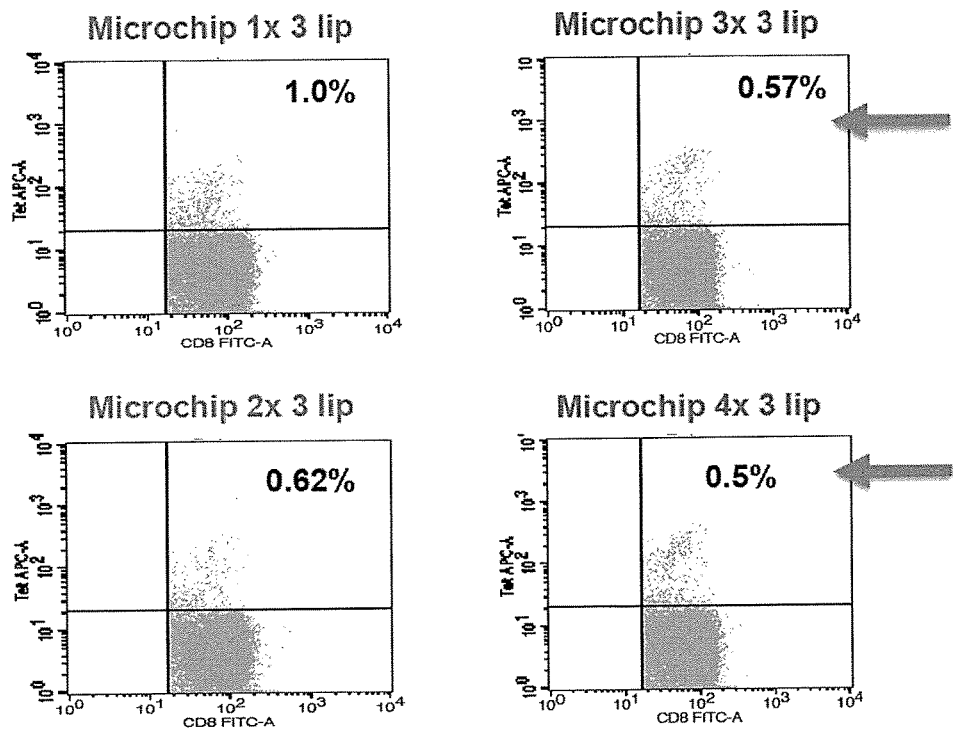

Aims: To test whether these microchips can load and deliver the vaccine more effectively to the lip compared to microchips of FIG. 7c using HIV gag-specific tetramer staining (FIG. 20).

1) Priming Vaccination with FPV-HIV a. Vaccine was sonicated and 300-400 ml per well was added into a 48 well plate as before.

b. The microchips were connected to the device, then 5-7 µl of vaccine was loaded onto the tissue contacting surface of the microchip using a pipette and immediately delivered to the lip of the mouse. Unlike the microchip of FIG. 7c, these improved microchips were NOT soaked in FPV-HIV for 30 min.

c. Controls: for the positive control, two mice were immunised i.n. (20 ml/mouse), for the negative controls, two mice were immunised orally and two mice were kept as controls for the i.m. booster only to test the effect of i.m. vaccination only. (similar to FIG. 5)

2) i.m. Booster Vaccination and Evaluation of Immune Responses Using Tetramer Staining a) These were performed exactly as described in experiment 2.

Results and Conclusions:

1) Unlike the microchip of FIG. 7c, direct pipetting of the vaccine onto the chips made it extremely easy to determine whether the new microchips were properly loaded. Similarly, once the vaccination was performed, the microchip was placed on a piece of tissue to determine whether the vaccine had been properly expelled. If the microchip was dry it meant the vaccine was delivered. We also tested the above loading by visualising the empty, loaded and used microchips under a microscope.

2) It was observed that microchips 1 & 2 (FIG. 10 top) loaded and discharged the vaccine much more effectively (without leakage) compared to microchips 3 and 4 (FIG. 10 bottom). Even though loading was much more effective, the vaccine leaked out of microchip 3 (in particular) and 4 as soon as the device was held against the lip, prior to turning on the output switch, making it more of an oral delivery.

3) The preliminary HIV-specific tetramer data further confirmed that microchip 1 performed better than 3 & 4. Hence, it was decided to repeat the prime-boost vaccination experiments with microchips 1 and 2 of FIG. 10, including an oral prime/i.m. booster immunization strategy as a control to validate the data in experiment 4, below.

Experiment 4

In this experiment vaccination using a 3× lip/i.m. vaccination strategy using microchips 1 & 2 was tested in a similar manner to previous experiments.

Aim: Test the efficacy 3× lip/i.m, vaccination strategy compared to 1× oral/i.m. prime-booster vaccination using:
a) HIV gag-specific tetramer staining (FIG. 21) and
b) Intracellular cytokine staining (ICS) of IFN-γ (FIG. 22)

Methods:

Vaccination and analysis were performed exactly as in experiment 3 with 3 mice per group. 1× oral prime/i.m. booster vaccination was also performed as an additional control to assess whether the priming was related to oral delivery or lip delivery (oral dose=5×106 FPV-HIV). The HIV-specific CD8 T cell responses were measured in the spleen 14 days post booster vaccination using tetramer staining and intracellular IFN-γ staining. The experiments were performed two times.

Figure 21:
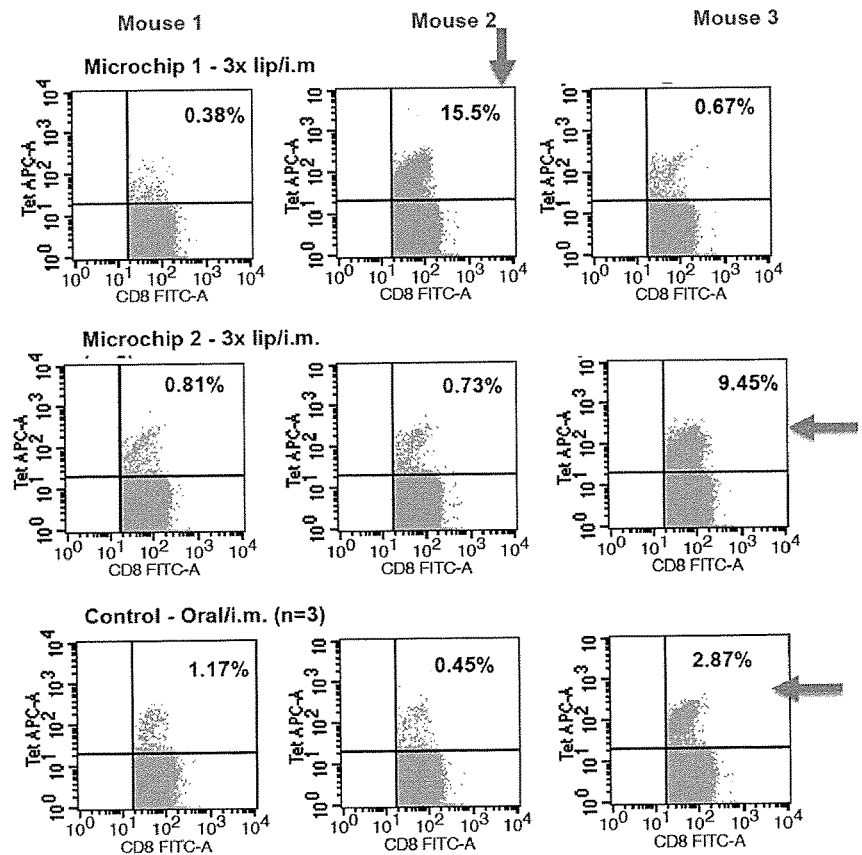
Figure 22:
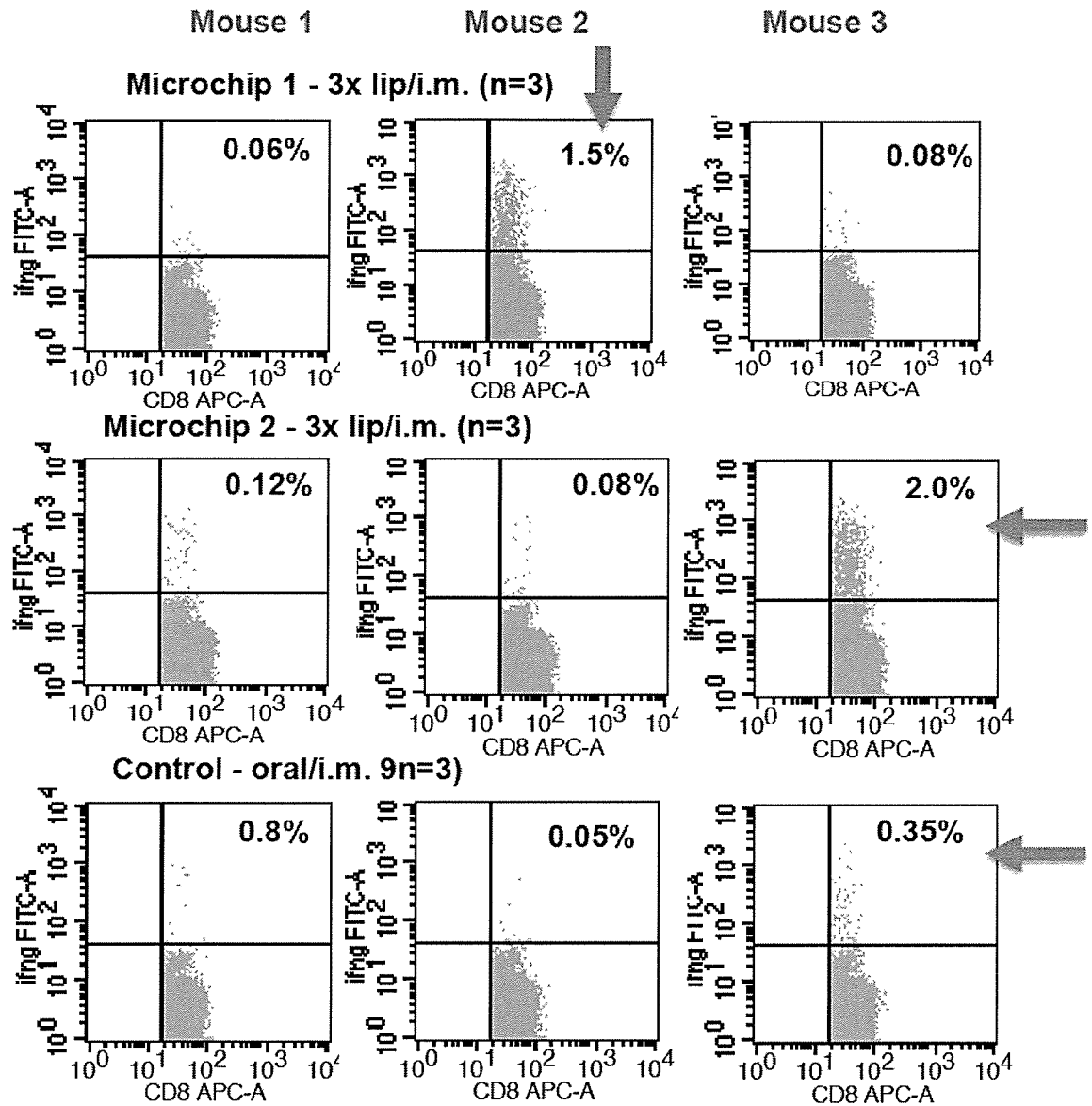

Results and Conclusion:

FIG. 21 illustrates plots enabling evaluation of HIV-specific splenic CD8 T cell responses using tetramer staining. The FACS data were analysed using Cell quest Pro software. Plots represent three animals per group microchip 1 (top) & 2 (middle) prime-boost immunization data compared to oral delivery (bottom). The upper right quadrants (red arrows) indicate the % of HIV-specific CD8 T cells observed following each vaccine strategy.

FIG. 22 illustrates plots enabling evaluation of the magnitude of HIV-specific CD8 T cell responses using IFN-γ intra cellular cytokine staining. The FACS data were analysed using Cell quest Pro software. Plots represent three animals per group microchip 1 (top) & 2 (middle) prime-boost immunization data compared to oral delivery (bottom). The upper right quadrants (red arrows) indicate the % of HIV-specific CD8 T cells expressing IFN-γ.

As can be seen the HIV-specific splenic CD8 T cell responses observed with microchip 1—mouse 2 and microchip 2—mouse 3 (red arrows) were greatly elevated compared to oral delivery (bottom 3 mice FIGS. 21 & 22), these results clearly indicated that the responses observed were due to lip uptake not oral uptake.

Data indicated that if the delivery was uniform/consistent the microchip 1 and 2 could induce good HIV-specific CD8 T cell immunity in the blood compartment.

The positive responses detected with the microchips made in accordance with FIG. 10 were very much similar to the positive responses detected with the microchip of FIG. 7c used in experiments 1 and 2). However, they present greater ease of loading.

Data from experiments, suggest that if uniformity/consistency could be attained, lip delivery could be more effective than oral or intranasal delivery.

Discussion

Molecules that are known to the inventors to possibly be delivered to the body using sonophoresis include 1) molecules of any kind of electric charge or have a neutral (including overall neutral) electrical charge and 2) small or large molecules (including monoclonal antibodies of approximately 149,000 Daltons) 3) molecules that are hydrophilic or hydrophobic or lipophilic.

7. REFERENCES

References: RANASINGHE, C., EYERS, F., STAMBAS, J., BOYLE, D. B., RAMSHAW, I. A. & RAMSAY, A. J 2011. A comparative analysis of HIV-specific mucosal/systemic T cell immunity and avidity following rDNA/rFPV and poxvirus-poxvirus prime boost immunisations. Vaccine, 29, 3008-20

RANASINGHE, C., MEDVECZKY, J. C., WOLTRING, D., GAO, K., THOMSON, S., COUPAR, B E. H., BOYLE, D. B., RAMSAY, A. J. & I. A., R. 2006. Evaluation of fowlpox-vaccinia virus prime-boost vaccine strategies for high-level mucosal and systemic Immunity against HIV-1. Vaccine, 24, 5881-5895

RANASINGHE, C., TRIVEDI, S., STAMBAS, J. & JACKSON, R. J. 2013. Unique IL-13Ralpha2-based HIV-1 vaccine strategy to enhance mucosal immunity, CD8(+) T-cell avidity and protective immunity. Mucosal Immunol, 6, 1068-80

RANASINGHE, C., TURNER, S. J., MCARTHUR, C., SUTHERLAND, D. B., KIM, J. H., DOHERTY, P. C. & RAMSHAW, I. A. 2007. Mucosal HIV-1 pox virus prime-boost immunization Induces high-avidity CD8+ T cells with regime-dependent cytokine/granzyme B profiles. J Immunol., 178, 2370-9

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method of dispensing an agent from an agent carrier to the eye, the method comprising:

holding the agent within an agent carrier, wherein said agent carrier includes a solid agent carrier body that comprises a plurality of substantially parallel microchannels integral with and extending at least partially through the agent carrier body and terminating at a tissue contacting surface of the agent carrier body in a series of individual pores of up to 1000 μM in size, wherein the microchannels enable the holding and transportation of the agent through the agent carrier body to the tissue contacting surface, wherein the holding includes holding the agent within the microchannels in the agent carrier body prior to dispensing, and wherein the agent carrier does not include a fluidically separate reservoir for storing agent;

non-invasively applying the tissue contacting surface of the agent carrier body directly to the conjunctiva and/or cornea of the eye, such that each microchannel pore terminates directly on the conjunctiva and/or cornea of the eye; and dispensing agent held in the microchannels in the agent carrier body to the conjunctiva and/or cornea of the eye by applying ultrasonic waves having a power of between 0.05 Wcm$^{-2}$ and 3.5 Wcm$^{-2}$ longitudinally along the microchannels in the agent carrier body to cause transportation of the agent through the microchannels in the agent carrier body to the conjunctiva and/or cornea of the eye;

wherein:

the dispensing step further includes applying only the ultrasonic waves through the agent carrier body to the conjunctiva and/or cornea to non-invasively facilitate penetration of the agent into the conjunctiva and/or cornea via sonophoresis, and the microchannels are each surrounded by rigid walls of the solid agent carrier body.

2. The method of claim 1, wherein the ultrasonic waves are selected to deliver a chosen amount of agent to a chosen depth within the tissue.

3. The method of claim 1, wherein operational parameters of the agent carrier are used to enhance or cause delivery of said agent to a selected depth within the tissue, and the operational parameters are selected from one or more of: application pressure, ultrasonic frequency, ultrasonic power level, ultrasonic waveform, ultrasonic application duration, ultrasonic application duty cycle, ultrasound direction.

4. The method of claim 1, wherein the agent carrier body is able to conduct a transmission stimulus to transport the agent within the agent carrier body and to the tissue surface.

5. The method of claim 1, wherein the agent carrier is a component of an applicator device.

6. The method of claim 5, wherein the agent carrier or agent carrier body are coupled directly or indirectly to a handle unit of the applicator device to facilitate handheld control of the applicator device.

7. The method of claim 6, wherein the handle unit includes a generator of ultrasound energy to generate the ultrasonic waves, and the ultrasonic waves are transmitted to the agent carrier.

8. The method of claim 7, wherein the handle unit is coupled to the agent carrier or agent carrier body via a coupling rod and the ultrasonic waves are transmitted from the generator of ultrasound energy to the agent carrier body through the coupling rod.

9. The method of claim 1, wherein the agent carrier is a consumable applicator tip adapted for single use.

10. The method of claim 1, wherein operational parameters of the agent carrier are used to enhance delivery of said agent to a selected depth within the tissue, and the operational parameters are selected from one or more of: application pressure, ultrasonic frequency, ultrasonic power level, ultrasonic waveform, ultrasonic application duration, ultrasonic application duty cycle, and ultrasound direction.

11. The method of claim 1, wherein operational parameters of the agent carrier are used to cause delivery of said agent to a selected depth within the tissue, and the operational parameters are selected from one or more of: application pressure, ultrasonic frequency, ultrasonic power level, ultrasonic waveform, ultrasonic application duration, ultrasonic application duty cycle, ultrasound direction.

12. The method of claim 1, wherein the microchannels are each an internal exposed surface within the solid agent carrier body.

* * * * *